(12) United States Patent
Debant et al.

(10) Patent No.: US 8,088,892 B2
(45) Date of Patent: Jan. 3, 2012

(54) INHIBITORS OF PROTEINS FROM THE RHO-GEF FAMILY

(75) Inventors: Anne Debant, Prades le Lez (FR); Susanne Schmidt, Montpellier (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 357 days.

(21) Appl. No.: 12/210,992

(22) Filed: Sep. 15, 2008

(65) Prior Publication Data

US 2009/0036379 A1     Feb. 5, 2009

Related U.S. Application Data

(62) Division of application No. 10/515,838, filed as application No. PCT/EP03/005485 on May 26, 2003, now abandoned.

(30) Foreign Application Priority Data

May 29, 2002   (EP) .................................... 02291312

(51) Int. Cl.
    *C07K 71/00*  (2006.01)
    *C07H 21/04*  (2006.01)
    *A61K 38/22*  (2006.01)
(52) U.S. Cl. ........ 530/350; 536/23.1; 530/324; 530/325
(58) Field of Classification Search ............. 530/350, 530/324, 325; 536/23.1
See application file for complete search history.

(56) References Cited

U.S. PATENT DOCUMENTS

| 5,292,646 | A | 3/1994 | McCoy et al. |
| 5,994,070 | A | 11/1999 | Streuli et al. |
| 6,238,881 | B1 | 5/2001 | Hart |
| 2002/0165145 | A1 | 11/2002 | Meyers |

OTHER PUBLICATIONS

S. Schmidt et al., "Functional Study of the RHO-GEF Domains of Trio by Selecting Novel Peptide Inhibitors" Apr. 2000, Biology of the Cell, Congress of the French Society of Cell Biology, Paris, France, vol. 92, No. 2, pp. 172, XP001145963.
P. Colas et al., "Genetic Selection of Peptide Aptamers That Recognize and Inhibit Cyclin-Dependent Kinase 2", Apr. 11, 2000, Nature, Macmillan Jornals Ltd., London, United Kingdom, vol. 380, pp. 548-550, XP000904376.
Database Swissprot 'Online!, Jul. 21, 1986, XP002231905, Database Accession No. P00274.
Database Swissprot 'Online!, Jul. 4, 2000, XP002231906, Database Accession No. AAF33471.
Database Swissprot 'Online!, Mar. 1, 2002, XP002231907, Database Accession No. Q8XAT2.
Database Swissprot 'Online!, Nov. 25, 2001, XP002231908, Database Accession No. AC102676 NT 33327-33524.
S. Estrach et al., "The Human RHO-GEF trio and its Target GTPASE RHOG Are Involved in the NGF Pathway, Leading to Neurite Outgrowth", Feb. 19, 2002, Current Biology, Elsevier Science Ltd., vol. 12, pp. 307-312, XP001145960.
C.R. Geyer and R Brent, "Selection of Genetic Agents From Random Peptide Aptamer Expression Libraries", Methods Enzymol, vol. 328, 2000, pp. 171-208, XP001157025.
"Homology in Proteins and Nucleic Acids: A Terminology Muddle and a Way Out of it", 1987, Cell, Cell Press, Cambridge, NA, US, vol. 50 pp. 667, XP002913075.

*Primary Examiner* — T. D. Wessendorf
(74) *Attorney, Agent, or Firm* — Young & Thompson

(57) ABSTRACT

A method for screening peptides with an aptamer library for determining inhibitors of any one of the proteins from the Rho-GEFs family.

4 Claims, 8 Drawing Sheets

SEQUENCE LISTING

```
<160> NUMBER OF SEQ ID NOS: 63

<210> SEQ ID NO 1
<211> LENGTH: 465
<212> TYPE: DNA
<213> ORGANISM: artificial sequence
<220> FEATURE:
<223> OTHER INFORMATION: TRIAP-alpha
```

-continued

```
<220> FEATURE:
<221> NAME/KEY: CDS
<222> LOCATION: (1)..(462)

<400> SEQUENCE: 1 atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
                20                  25                  30 tgc ggt ccg gcg agg gag ggg gct gat ggt gcg att tgt ggt tat aat     144
Cys Gly Pro Ala Arg Glu Gly Ala Asp Gly Ala Ile Cys Gly Tyr Asn
            35                  40                  45 ttg gct acg ttg gtt atg ctg ggt ccg agt gag cgg gtg ttt tgt ccg     192
Leu Ala Thr Leu Val Met Leu Gly Pro Ser Glu Arg Val Phe Cys Pro
        50                  55                  60 ctt tgt gag cct tgt agt tct gat att tat gag ttg atg ggt ccg tgc     240
Leu Cys Glu Pro Cys Ser Ser Asp Ile Tyr Glu Leu Met Gly Pro Cys
65                  70                  75                  80 aaa atg atc gcc ccg att ctg gat gaa atc gct gac gaa tat cag ggc     288
Lys Met Ile Ala Pro Ile Leu Asp Glu Ile Ala Asp Glu Tyr Gln Gly
                85                  90                  95 aaa ctg acc gtt gca aaa ctg aac atc gat caa aac cct ggc act gcg     336
Lys Leu Thr Val Ala Lys Leu Asn Ile Asp Gln Asn Pro Gly Thr Ala
            100                 105                 110 ccg aaa tat ggc atc cgt ggt atc ccg act ctg ctg ctg ttc aaa aac     384
Pro Lys Tyr Gly Ile Arg Gly Ile Pro Thr Leu Leu Leu Phe Lys Asn
        115                 120                 125 ggt gaa gtg gcg tcg gca acc aaa gtg ggt gca ctg tct aaa ggt cag     432
Gly Glu Val Ala Ser Ala Thr Lys Val Gly Ala Leu Ser Lys Gly Gln
130                 135                 140 ttg aaa gag ttc ctc gac gct aac ctg gcg taa                         465
Leu Lys Glu Phe Leu Asp Ala Asn Leu Ala
145                 150

<210> SEQ ID NO 2
<211> LENGTH: 154
<212> TYPE: PRT
<213> ORGANISM: artificial sequence
<220> FEATURE:
<223> OTHER INFORMATION: Synthetic Construct

<400> SEQUENCE: 2

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ala Arg Glu Gly Ala Asp Gly Ala Ile Cys Gly Tyr Asn
            35                  40                  45

Leu Ala Thr Leu Val Met Leu Gly Pro Ser Glu Arg Val Phe Cys Pro
        50                  55                  60

Leu Cys Glu Pro Cys Ser Ser Asp Ile Tyr Glu Leu Met Gly Pro Cys
65                  70                  75                  80

Lys Met Ile Ala Pro Ile Leu Asp Glu Ile Ala Asp Glu Tyr Gln Gly
                85                  90                  95

Lys Leu Thr Val Ala Lys Leu Asn Ile Asp Gln Asn Pro Gly Thr Ala
            100                 105                 110

Pro Lys Tyr Gly Ile Arg Gly Ile Pro Thr Leu Leu Leu Phe Lys Asn
        115                 120                 125
```

```
Gly Glu Val Ala Ser Ala Thr Lys Val Gly Ala Leu Ser Lys Gly Gln
        130                 135                 140

Leu Lys Glu Phe Leu Asp Ala Asn Leu Ala
145                 150

<210> SEQ ID NO 3
<211> LENGTH: 126
<212> TYPE: DNA
<213> ORGANISM: artificial sequence
<220> FEATURE:
<223> OTHER INFORMATION: TRIP-alpha
<220> FEATURE:
<221> NAME/KEY: CDS
<222> LOCATION: (1)..(126)
<223> OTHER INFORMATION: TRIP-alpha

<400> SEQUENCE: 3 gcg agg gag ggg gct gat ggt gcg att tgt ggt tat aat ttg gct acg      48
Ala Arg Glu Gly Ala Asp Gly Ala Ile Cys Gly Tyr Asn Leu Ala Thr
1               5                   10                  15 ttg gtt atg ctg ggt ccg agt gag cgg gtg ttt tgt ccg ctt tgt gag      96
Leu Val Met Leu Gly Pro Ser Glu Arg Val Phe Cys Pro Leu Cys Glu
            20                  25                  30 cct tgt agt tct gat att tat gag ttg atg                             126
Pro Cys Ser Ser Asp Ile Tyr Glu Leu Met
        35                  40

<210> SEQ ID NO 4
<211> LENGTH: 42
<212> TYPE: PRT
<213> ORGANISM: artificial sequence
<220> FEATURE:
<223> OTHER INFORMATION: Synthetic Construct

<400> SEQUENCE: 4

Ala Arg Glu Gly Ala Asp Gly Ala Ile Cys Gly Tyr Asn Leu Ala Thr
1               5                   10                  15

Leu Val Met Leu Gly Pro Ser Glu Arg Val Phe Cys Pro Leu Cys Glu
            20                  25                  30

Pro Cys Ser Ser Asp Ile Tyr Glu Leu Met
        35                  40

<210> SEQ ID NO 5
<211> LENGTH: 102
<212> TYPE: DNA
<213> ORGANISM: artificial sequence
<220> FEATURE:
<223> OTHER INFORMATION: TRIP-alpha 9-42, fragment of TRIP-alpha
<220> FEATURE:
<221> NAME/KEY: CDS
<222> LOCATION: (1)..(102)

<400> SEQUENCE: 5 att tgt ggt tat aat ttg gct acg ttg gtt atg ctg ggt ccg agt gag      48
Ile Cys Gly Tyr Asn Leu Ala Thr Leu Val Met Leu Gly Pro Ser Glu
1               5                   10                  15 cgg gtg ttt tgt ccg ctt tgt gag cct tgt agt tct gat att tat gag      96
Arg Val Phe Cys Pro Leu Cys Glu Pro Cys Ser Ser Asp Ile Tyr Glu
            20                  25                  30 ttg atg                                                             102
Leu Met

<210> SEQ ID NO 6
<211> LENGTH: 34
<212> TYPE: PRT
<213> ORGANISM: artificial sequence
```

```
<220> FEATURE:
<223> OTHER INFORMATION: Synthetic Construct

<400> SEQUENCE: 6

Ile Cys Gly Tyr Asn Leu Ala Thr Leu Val Met Leu Gly Pro Ser Glu
1               5                   10                  15

Arg Val Phe Cys Pro Leu Cys Glu Pro Cys Ser Ser Asp Ile Tyr Glu
            20                  25                  30

Leu Met

<210> SEQ ID NO 7
<211> LENGTH: 96
<212> TYPE: DNA
<213> ORGANISM: artificial sequence
<220> FEATURE:
<223> OTHER INFORMATION: TRIP-alpha 9-40, fragment of TRIP-alpha
<220> FEATURE:
<221> NAME/KEY: CDS
<222> LOCATION: (1)..(96)

<400> SEQUENCE: 7 att tgt ggt tat aat ttg gct acg ttg gtt atg ctg ggt ccg agt gag      48
Ile Cys Gly Tyr Asn Leu Ala Thr Leu Val Met Leu Gly Pro Ser Glu
1               5                   10                  15 cgg gtg ttt tgt ccg ctt tgt gag cct tgt agt tct gat att tat gag      96
Arg Val Phe Cys Pro Leu Cys Glu Pro Cys Ser Ser Asp Ile Tyr Glu
            20                  25                  30

<210> SEQ ID NO 8
<211> LENGTH: 32
<212> TYPE: PRT
<213> ORGANISM: artificial sequence
<220> FEATURE:
<223> OTHER INFORMATION: Synthetic Construct

<400> SEQUENCE: 8

Ile Cys Gly Tyr Asn Leu Ala Thr Leu Val Met Leu Gly Pro Ser Glu
1               5                   10                  15

Arg Val Phe Cys Pro Leu Cys Glu Pro Cys Ser Ser Asp Ile Tyr Glu
            20                  25                  30

<210> SEQ ID NO 9
<211> LENGTH: 90
<212> TYPE: DNA
<213> ORGANISM: artificial sequence
<220> FEATURE:
<223> OTHER INFORMATION: TRIP-alpha 9-38, fragment of TRIP-alpha
<220> FEATURE:
<221> NAME/KEY: CDS
<222> LOCATION: (1)..(90)

<400> SEQUENCE: 9 att tgt ggt tat aat ttg gct acg ttg gtt atg ctg ggt ccg agt gag      48
Ile Cys Gly Tyr Asn Leu Ala Thr Leu Val Met Leu Gly Pro Ser Glu
1               5                   10                  15 cgg gtg ttt tgt ccg ctt tgt gag cct tgt agt tct gat att                90
Arg Val Phe Cys Pro Leu Cys Glu Pro Cys Ser Ser Asp Ile
            20                  25                  30

<210> SEQ ID NO 10
<211> LENGTH: 30
<212> TYPE: PRT
<213> ORGANISM: artificial sequence
<220> FEATURE:
<223> OTHER INFORMATION: Synthetic Construct

<400> SEQUENCE: 10
```

```
Ile Cys Gly Tyr Asn Leu Ala Thr Leu Val Met Leu Gly Pro Ser Glu
1               5                   10                  15

Arg Val Phe Cys Pro Leu Cys Glu Pro Cys Ser Ser Asp Ile
            20                  25                  30

<210> SEQ ID NO 11
<211> LENGTH: 84
<212> TYPE: DNA
<213> ORGANISM: artificial sequence
<220> FEATURE:
<223> OTHER INFORMATION: TRIP-alpha 9-36, fragment of TRIP-alpha
<220> FEATURE:
<221> NAME/KEY: CDS
<222> LOCATION: (1)..(84)

<400> SEQUENCE: 11 att tgt ggt tat aat ttg gct acg ttg gtt atg ctg ggt ccg agt gag      48
Ile Cys Gly Tyr Asn Leu Ala Thr Leu Val Met Leu Gly Pro Ser Glu
1               5                   10                  15 cgg gtg ttt tgt ccg ctt tgt gag cct tgt agt tct                      84
Arg Val Phe Cys Pro Leu Cys Glu Pro Cys Ser Ser
            20                  25

<210> SEQ ID NO 12
<211> LENGTH: 28
<212> TYPE: PRT
<213> ORGANISM: artificial sequence
<220> FEATURE:
<223> OTHER INFORMATION: Synthetic Construct

<400> SEQUENCE: 12

Ile Cys Gly Tyr Asn Leu Ala Thr Leu Val Met Leu Gly Pro Ser Glu
1               5                   10                  15

Arg Val Phe Cys Pro Leu Cys Glu Pro Cys Ser Ser
            20                  25

<210> SEQ ID NO 13
<211> LENGTH: 78
<212> TYPE: DNA
<213> ORGANISM: artificial sequence
<220> FEATURE:
<223> OTHER INFORMATION: TRIP-alpha 9-34, fragment of TRIP-alpha
<220> FEATURE:
<221> NAME/KEY: CDS
<222> LOCATION: (1)..(78)

<400> SEQUENCE: 13 att tgt ggt tat aat ttg gct acg ttg gtt atg ctg ggt ccg agt gag      48
Ile Cys Gly Tyr Asn Leu Ala Thr Leu Val Met Leu Gly Pro Ser Glu
1               5                   10                  15 cgg gtg ttt tgt ccg ctt tgt gag cct tgt                              78
Arg Val Phe Cys Pro Leu Cys Glu Pro Cys
            20                  25

<210> SEQ ID NO 14
<211> LENGTH: 26
<212> TYPE: PRT
<213> ORGANISM: artificial sequence
<220> FEATURE:
<223> OTHER INFORMATION: Synthetic Construct

<400> SEQUENCE: 14

Ile Cys Gly Tyr Asn Leu Ala Thr Leu Val Met Leu Gly Pro Ser Glu
1               5                   10                  15

Arg Val Phe Cys Pro Leu Cys Glu Pro Cys
            20                  25
```

<210> SEQ ID NO 15
<211> LENGTH: 75
<212> TYPE: DNA
<213> ORGANISM: artificial sequence
<220> FEATURE:
<223> OTHER INFORMATION: TRIP-alpha 9-33, fragment of TRIP-alpha
<220> FEATURE:
<221> NAME/KEY: CDS
<222> LOCATION: (1)..(75)

<400> SEQUENCE: 15

```
att tgt ggt tat aat ttg gct acg ttg gtt atg ctg ggt ccg agt gag      48
Ile Cys Gly Tyr Asn Leu Ala Thr Leu Val Met Leu Gly Pro Ser Glu
1               5                  10                  15 cgg gtg ttt tgt ccg ctt tgt gag cct                                   75
Arg Val Phe Cys Pro Leu Cys Glu Pro
            20                  25
```

<210> SEQ ID NO 16
<211> LENGTH: 25
<212> TYPE: PRT
<213> ORGANISM: artificial sequence
<220> FEATURE:
<223> OTHER INFORMATION: Synthetic Construct

<400> SEQUENCE: 16

```
Ile Cys Gly Tyr Asn Leu Ala Thr Leu Val Met Leu Gly Pro Ser Glu
1               5                  10                  15

Arg Val Phe Cys Pro Leu Cys Glu Pro
            20                  25
```

<210> SEQ ID NO 17
<211> LENGTH: 99
<212> TYPE: DNA
<213> ORGANISM: artificial sequence
<220> FEATURE:
<223> OTHER INFORMATION: TRIP-alpha 1-33, fragment of TRIP-alpha
<220> FEATURE:
<221> NAME/KEY: CDS
<222> LOCATION: (1)..(99)

<400> SEQUENCE: 17

```
gcg agg gag ggg gct gat ggt gcg att tgt ggt tat aat ttg gct acg      48
Ala Arg Glu Gly Ala Asp Gly Ala Ile Cys Gly Tyr Asn Leu Ala Thr
1               5                  10                  15 ttg gtt atg ctg ggt ccg agt gag cgg gtg ttt tgt ccg ctt tgt gag      96
Leu Val Met Leu Gly Pro Ser Glu Arg Val Phe Cys Pro Leu Cys Glu
            20                  25                  30 cct                                                                   99
Pro
```

<210> SEQ ID NO 18
<211> LENGTH: 33
<212> TYPE: PRT
<213> ORGANISM: artificial sequence
<220> FEATURE:
<223> OTHER INFORMATION: Synthetic Construct

<400> SEQUENCE: 18

```
Ala Arg Glu Gly Ala Asp Gly Ala Ile Cys Gly Tyr Asn Leu Ala Thr
1               5                  10                  15

Leu Val Met Leu Gly Pro Ser Glu Arg Val Phe Cys Pro Leu Cys Glu
            20                  25                  30

Pro
```

```
<210> SEQ ID NO 19
<211> LENGTH: 441
<212> TYPE: DNA
<213> ORGANISM: artificial sequence
<220> FEATURE:
<223> OTHER INFORMATION: TRIAP-alpha 9-42, variant of TRIAP-alpha
<220> FEATURE:
<221> NAME/KEY: CDS
<222> LOCATION: (1)..(438)

<400> SEQUENCE: 19 atg agc gat aaa att att cac ctg act gac gac agt ttt gac acg gat        48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg        96
Val Leu Lys Ala Asp Gly Ala Ile Leu Val Asp Phe Trp Ala Glu Trp
                20                  25                  30 tgc ggt ccg att tgt ggt tat aat ttg gct acg ttg gtt atg ctg ggt       144
Cys Gly Pro Ile Cys Gly Tyr Asn Leu Ala Thr Leu Val Met Leu Gly
            35                  40                  45 ccg agt gag cgg gtg ttt tgt ccg ctt tgt gag cct tgt agt tct gat       192
Pro Ser Glu Arg Val Phe Cys Pro Leu Cys Glu Pro Cys Ser Ser Asp
        50                  55                  60 att tat gag ttg atg ggt ccg tgc aaa atg atc gcc ccg att ctg gat       240
Ile Tyr Glu Leu Met Gly Pro Cys Lys Met Ile Ala Pro Ile Leu Asp
65                  70                  75                  80 gaa atc gct gac gaa tat cag ggc aaa ctg acc gtt gca aaa ctg aac       288
Glu Ile Ala Asp Glu Tyr Gln Gly Lys Leu Thr Val Ala Lys Leu Asn
                85                  90                  95 atc gat caa aac cct ggc act gcg ccg aaa tat ggc atc cgt ggt atc       336
Ile Asp Gln Asn Pro Gly Thr Ala Pro Lys Tyr Gly Ile Arg Gly Ile
                100                 105                 110 ccg act ctg ctg ctg ttc aaa aac ggt gaa gtg gcg tcg gca acc aaa       384
Pro Thr Leu Leu Leu Phe Lys Asn Gly Glu Val Ala Ser Ala Thr Lys
            115                 120                 125 gtg ggt gca ctg tct aaa ggt cag ttg aaa gag ttc ctc gac gct aac       432
Val Gly Ala Leu Ser Lys Gly Gln Leu Lys Glu Phe Leu Asp Ala Asn
        130                 135                 140 ctg gcg taa                                                           441
Leu Ala
145

<210> SEQ ID NO 20
<211> LENGTH: 146
<212> TYPE: PRT
<213> ORGANISM: artificial sequence
<220> FEATURE:
<223> OTHER INFORMATION: Synthetic Construct

<400> SEQUENCE: 20

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Thr Leu Val Met Leu Gly
            35                  40                  45

Pro Ser Glu Arg Val Phe Cys Pro Leu Cys Glu Pro Cys Ser Ser Asp
        50                  55                  60

Ile Tyr Glu Leu Met Gly Pro Cys Lys Met Ile Ala Pro Ile Leu Asp
65                  70                  75                  80

Glu Ile Ala Asp Glu Tyr Gln Gly Lys Leu Thr Val Ala Lys Leu Asn
                85                  90                  95
```

```
Ile Asp Gln Asn Pro Gly Thr Ala Pro Lys Tyr Gly Ile Arg Gly Ile
            100                 105                 110
Pro Thr Leu Leu Leu Phe Lys Asn Gly Glu Val Ala Ser Ala Thr Lys
        115                 120                 125
Val Gly Ala Leu Ser Lys Gly Gln Leu Lys Glu Phe Leu Asp Ala Asn
    130                 135                 140
Leu Ala
145

<210> SEQ ID NO 21
<211> LENGTH: 435
<212> TYPE: DNA
<213> ORGANISM: artificial sequence
<220> FEATURE:
<223> OTHER INFORMATION: TRIAP-alpha 9-40, variant of TRIAP-alpha
<220> FEATURE:
<221> NAME/KEY: CDS
<222> LOCATION: (1)..(432)

<400> SEQUENCE: 21 atg agc gat aaa att att cac ctg act gac gac agt ttt gac acg gat         48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg         96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt        144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct tgt agt tct gat        192
Pro Ser Glu Arg Val Phe Cys Pro Leu Cys Glu Pro Cys Ser Ser Asp
    50                  55                  60 att tat gag ggt ccg tgc aaa atg atc gcc ccg att ctg gat gaa atc        240
Ile Tyr Glu Gly Pro Cys Lys Met Ile Ala Pro Ile Leu Asp Glu Ile
65                  70                  75                  80 gct gac gaa tat cag ggc aaa ctg acc gtt gca aaa ctg aac atc gat        288
Ala Asp Glu Tyr Gln Gly Lys Leu Thr Val Ala Lys Leu Asn Ile Asp
                85                  90                  95 caa aac cct ggc act gcg ccg aaa tat ggc atc cgt ggt atc ccg act        336
Gln Asn Pro Gly Thr Ala Pro Lys Tyr Gly Ile Arg Gly Ile Pro Thr
            100                 105                 110 ctg ctg ctg ttc aaa aac ggt gaa gtg gcg tcg gca acc aaa gtg ggt        384
Leu Leu Leu Phe Lys Asn Gly Glu Val Ala Ser Ala Thr Lys Val Gly
        115                 120                 125 gca ctg tct aaa ggt cag ttg aaa gag ttc ctc gac gct aac ctg gcg        432
Ala Leu Ser Lys Gly Gln Leu Lys Glu Phe Leu Asp Ala Asn Leu Ala
    130                 135                 140 taa                                                                    435

<210> SEQ ID NO 22
<211> LENGTH: 144
<212> TYPE: PRT
<213> ORGANISM: artificial sequence
<220> FEATURE:
<223> OTHER INFORMATION: Synthetic Construct

<400> SEQUENCE: 22

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30
```

```
Cys Gly Pro Ile Cys Gly Tyr Asn Leu Ala Thr Leu Val Met Leu Gly
             35                  40                  45

Pro Ser Glu Arg Val Phe Cys Pro Leu Cys Glu Pro Cys Ser Ser Asp
 50                  55                  60

Ile Tyr Glu Gly Pro Cys Lys Met Ile Ala Pro Ile Leu Asp Glu Ile
 65                  70                  75                  80

Ala Asp Glu Tyr Gln Gly Lys Leu Thr Val Ala Lys Leu Asn Ile Asp
                 85                  90                  95

Gln Asn Pro Gly Thr Ala Pro Lys Tyr Gly Ile Arg Gly Ile Pro Thr
                100                 105                 110

Leu Leu Leu Phe Lys Asn Gly Glu Val Ala Ser Ala Thr Lys Val Gly
                115                 120                 125

Ala Leu Ser Lys Gly Gln Leu Lys Glu Phe Leu Asp Ala Asn Leu Ala
        130                 135                 140
```

<210> SEQ ID NO 23
<211> LENGTH: 429
<212> TYPE: DNA
<213> ORGANISM: artificial sequence
<220> FEATURE:
<223> OTHER INFORMATION: TRIAP-alpha 9-38, variant of TRIAP-alpha
<220> FEATURE:
<221> NAME/KEY: CDS
<222> LOCATION: (1)..(426)

<400> SEQUENCE: 23

```
atg agc gat aaa att att cac ctg act gac gac agt ttt gac acg gat     48
Met Ser Asp Lys Ile Ile His Leu Thr Asp Asp Ser Phe Asp Thr Asp
 1               5                  10                  15 gta ctc aaa gcg gac ggg gcg atc ctc gtc gat ttc tgg gca gag tgg     96
Val Leu Lys Ala Asp Gly Ala Ile Leu Val Asp Phe Trp Ala Glu Trp
                 20                  25                  30 tgc ggt ccg att tgt ggt tat aat ttg gct acg ttg gtt atg ctg ggt    144
Cys Gly Pro Ile Cys Gly Tyr Asn Leu Ala Thr Leu Val Met Leu Gly
             35                  40                  45 ccg agt gag cgg gtg ttt tgt ccg ctt tgt gag cct tgt agt tct gat    192
Pro Ser Glu Arg Val Phe Cys Pro Leu Cys Glu Pro Cys Ser Ser Asp
 50                  55                  60 att ggt ccg tgc aaa atg atc gcc ccg att ctg gat gaa atc gct gac    240
Ile Gly Pro Cys Lys Met Ile Ala Pro Ile Leu Asp Glu Ile Ala Asp
 65                  70                  75                  80 gaa tat cag ggc aaa ctg acc gtt gca aaa ctg aac atc gat caa aac    288
Glu Tyr Gln Gly Lys Leu Thr Val Ala Lys Leu Asn Ile Asp Gln Asn
                 85                  90                  95 cct ggc act gcg ccg aaa tat ggc atc cgt ggt atc ccg act ctg ctg    336
Pro Gly Thr Ala Pro Lys Tyr Gly Ile Arg Gly Ile Pro Thr Leu Leu
                100                 105                 110 ctg ttc aaa aac ggt gaa gtg gcg tcg gca acc aaa gtg ggt gca ctg    384
Leu Phe Lys Asn Gly Glu Val Ala Ser Ala Thr Lys Val Gly Ala Leu
                115                 120                 125 tct aaa ggt cag ttg aaa gag ttc ctc gac gct aac ctg gcg taa        429
Ser Lys Gly Gln Leu Lys Glu Phe Leu Asp Ala Asn Leu Ala
        130                 135                 140
```

<210> SEQ ID NO 24
<211> LENGTH: 142
<212> TYPE: PRT
<213> ORGANISM: artificial sequence
<220> FEATURE:
<223> OTHER INFORMATION: Synthetic Construct

<400> SEQUENCE: 24

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
            35                  40                  45

Pro Ser Glu Arg Val Phe Cys Pro Leu Cys Glu Pro Cys Ser Ser Asp
        50                  55                  60

Ile Gly Pro Cys Lys Met Ile Ala Pro Ile Leu Asp Glu Ile Ala Asp
65              70                  75                  80

Glu Tyr Gln Gly Lys Leu Thr Val Ala Lys Leu Asn Ile Asp Gln Asn
                85                  90                  95

Pro Gly Thr Ala Pro Lys Tyr Gly Ile Arg Gly Ile Pro Thr Leu Leu
            100                 105                 110

Leu Phe Lys Asn Gly Glu Val Ala Ser Ala Thr Lys Val Gly Ala Leu
        115                 120                 125

Ser Lys Gly Gln Leu Lys Glu Phe Leu Asp Ala Asn Leu Ala
    130                 135                 140
```

<210> SEQ ID NO 25
<211> LENGTH: 423
<212> TYPE: DNA
<213> ORGANISM: artificial sequence
<220> FEATURE:
<223> OTHER INFORMATION: TRIAP-alpha 9-36, variant of TRIAP-alpha
<220> FEATURE:
<221> NAME/KEY: CDS
<222> LOCATION: (1)..(420)

<400> SEQUENCE: 25

```
atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt      144
Cys Gly Pro Ile Cys Gly Tyr Asn Leu Ala Thr Leu Val Met Leu Gly
            35                  40                  45 ccg agt gag cgg gtg ttt tgt ccg ctt tgt gag cct tgt agt tct ggt      192
Pro Ser Glu Arg Val Phe Cys Pro Leu Cys Glu Pro Cys Ser Ser Gly
        50                  55                  60 ccg tgc aaa atg atc gcc ccg att ctg gat gaa atc gct gac gaa tat      240
Pro Cys Lys Met Ile Ala Pro Ile Leu Asp Glu Ile Ala Asp Glu Tyr
65              70                  75                  80 cag ggc aaa ctg acc gtt gca aaa ctg aac atc gat caa aac cct ggc      288
Gln Gly Lys Leu Thr Val Ala Lys Leu Asn Ile Asp Gln Asn Pro Gly
                85                  90                  95 act gcg ccg aaa tat ggc atc cgt ggt atc ccg act ctg ctg ctg ttc      336
Thr Ala Pro Lys Tyr Gly Ile Arg Gly Ile Pro Thr Leu Leu Leu Phe
            100                 105                 110 aaa aac ggt gaa gtg gcg tcg gca acc aaa gtg ggt gca ctg tct aaa      384
Lys Asn Gly Glu Val Ala Ser Ala Thr Lys Val Gly Ala Leu Ser Lys
        115                 120                 125 ggt cag ttg aaa gag ttc ctc gac gct aac ctg gcg taa                  423
Gly Gln Leu Lys Glu Phe Leu Asp Ala Asn Leu Ala
    130                 135                 140
```

<210> SEQ ID NO 26
<211> LENGTH: 140
<212> TYPE: PRT

<213> ORGANISM: artificial sequence
<220> FEATURE:
<223> OTHER INFORMATION: Synthetic Construct

<400> SEQUENCE: 26

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Cys Ser Ser Gly
    50                  55                  60

Pro Cys Lys Met Ile Ala Pro Ile Leu Asp Glu Ile Ala Asp Glu Tyr
65                  70                  75                  80

Gln Gly Lys Leu Thr Val Ala Lys Leu Asn Ile Asp Gln Asn Pro Gly
                85                  90                  95

Thr Ala Pro Lys Tyr Gly Ile Arg Gly Ile Pro Thr Leu Leu Leu Phe
            100                 105                 110

Lys Asn Gly Glu Val Ala Ser Ala Thr Lys Val Gly Ala Leu Ser Lys
        115                 120                 125

Gly Gln Leu Lys Glu Phe Leu Asp Ala Asn Leu Ala
    130                 135                 140
```

<210> SEQ ID NO 27
<211> LENGTH: 417
<212> TYPE: DNA
<213> ORGANISM: artificial sequence
<220> FEATURE:
<223> OTHER INFORMATION: TRIAP-alpha 9-34, variant of TRIAP-alpha
<220> FEATURE:
<221> NAME/KEY: CDS
<222> LOCATION: (1)..(414)

<400> SEQUENCE: 27

```
atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt     144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct tgt ggt ccg tgc     192
Pro Ser Glu Arg Val Phe Cys Pro Leu Cys Glu Pro Cys Gly Pro Cys
    50                  55                  60 aaa atg atc gcc ccg att ctg gat gaa atc gct gac gaa tat cag ggc     240
Lys Met Ile Ala Pro Ile Leu Asp Glu Ile Ala Asp Glu Tyr Gln Gly
65                  70                  75                  80 aaa ctg acc gtt gca aaa ctg aac atc gat caa aac cct ggc act gcg     288
Lys Leu Thr Val Ala Lys Leu Asn Ile Asp Gln Asn Pro Gly Thr Ala
                85                  90                  95 ccg aaa tat ggc atc cgt ggt atc ccg act ctg ctg ctg ttc aaa aac     336
Pro Lys Tyr Gly Ile Arg Gly Ile Pro Thr Leu Leu Leu Phe Lys Asn
            100                 105                 110 ggt gaa gtg gcg tcg gca acc aaa gtg ggt gca ctg tct aaa ggt cag     384
Gly Glu Val Ala Ser Ala Thr Lys Val Gly Ala Leu Ser Lys Gly Gln
        115                 120                 125 ttg aaa gag ttc ctc gac gct aac ctg gcg taa                         417
Leu Lys Glu Phe Leu Asp Ala Asn Leu Ala
```

-continued

<210> SEQ ID NO 28
<211> LENGTH: 138
<212> TYPE: PRT
<213> ORGANISM: artificial sequence
<220> FEATURE:
<223> OTHER INFORMATION: Synthetic Construct

<400> SEQUENCE: 28

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Gly Pro Cys
    50                  55                  60

Lys Met Ile Ala Pro Ile Leu Asp Glu Ile Ala Asp Glu Tyr Gln Gly
65                  70                  75                  80

Lys Leu Thr Val Ala Lys Leu Asn Ile Asp Gln Asn Pro Gly Thr Ala
                85                  90                  95

Pro Lys Tyr Gly Ile Arg Gly Ile Pro Thr Leu Leu Leu Phe Lys Asn
            100                 105                 110

Gly Glu Val Ala Ser Ala Thr Lys Val Gly Ala Leu Ser Lys Gly Gln
        115                 120                 125

Leu Lys Glu Phe Leu Asp Ala Asn Leu Ala
    130                 135

<210> SEQ ID NO 29
<211> LENGTH: 414
<212> TYPE: DNA
<213> ORGANISM: artificial sequence
<220> FEATURE:
<223> OTHER INFORMATION: TRIAP-alpha 9-33, variant of TRIAP-alpha
<220> FEATURE:
<221> NAME/KEY: CDS
<222> LOCATION: (1)..(411)

<400> SEQUENCE: 29 atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt     144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct ggt ccg tgc aaa     192
Pro Ser Glu Arg Val Phe Cys Pro Leu Cys Glu Pro Gly Pro Cys Lys
    50                  55                  60 atg atc gcc ccg att ctg gat gaa atc gct gac gaa tat cag ggc aaa     240
Met Ile Ala Pro Ile Leu Asp Glu Ile Ala Asp Glu Tyr Gln Gly Lys
65                  70                  75                  80 ctg acc gtt gca aaa ctg aac atc gat caa aac cct ggc act gcg ccg     288
Leu Thr Val Ala Lys Leu Asn Ile Asp Gln Asn Pro Gly Thr Ala Pro
                85                  90                  95 aaa tat ggc atc cgt ggt atc ccg act ctg ctg ctg ttc aaa aac ggt     336
Lys Tyr Gly Ile Arg Gly Ile Pro Thr Leu Leu Leu Phe Lys Asn Gly
            100                 105                 110

```
gaa gtg gcg tcg gca acc aaa gtg ggt gca ctg tct aaa ggt cag ttg      384
Glu Val Ala Ser Ala Thr Lys Val Gly Ala Leu Ser Lys Gly Gln Leu
        115                 120                 125 aaa gag ttc ctc gac gct aac ctg gcg taa                              414
Lys Glu Phe Leu Asp Ala Asn Leu Ala
    130                 135

<210> SEQ ID NO 30
<211> LENGTH: 137
<212> TYPE: PRT
<213> ORGANISM: artificial sequence
<220> FEATURE:
<223> OTHER INFORMATION: Synthetic Construct

<400> SEQUENCE: 30

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Gly Pro Cys Lys
    50                  55                  60

Met Ile Ala Pro Ile Leu Asp Glu Ile Ala Asp Glu Tyr Gln Gly Lys
65                  70                  75                  80

Leu Thr Val Ala Lys Leu Asn Ile Asp Gln Asn Pro Gly Thr Ala Pro
                85                  90                  95

Lys Tyr Gly Ile Arg Gly Ile Pro Thr Leu Leu Leu Phe Lys Asn Gly
            100                 105                 110

Glu Val Ala Ser Ala Thr Lys Val Gly Ala Leu Ser Lys Gly Gln Leu
        115                 120                 125

Lys Glu Phe Leu Asp Ala Asn Leu Ala
    130                 135

<210> SEQ ID NO 31
<211> LENGTH: 438
<212> TYPE: DNA
<213> ORGANISM: artificial sequence
<220> FEATURE:
<223> OTHER INFORMATION: TRIAP-alpha 1-33, variant of TRIAP-alpha
<220> FEATURE:
<221> NAME/KEY: CDS
<222> LOCATION: (1)..(435)

<400> SEQUENCE: 31 atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg gcg agg gag ggg gct gat ggt gcg att tgt ggt tat aat      144
Cys Gly Pro Ala Arg Glu Gly Ala Asp Gly Ala Ile Cys Gly Tyr Asn
        35                  40                  45 ttg gct acg ttg gtt atg ctg ggt ccg agt gag cgg gtg ttt tgt ccg      192
Leu Ala Thr Leu Val Met Leu Gly Pro Ser Glu Arg Val Phe Cys Pro
    50                  55                  60 ctt tgt gag cct ggt ccg tgc aaa atg atc gcc ccg att ctg gat gaa      240
Leu Cys Glu Pro Gly Pro Cys Lys Met Ile Ala Pro Ile Leu Asp Glu
65                  70                  75                  80 atc gct gac gaa tat cag ggc aaa ctg acc gtt gca aaa ctg aac atc      288
Ile Ala Asp Glu Tyr Gln Gly Lys Leu Thr Val Ala Lys Leu Asn Ile
```

```
                              85                  90                  95
gat caa aac cct ggc act gcg ccg aaa tat ggc atc cgt ggt atc ccg        336
Asp Gln Asn Pro Gly Thr Ala Pro Lys Tyr Gly Ile Arg Gly Ile Pro
            100                 105                 110 act ctg ctg ctg ttc aaa aac ggt gaa gtg gcg tcg gca acc aaa gtg        384
Thr Leu Leu Leu Phe Lys Asn Gly Glu Val Ala Ser Ala Thr Lys Val
        115                 120                 125 ggt gca ctg tct aaa ggt cag ttg aaa gag ttc ctc gac gct aac ctg        432
Gly Ala Leu Ser Lys Gly Gln Leu Lys Glu Phe Leu Asp Ala Asn Leu
    130                 135                 140 gcg taa                                                                 438
Ala
145

<210> SEQ ID NO 32
<211> LENGTH: 145
<212> TYPE: PRT
<213> ORGANISM: artificial sequence
<220> FEATURE:
<223> OTHER INFORMATION: Synthetic Construct

<400> SEQUENCE: 32

Met Ser Asp Lys Ile Ile His Leu Thr Asp Asp Ser Phe Asp Thr Asp
1               5                  10                  15

Val Leu Lys Ala Asp Gly Ala Ile Leu Val Asp Phe Trp Ala Glu Trp
            20                  25                  30

Cys Gly Pro Ala Arg Glu Gly Ala Asp Gly Ala Ile Cys Gly Tyr Asn
        35                  40                  45

Leu Ala Thr Leu Val Met Leu Gly Pro Ser Glu Arg Val Phe Cys Pro
    50                  55                  60

Leu Cys Glu Pro Gly Pro Cys Lys Met Ile Ala Pro Ile Leu Asp Glu
65                  70                  75                  80

Ile Ala Asp Glu Tyr Gln Gly Lys Leu Thr Val Ala Lys Leu Asn Ile
                85                  90                  95

Asp Gln Asn Pro Gly Thr Ala Pro Lys Tyr Gly Ile Arg Gly Ile Pro
            100                 105                 110

Thr Leu Leu Leu Phe Lys Asn Gly Glu Val Ala Ser Ala Thr Lys Val
        115                 120                 125

Gly Ala Leu Ser Lys Gly Gln Leu Lys Glu Phe Leu Asp Ala Asn Leu
    130                 135                 140

Ala
145

<210> SEQ ID NO 33
<211> LENGTH: 435
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(432)

<400> SEQUENCE: 33 atg agc gat aaa att att cac ctg act gac gac agt ttt gac acg gat         48
Met Ser Asp Lys Ile Ile His Leu Thr Asp Asp Ser Phe Asp Thr Asp
1               5                  10                  15 gta ctc aaa gcg gac ggg gcg atc ctc gtc gat ttc tgg gca gag tgg         96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt        144
```

```
Cys Gly Pro Ile Cys Gly Tyr Asn Leu Ala Thr Leu Val Met Leu Gly
         35                  40                  45 ccg agt gag cgg gtg ttt tgt ccg ctt tgt gag cct tgt agt tct gat      192
Pro Ser Glu Arg Val Phe Cys Pro Leu Cys Glu Pro Cys Ser Ser Asp
 50                  55                  60 att tat gag ttg atg tgc aaa atg atc gcc ccg att ctg gat gaa atc      240
Ile Tyr Glu Leu Met Cys Lys Met Ile Ala Pro Ile Leu Asp Glu Ile
 65                  70                  75                  80 gct gac gaa tat cag ggc aaa ctg acc gtt gca aaa ctg aac atc gat      288
Ala Asp Glu Tyr Gln Gly Lys Leu Thr Val Ala Lys Leu Asn Ile Asp
                 85                  90                  95 caa aac cct ggc act gcg ccg aaa tat ggc atc cgt ggt atc ccg act      336
Gln Asn Pro Gly Thr Ala Pro Lys Tyr Gly Ile Arg Gly Ile Pro Thr
            100                 105                 110 ctg ctg ctg ttc aaa aac ggt gaa gtg gcg tcg gca acc aaa gtg ggt      384
Leu Leu Leu Phe Lys Asn Gly Glu Val Ala Ser Ala Thr Lys Val Gly
        115                 120                 125 gca ctg tct aaa ggt cag ttg aaa gag ttc ctc gac gct aac ctg gcg      432
Ala Leu Ser Lys Gly Gln Leu Lys Glu Phe Leu Asp Ala Asn Leu Ala
130                 135                 140 taa                                                                  435

<210> SEQ ID NO 34
<211> LENGTH: 144
<212> TYPE: PRT
<213> ORGANISM: artificial sequence
<220> FEATURE:
<223> OTHER INFORMATION: Synthetic Construct

<400> SEQUENCE: 34

Met Ser Asp Lys Ile Ile His Leu Thr Asp Asp Ser Phe Asp Thr Asp
  1               5                  10                  15

Val Leu Lys Ala Asp Gly Ala Ile Leu Val Asp Phe Trp Ala Glu Trp
                 20                  25                  30

Cys Gly Pro Ile Cys Gly Tyr Asn Leu Ala Thr Leu Val Met Leu Gly
             35                  40                  45

Pro Ser Glu Arg Val Phe Cys Pro Leu Cys Glu Pro Cys Ser Ser Asp
 50                  55                  60

Ile Tyr Glu Leu Met Cys Lys Met Ile Ala Pro Ile Leu Asp Glu Ile
 65                  70                  75                  80

Ala Asp Glu Tyr Gln Gly Lys Leu Thr Val Ala Lys Leu Asn Ile Asp
                 85                  90                  95

Gln Asn Pro Gly Thr Ala Pro Lys Tyr Gly Ile Arg Gly Ile Pro Thr
            100                 105                 110

Leu Leu Leu Phe Lys Asn Gly Glu Val Ala Ser Ala Thr Lys Val Gly
        115                 120                 125

Ala Leu Ser Lys Gly Gln Leu Lys Glu Phe Leu Asp Ala Asn Leu Ala
130                 135                 140

<210> SEQ ID NO 35
<211> LENGTH: 429
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(426)

<400> SEQUENCE: 35 atg agc gat aaa att att cac ctg act gac gac agt ttt gac acg gat       48
```

```
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt     144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct tgt agt tct gat     192
Pro Ser Glu Arg Val Phe Cys Pro Leu Cys Glu Pro Cys Ser Ser Asp
    50                  55                  60 att tat gag tgc aaa atg atc gcc ccg att ctg gat gaa atc gct gac     240
Ile Tyr Glu Cys Lys Met Ile Ala Pro Ile Leu Asp Glu Ile Ala Asp
65                  70                  75                  80 gaa tat cag ggc aaa ctg acc gtt gca aaa ctg aac atc gat caa aac     288
Glu Tyr Gln Gly Lys Leu Thr Val Ala Lys Leu Asn Ile Asp Gln Asn
                85                  90                  95 cct ggc act gcg ccg aaa tat ggc atc cgt ggt atc ccg act ctg ctg     336
Pro Gly Thr Ala Pro Lys Tyr Gly Ile Arg Gly Ile Pro Thr Leu Leu
            100                 105                 110 ctg ttc aaa aac ggt gaa gtg gcg tcg gca acc aaa gtg ggt gca ctg     384
Leu Phe Lys Asn Gly Glu Val Ala Ser Ala Thr Lys Val Gly Ala Leu
        115                 120                 125 tct aaa ggt cag ttg aaa gag ttc ctc gac gct aac ctg gcg taa         429
Ser Lys Gly Gln Leu Lys Glu Phe Leu Asp Ala Asn Leu Ala
    130                 135                 140

<210> SEQ ID NO 36
<211> LENGTH: 142
<212> TYPE: PRT
<213> ORGANISM: artificial sequence
<220> FEATURE:
<223> OTHER INFORMATION: Synthetic Construct

<400> SEQUENCE: 36

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Cys Ser Ser Asp
    50                  55                  60

Ile Tyr Glu Cys Lys Met Ile Ala Pro Ile Leu Asp Glu Ile Ala Asp
65                  70                  75                  80

Glu Tyr Gln Gly Lys Leu Thr Val Ala Lys Leu Asn Ile Asp Gln Asn
                85                  90                  95

Pro Gly Thr Ala Pro Lys Tyr Gly Ile Arg Gly Ile Pro Thr Leu Leu
            100                 105                 110

Leu Phe Lys Asn Gly Glu Val Ala Ser Ala Thr Lys Val Gly Ala Leu
        115                 120                 125

Ser Lys Gly Gln Leu Lys Glu Phe Leu Asp Ala Asn Leu Ala
    130                 135                 140

<210> SEQ ID NO 37
<211> LENGTH: 423
<212> TYPE: DNA
<213> ORGANISM: artificial sequence
<220> FEATURE:
<223> OTHER INFORMATION: variant of TRIAP-alpha
<220> FEATURE:
```

```
<221> NAME/KEY: CDS
<222> LOCATION: (1)..(420)

<400> SEQUENCE: 37 atg agc gat aaa att att cac ctg act gac gac agt ttt gac acg gat        48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg        96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt       144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct tgt agt tct gat       192
Pro Ser Glu Arg Val Phe Cys Pro Leu Cys Glu Pro Cys Ser Ser Asp
    50                  55                  60 att tgc aaa atg atc gcc ccg att ctg gat gaa atc gct gac gaa tat       240
Ile Cys Lys Met Ile Ala Pro Ile Leu Asp Glu Ile Ala Asp Glu Tyr
65                  70                  75                  80 cag ggc aaa ctg acc gtt gca aaa ctg aac atc gat caa aac cct ggc       288
Gln Gly Lys Leu Thr Val Ala Lys Leu Asn Ile Asp Gln Asn Pro Gly
                85                  90                  95 act gcg ccg aaa tat ggc atc cgt ggt atc ccg act ctg ctg ctg ttc       336
Thr Ala Pro Lys Tyr Gly Ile Arg Gly Ile Pro Thr Leu Leu Leu Phe
            100                 105                 110 aaa aac ggt gaa gtg gcg tcg gca acc aaa gtg ggt gca ctg tct aaa       384
Lys Asn Gly Glu Val Ala Ser Ala Thr Lys Val Gly Ala Leu Ser Lys
        115                 120                 125 ggt cag ttg aaa gag ttc ctc gac gct aac ctg gcg taa                   423
Gly Gln Leu Lys Glu Phe Leu Asp Ala Asn Leu Ala
    130                 135                 140

<210> SEQ ID NO 38
<211> LENGTH: 140
<212> TYPE: PRT
<213> ORGANISM: artificial sequence
<220> FEATURE:
<223> OTHER INFORMATION: Synthetic Construct

<400> SEQUENCE: 38

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Cys Ser Ser Asp
    50                  55                  60

Ile Cys Lys Met Ile Ala Pro Ile Leu Asp Glu Ile Ala Asp Glu Tyr
65                  70                  75                  80

Gln Gly Lys Leu Thr Val Ala Lys Leu Asn Ile Asp Gln Asn Pro Gly
                85                  90                  95

Thr Ala Pro Lys Tyr Gly Ile Arg Gly Ile Pro Thr Leu Leu Leu Phe
            100                 105                 110

Lys Asn Gly Glu Val Ala Ser Ala Thr Lys Val Gly Ala Leu Ser Lys
        115                 120                 125

Gly Gln Leu Lys Glu Phe Leu Asp Ala Asn Leu Ala
    130                 135                 140

<210> SEQ ID NO 39
```

<211> LENGTH: 417
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(414)

<400> SEQUENCE: 39

```
atg agc gat aaa att att cac ctg act gac gac agt ttt gac acg gat     48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg     96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt    144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct tgt agt tct tgc    192
Pro Ser Glu Arg Val Phe Cys Pro Leu Cys Glu Pro Cys Ser Ser Cys
    50                  55                  60 aaa atg atc gcc ccg att ctg gat gaa atc gct gac gaa tat cag ggc    240
Lys Met Ile Ala Pro Ile Leu Asp Glu Ile Ala Asp Glu Tyr Gln Gly
65                  70                  75                  80 aaa ctg acc gtt gca aaa ctg aac atc gat caa aac cct ggc act gcg    288
Lys Leu Thr Val Ala Lys Leu Asn Ile Asp Gln Asn Pro Gly Thr Ala
                85                  90                  95 ccg aaa tat ggc atc cgt ggt atc ccg act ctg ctg ctg ttc aaa aac    336
Pro Lys Tyr Gly Ile Arg Gly Ile Pro Thr Leu Leu Leu Phe Lys Asn
            100                 105                 110 ggt gaa gtg gcg tcg gca acc aaa gtg ggt gca ctg tct aaa ggt cag    384
Gly Glu Val Ala Ser Ala Thr Lys Val Gly Ala Leu Ser Lys Gly Gln
        115                 120                 125 ttg aaa gag ttc ctc gac gct aac ctg gcg taa                        417
Leu Lys Glu Phe Leu Asp Ala Asn Leu Ala
    130                 135
```

<210> SEQ ID NO 40
<211> LENGTH: 138
<212> TYPE: PRT
<213> ORGANISM: artificial sequence
<220> FEATURE:
<223> OTHER INFORMATION: Synthetic Construct

<400> SEQUENCE: 40

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Cys Ser Ser Cys
    50                  55                  60

Lys Met Ile Ala Pro Ile Leu Asp Glu Ile Ala Asp Glu Tyr Gln Gly
65                  70                  75                  80

Lys Leu Thr Val Ala Lys Leu Asn Ile Asp Gln Asn Pro Gly Thr Ala
                85                  90                  95

Pro Lys Tyr Gly Ile Arg Gly Ile Pro Thr Leu Leu Leu Phe Lys Asn
            100                 105                 110

Gly Glu Val Ala Ser Ala Thr Lys Val Gly Ala Leu Ser Lys Gly Gln
        115                 120                 125
```

```
Leu Lys Glu Phe Leu Asp Ala Asn Leu Ala
    130                 135
```

<210> SEQ ID NO 41
<211> LENGTH: 411
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(408)

<400> SEQUENCE: 41

```
atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
                20                  25                  30 tgc ggt ccg att tgt ggt tat aat ttg gct acg ttg gtt atg ctg ggt     144
Cys Gly Pro Ile Cys Gly Tyr Asn Leu Ala Thr Leu Val Met Leu Gly
            35                  40                  45 ccg agt gag cgg gtg ttt tgt ccg ctt tgt gag cct tgt tgc aaa atg     192
Pro Ser Glu Arg Val Phe Cys Pro Leu Cys Glu Pro Cys Cys Lys Met
        50                  55                  60 atc gcc ccg att ctg gat gaa atc gct gac gaa tat cag ggc aaa ctg     240
Ile Ala Pro Ile Leu Asp Glu Ile Ala Asp Glu Tyr Gln Gly Lys Leu
65                  70                  75                  80 acc gtt gca aaa ctg aac atc gat caa aac cct ggc act gcg ccg aaa     288
Thr Val Ala Lys Leu Asn Ile Asp Gln Asn Pro Gly Thr Ala Pro Lys
                85                  90                  95 tat ggc atc cgt ggt atc ccg act ctg ctg ctg ttc aaa aac ggt gaa     336
Tyr Gly Ile Arg Gly Ile Pro Thr Leu Leu Leu Phe Lys Asn Gly Glu
            100                 105                 110 gtg gcg tcg gca acc aaa gtg ggt gca ctg tct aaa ggt cag ttg aaa     384
Val Ala Ser Ala Thr Lys Val Gly Ala Leu Ser Lys Gly Gln Leu Lys
        115                 120                 125 gag ttc ctc gac gct aac ctg gcg taa                                 411
Glu Phe Leu Asp Ala Asn Leu Ala
    130                 135
```

<210> SEQ ID NO 42
<211> LENGTH: 136
<212> TYPE: PRT
<213> ORGANISM: artificial sequence
<220> FEATURE:
<223> OTHER INFORMATION: Synthetic Construct

<400> SEQUENCE: 42

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Ile Cys Gly Tyr Asn Leu Ala Thr Leu Val Met Leu Gly
            35                  40                  45

Pro Ser Glu Arg Val Phe Cys Pro Leu Cys Glu Pro Cys Cys Lys Met
        50                  55                  60

Ile Ala Pro Ile Leu Asp Glu Ile Ala Asp Glu Tyr Gln Gly Lys Leu
65                  70                  75                  80

Thr Val Ala Lys Leu Asn Ile Asp Gln Asn Pro Gly Thr Ala Pro Lys
                85                  90                  95
```

```
Tyr Gly Ile Arg Gly Ile Pro Thr Leu Leu Leu Phe Lys Asn Gly Glu
            100                 105                 110

Val Ala Ser Ala Thr Lys Val Gly Ala Leu Ser Lys Gly Gln Leu Lys
        115                 120                 125

Glu Phe Leu Asp Ala Asn Leu Ala
    130                 135

<210> SEQ ID NO 43
<211> LENGTH: 408
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(405)

<400> SEQUENCE: 43 atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg att tgt ggt tat aat ttg gct acg ttg gtt atg ctg ggt     144
Cys Gly Pro Ile Cys Gly Tyr Asn Leu Ala Thr Leu Val Met Leu Gly
        35                  40                  45 ccg agt gag cgg gtg ttt tgt ccg ctt tgt gag cct tgc aaa atg atc     192
Pro Ser Glu Arg Val Phe Cys Pro Leu Cys Glu Pro Cys Lys Met Ile
    50                  55                  60 gcc ccg att ctg gat gaa atc gct gac gaa tat cag ggc aaa ctg acc     240
Ala Pro Ile Leu Asp Glu Ile Ala Asp Glu Tyr Gln Gly Lys Leu Thr
65                  70                  75                  80 gtt gca aaa ctg aac atc gat caa aac cct ggc act gcg ccg aaa tat     288
Val Ala Lys Leu Asn Ile Asp Gln Asn Pro Gly Thr Ala Pro Lys Tyr
                85                  90                  95 ggc atc cgt ggt atc ccg act ctg ctg ctg ttc aaa aac ggt gaa gtg     336
Gly Ile Arg Gly Ile Pro Thr Leu Leu Leu Phe Lys Asn Gly Glu Val
            100                 105                 110 gcg tcg gca acc aaa gtg ggt gca ctg tct aaa ggt cag ttg aaa gag     384
Ala Ser Ala Thr Lys Val Gly Ala Leu Ser Lys Gly Gln Leu Lys Glu
        115                 120                 125 ttc ctc gac gct aac ctg gcg taa                                      408
Phe Leu Asp Ala Asn Leu Ala
    130                 135

<210> SEQ ID NO 44
<211> LENGTH: 135
<212> TYPE: PRT
<213> ORGANISM: artificial sequence
<220> FEATURE:
<223> OTHER INFORMATION: Synthetic Construct

<400> SEQUENCE: 44

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Ile Cys Gly Tyr Asn Leu Ala Thr Leu Val Met Leu Gly
        35                  40                  45

Pro Ser Glu Arg Val Phe Cys Pro Leu Cys Glu Pro Cys Lys Met Ile
    50                  55                  60
```

```
Ala Pro Ile Leu Asp Glu Ile Ala Asp Glu Tyr Gln Gly Lys Leu Thr
65                  70                  75                  80

Val Ala Lys Leu Asn Ile Asp Gln Asn Pro Gly Thr Ala Pro Lys Tyr
                85                  90                  95

Gly Ile Arg Gly Ile Pro Thr Leu Leu Leu Phe Lys Asn Gly Glu Val
            100                 105                 110

Ala Ser Ala Thr Lys Val Gly Ala Leu Ser Lys Gly Gln Leu Lys Glu
        115                 120                 125

Phe Leu Asp Ala Asn Leu Ala
    130                 135

<210> SEQ ID NO 45
<211> LENGTH: 432
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(429)

<400> SEQUENCE: 45 atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc ggt ccg gcg agg gag ggg gct gat ggt gcg att tgt ggt tat aat     144
Cys Gly Pro Ala Arg Glu Gly Ala Asp Gly Ala Ile Cys Gly Tyr Asn
        35                  40                  45 ttg gct acg ttg gtt atg ctg ggt ccg agt gag cgg gtg ttt tgt ccg     192
Leu Ala Thr Leu Val Met Leu Gly Pro Ser Glu Arg Val Phe Cys Pro
    50                  55                  60 ctt tgt gag cct tgc aaa atg atc gcc ccg att ctg gat gaa atc gct     240
Leu Cys Glu Pro Cys Lys Met Ile Ala Pro Ile Leu Asp Glu Ile Ala
65                  70                  75                  80 gac gaa tat cag ggc aaa ctg acc gtt gca aaa ctg aac atc gat caa     288
Asp Glu Tyr Gln Gly Lys Leu Thr Val Ala Lys Leu Asn Ile Asp Gln
                85                  90                  95 aac cct ggc act gcg ccg aaa tat ggc atc cgt ggt atc ccg act ctg     336
Asn Pro Gly Thr Ala Pro Lys Tyr Gly Ile Arg Gly Ile Pro Thr Leu
            100                 105                 110 ctg ctg ttc aaa aac ggt gaa gtg gcg tcg gca acc aaa gtg ggt gca     384
Leu Leu Phe Lys Asn Gly Glu Val Ala Ser Ala Thr Lys Val Gly Ala
        115                 120                 125 ctg tct aaa ggt cag ttg aaa gag ttc ctc gac gct aac ctg gcg taa     432
Leu Ser Lys Gly Gln Leu Lys Glu Phe Leu Asp Ala Asn Leu Ala
    130                 135                 140

<210> SEQ ID NO 46
<211> LENGTH: 143
<212> TYPE: PRT
<213> ORGANISM: artificial sequence
<220> FEATURE:
<223> OTHER INFORMATION: Synthetic Construct

<400> SEQUENCE: 46

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30
```

```
Cys Gly Pro Ala Arg Glu Gly Ala Asp Gly Ala Ile Cys Gly Tyr Asn
         35                  40                  45

Leu Ala Thr Leu Val Met Leu Gly Pro Ser Glu Arg Val Phe Cys Pro
 50                  55                  60

Leu Cys Glu Pro Cys Lys Met Ile Ala Pro Ile Leu Asp Glu Ile Ala
 65                  70                  75                  80

Asp Glu Tyr Gln Gly Lys Leu Thr Val Ala Lys Leu Asn Ile Asp Gln
                 85                  90                  95

Asn Pro Gly Thr Ala Pro Lys Tyr Gly Ile Arg Gly Ile Pro Thr Leu
             100                 105                 110

Leu Leu Phe Lys Asn Gly Glu Val Ala Ser Ala Thr Lys Val Gly Ala
         115                 120                 125

Leu Ser Lys Gly Gln Leu Lys Glu Phe Leu Asp Ala Asn Leu Ala
     130                 135                 140

<210> SEQ ID NO 47
<211> LENGTH: 435
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(432)

<400> SEQUENCE: 47 atg agc gat aaa att att cac ctg act gac gac agt ttt gac acg gat      48
Met Ser Asp Lys Ile Ile His Leu Thr Asp Asp Ser Phe Asp Thr Asp
 1               5                  10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
             20                  25                  30 tgc att tgt ggt tat aat ttg gct acg ttg gtt atg ctg ggt ccg agt     144
Cys Ile Cys Gly Tyr Asn Leu Ala Thr Leu Val Met Leu Gly Pro Ser
         35                  40                  45 gag cgg gtg ttt tgt ccg ctt tgt gag cct tgt agt tct gat att tat     192
Glu Arg Val Phe Cys Pro Leu Cys Glu Pro Cys Ser Ser Asp Ile Tyr
 50                  55                  60 gag ttg atg ggt ccg tgc aaa atg atc gcc ccg att ctg gat gaa atc     240
Glu Leu Met Gly Pro Cys Lys Met Ile Ala Pro Ile Leu Asp Glu Ile
 65                  70                  75                  80 gct gac gaa tat cag ggc aaa ctg acc gtt gca aaa ctg aac atc gat     288
Ala Asp Glu Tyr Gln Gly Lys Leu Thr Val Ala Lys Leu Asn Ile Asp
                 85                  90                  95 caa aac cct ggc act gcg ccg aaa tat ggc atc cgt ggt atc ccg act     336
Gln Asn Pro Gly Thr Ala Pro Lys Tyr Gly Ile Arg Gly Ile Pro Thr
             100                 105                 110 ctg ctg ctg ttc aaa aac ggt gaa gtg gcg tcg gca acc aaa gtg ggt     384
Leu Leu Leu Phe Lys Asn Gly Glu Val Ala Ser Ala Thr Lys Val Gly
         115                 120                 125 gca ctg tct aaa ggt cag ttg aaa gag ttc ctc gac gct aac ctg gcg     432
Ala Leu Ser Lys Gly Gln Leu Lys Glu Phe Leu Asp Ala Asn Leu Ala
     130                 135                 140 taa                                                                  435

<210> SEQ ID NO 48
<211> LENGTH: 144
<212> TYPE: PRT
<213> ORGANISM: artificial sequence
<220> FEATURE:
<223> OTHER INFORMATION: Synthetic Construct
```

<400> SEQUENCE: 48

| Met | Ser | Asp | Lys | Ile | Ile | His | Leu | Thr | Asp | Asp | Ser | Phe | Asp | Thr | Asp |
|---|---|---|---|---|---|---|---|---|---|---|---|---|---|---|---|
| 1 | | | | 5 | | | | | 10 | | | | | 15 | |

| Val | Leu | Lys | Ala | Asp | Gly | Ala | Ile | Leu | Val | Asp | Phe | Trp | Ala | Glu | Trp |
|---|---|---|---|---|---|---|---|---|---|---|---|---|---|---|---|
| | | | 20 | | | | | 25 | | | | | 30 | | |

| Cys | Ile | Cys | Gly | Tyr | Asn | Leu | Ala | Thr | Leu | Val | Met | Leu | Gly | Pro | Ser |
|---|---|---|---|---|---|---|---|---|---|---|---|---|---|---|---|
| | | 35 | | | | | 40 | | | | | 45 | | | |

| Glu | Arg | Val | Phe | Cys | Pro | Leu | Cys | Glu | Pro | Cys | Ser | Ser | Asp | Ile | Tyr |
|---|---|---|---|---|---|---|---|---|---|---|---|---|---|---|---|
| | 50 | | | | | 55 | | | | | 60 | | | | |

| Glu | Leu | Met | Gly | Pro | Cys | Lys | Met | Ile | Ala | Pro | Ile | Leu | Asp | Glu | Ile |
|---|---|---|---|---|---|---|---|---|---|---|---|---|---|---|---|
| 65 | | | | | 70 | | | | | 75 | | | | | 80 |

| Ala | Asp | Glu | Tyr | Gln | Gly | Lys | Leu | Thr | Val | Ala | Lys | Leu | Asn | Ile | Asp |
|---|---|---|---|---|---|---|---|---|---|---|---|---|---|---|---|
| | | | | 85 | | | | | 90 | | | | | 95 | |

| Gln | Asn | Pro | Gly | Thr | Ala | Pro | Lys | Tyr | Gly | Ile | Arg | Gly | Ile | Pro | Thr |
|---|---|---|---|---|---|---|---|---|---|---|---|---|---|---|---|
| | | | 100 | | | | | 105 | | | | | 110 | | |

| Leu | Leu | Leu | Phe | Lys | Asn | Gly | Glu | Val | Ala | Ser | Ala | Thr | Lys | Val | Gly |
|---|---|---|---|---|---|---|---|---|---|---|---|---|---|---|---|
| | | 115 | | | | | 120 | | | | | 125 | | | |

| Ala | Leu | Ser | Lys | Gly | Gln | Leu | Lys | Glu | Phe | Leu | Asp | Ala | Asn | Leu | Ala |
|---|---|---|---|---|---|---|---|---|---|---|---|---|---|---|---|
| | 130 | | | | | 135 | | | | | 140 | | | | |

<210> SEQ ID NO 49
<211> LENGTH: 429
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(426)

<400> SEQUENCE: 49

| atg | agc | gat | aaa | att | att | cac | ctg | act | gac | gac | agt | ttt | gac | acg | gat | 48 |
|---|---|---|---|---|---|---|---|---|---|---|---|---|---|---|---|---|
| Met | Ser | Asp | Lys | Ile | Ile | His | Leu | Thr | Asp | Asp | Ser | Phe | Asp | Thr | Asp | |
| 1 | | | | 5 | | | | | 10 | | | | | 15 | | |

| gta | ctc | aaa | gcg | gac | ggg | gcg | atc | ctc | gtc | gat | ttc | tgg | gca | gag | tgg | 96 |
|---|---|---|---|---|---|---|---|---|---|---|---|---|---|---|---|---|
| Val | Leu | Lys | Ala | Asp | Gly | Ala | Ile | Leu | Val | Asp | Phe | Trp | Ala | Glu | Trp | |
| | | | 20 | | | | | 25 | | | | | 30 | | | |

| tgc | att | tgt | ggt | tat | aat | ttg | gct | acg | ttg | gtt | atg | ctg | ggt | ccg | agt | 144 |
|---|---|---|---|---|---|---|---|---|---|---|---|---|---|---|---|---|
| Cys | Ile | Cys | Gly | Tyr | Asn | Leu | Ala | Thr | Leu | Val | Met | Leu | Gly | Pro | Ser | |
| | | 35 | | | | | 40 | | | | | 45 | | | | |

| gag | cgg | gtg | ttt | tgt | ccg | ctt | tgt | gag | cct | tgt | agt | tct | gat | att | tat | 192 |
|---|---|---|---|---|---|---|---|---|---|---|---|---|---|---|---|---|
| Glu | Arg | Val | Phe | Cys | Pro | Leu | Cys | Glu | Pro | Cys | Ser | Ser | Asp | Ile | Tyr | |
| | 50 | | | | | 55 | | | | | 60 | | | | | |

| gag | ggt | ccg | tgc | aaa | atg | atc | gcc | ccg | att | ctg | gat | gaa | atc | gct | gac | 240 |
|---|---|---|---|---|---|---|---|---|---|---|---|---|---|---|---|---|
| Glu | Gly | Pro | Cys | Lys | Met | Ile | Ala | Pro | Ile | Leu | Asp | Glu | Ile | Ala | Asp | |
| 65 | | | | | 70 | | | | | 75 | | | | | 80 | |

| gaa | tat | cag | ggc | aaa | ctg | acc | gtt | gca | aaa | ctg | aac | atc | gat | caa | aac | 288 |
|---|---|---|---|---|---|---|---|---|---|---|---|---|---|---|---|---|
| Glu | Tyr | Gln | Gly | Lys | Leu | Thr | Val | Ala | Lys | Leu | Asn | Ile | Asp | Gln | Asn | |
| | | | | 85 | | | | | 90 | | | | | 95 | | |

| cct | ggc | act | gcg | ccg | aaa | tat | ggc | atc | cgt | ggt | atc | ccg | act | ctg | ctg | 336 |
|---|---|---|---|---|---|---|---|---|---|---|---|---|---|---|---|---|
| Pro | Gly | Thr | Ala | Pro | Lys | Tyr | Gly | Ile | Arg | Gly | Ile | Pro | Thr | Leu | Leu | |
| | | | 100 | | | | | 105 | | | | | 110 | | | |

| ctg | ttc | aaa | aac | ggt | gaa | gtg | gcg | tcg | gca | acc | aaa | gtg | ggt | gca | ctg | 384 |
|---|---|---|---|---|---|---|---|---|---|---|---|---|---|---|---|---|
| Leu | Phe | Lys | Asn | Gly | Glu | Val | Ala | Ser | Ala | Thr | Lys | Val | Gly | Ala | Leu | |
| | | 115 | | | | | 120 | | | | | 125 | | | | |

| tct | aaa | ggt | cag | ttg | aaa | gag | ttc | ctc | gac | gct | aac | ctg | gcg | taa | | 429 |
|---|---|---|---|---|---|---|---|---|---|---|---|---|---|---|---|---|
| Ser | Lys | Gly | Gln | Leu | Lys | Glu | Phe | Leu | Asp | Ala | Asn | Leu | Ala | | | |
| | 130 | | | | | 135 | | | | | 140 | | | | | |

-continued

```
<210> SEQ ID NO 50
<211> LENGTH: 142
<212> TYPE: PRT
<213> ORGANISM: artificial sequence
<220> FEATURE:
<223> OTHER INFORMATION: Synthetic Construct

<400> SEQUENCE: 50

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Ile Cys Gly Tyr Asn Leu Ala Thr Leu Val Met Leu Gly Pro Ser
            35                  40                  45

Glu Arg Val Phe Cys Pro Leu Cys Glu Pro Cys Ser Ser Asp Ile Tyr
        50                  55                  60

Glu Gly Pro Cys Lys Met Ile Ala Pro Ile Leu Asp Glu Ile Ala Asp
65                  70                  75                  80

Glu Tyr Gln Gly Lys Leu Thr Val Ala Lys Leu Asn Ile Asp Gln Asn
                85                  90                  95

Pro Gly Thr Ala Pro Lys Tyr Gly Ile Arg Gly Ile Pro Thr Leu Leu
            100                 105                 110

Leu Phe Lys Asn Gly Glu Val Ala Ser Ala Thr Lys Val Gly Ala Leu
        115                 120                 125

Ser Lys Gly Gln Leu Lys Glu Phe Leu Asp Ala Asn Leu Ala
130                 135                 140

<210> SEQ ID NO 51
<211> LENGTH: 423
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(420)

<400> SEQUENCE: 51 atg agc gat aaa att att cac ctg act gac gac agt ttt gac acg gat    48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg    96
Val Leu Lys Ala Asp Gly Ala Ile Leu Val Asp Phe Trp Ala Glu Trp
                20                  25                  30 tgc att tgt ggt tat aat ttg gct acg ttg gtt atg ctg ggt ccg agt   144
Cys Ile Cys Gly Tyr Asn Leu Ala Thr Leu Val Met Leu Gly Pro Ser
            35                  40                  45 gag cgg gtg ttt tgt ccg ctt tgt gag cct tgt agt tct gat att ggt   192
Glu Arg Val Phe Cys Pro Leu Cys Glu Pro Cys Ser Ser Asp Ile Gly
        50                  55                  60 ccg tgc aaa atg atc gcc ccg att ctg gat gaa atc gct gac gaa tat   240
Pro Cys Lys Met Ile Ala Pro Ile Leu Asp Glu Ile Ala Asp Glu Tyr
65                  70                  75                  80 cag ggc aaa ctg acc gtt gca aaa ctg aac atc gat caa aac cct ggc   288
Gln Gly Lys Leu Thr Val Ala Lys Leu Asn Ile Asp Gln Asn Pro Gly
                85                  90                  95 act gcg ccg aaa tat ggc atc cgt ggt atc ccg act ctg ctg ctg ttc   336
Thr Ala Pro Lys Tyr Gly Ile Arg Gly Ile Pro Thr Leu Leu Leu Phe
            100                 105                 110 aaa aac ggt gaa gtg gcg tcg gca acc aaa gtg ggt gca ctg tct aaa   384
Lys Asn Gly Glu Val Ala Ser Ala Thr Lys Val Gly Ala Leu Ser Lys
        115                 120                 125
```

```
ggt cag ttg aaa gag ttc ctc gac gct aac ctg gcg taa              423
Gly Gln Leu Lys Glu Phe Leu Asp Ala Asn Leu Ala
    130                 135                 140

<210> SEQ ID NO 52
<211> LENGTH: 140
<212> TYPE: PRT
<213> ORGANISM: artificial sequence
<220> FEATURE:
<223> OTHER INFORMATION: Synthetic Construct

<400> SEQUENCE: 52

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Ile Cys Gly Tyr Asn Leu Ala Thr Leu Val Met Leu Gly Pro Ser
        35                  40                  45

Glu Arg Val Phe Cys Pro Leu Cys Glu Pro Cys Ser Ser Asp Ile Gly
    50                  55                  60

Pro Cys Lys Met Ile Ala Pro Ile Leu Asp Glu Ile Ala Asp Glu Tyr
65                  70                  75                  80

Gln Gly Lys Leu Thr Val Ala Lys Leu Asn Ile Asp Gln Asn Pro Gly
                85                  90                  95

Thr Ala Pro Lys Tyr Gly Ile Arg Gly Ile Pro Thr Leu Leu Leu Phe
            100                 105                 110

Lys Asn Gly Glu Val Ala Ser Ala Thr Lys Val Gly Ala Leu Ser Lys
        115                 120                 125

Gly Gln Leu Lys Glu Phe Leu Asp Ala Asn Leu Ala
    130                 135                 140

<210> SEQ ID NO 53
<211> LENGTH: 417
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(414)

<400> SEQUENCE: 53 atg agc gat aaa att att cac ctg act gac gac agt ttt gac acg gat   48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg   96
Val Leu Lys Ala Asp Gly Ala Ile Leu Val Asp Phe Trp Ala Glu Trp
            20                  25                  30 tgc att tgt ggt tat aat ttg gct acg ttg gtt atg ctg ggt ccg agt  144
Cys Ile Cys Gly Tyr Asn Leu Ala Thr Leu Val Met Leu Gly Pro Ser
        35                  40                  45 gag cgg gtg ttt tgt ccg ctt tgt gag cct tgt agt tct ggt ccg tgc  192
Glu Arg Val Phe Cys Pro Leu Cys Glu Pro Cys Ser Ser Gly Pro Cys
    50                  55                  60 aaa atg atc gcc ccg att ctg gat gaa atc gct gac gaa tat cag ggc  240
Lys Met Ile Ala Pro Ile Leu Asp Glu Ile Ala Asp Glu Tyr Gln Gly
65                  70                  75                  80 aaa ctg acc gtt gca aaa ctg aac atc gat caa aac cct ggc act gcg  288
Lys Leu Thr Val Ala Lys Leu Asn Ile Asp Gln Asn Pro Gly Thr Ala
                85                  90                  95 ccg aaa tat ggc atc cgt ggt atc ccg act ctg ctg ctg ttc aaa aac  336
Pro Lys Tyr Gly Ile Arg Gly Ile Pro Thr Leu Leu Leu Phe Lys Asn
```

```
                                                  -continued

Pro Lys Tyr Gly Ile Arg Gly Ile Pro Thr Leu Leu Leu Phe Lys Asn
            100                 105                 110 ggt gaa gtg gcg tcg gca acc aaa gtg ggt gca ctg tct aaa ggt cag      384
Gly Glu Val Ala Ser Ala Thr Lys Val Gly Ala Leu Ser Lys Gly Gln
            115                 120                 125 ttg aaa gag ttc ctc gac gct aac ctg gcg taa                          417
Leu Lys Glu Phe Leu Asp Ala Asn Leu Ala
            130                 135

<210> SEQ ID NO 54
<211> LENGTH: 138
<212> TYPE: PRT
<213> ORGANISM: artificial sequence
<220> FEATURE:
<223> OTHER INFORMATION: Synthetic Construct

<400> SEQUENCE: 54

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Ile Cys Gly Tyr Asn Leu Ala Thr Leu Val Met Leu Gly Pro Ser
        35                  40                  45

Glu Arg Val Phe Cys Pro Leu Cys Glu Pro Cys Ser Ser Gly Pro Cys
    50                  55                  60

Lys Met Ile Ala Pro Ile Leu Asp Glu Ile Ala Asp Glu Tyr Gln Gly
65                  70                  75                  80

Lys Leu Thr Val Ala Lys Leu Asn Ile Asp Gln Asn Pro Gly Thr Ala
                85                  90                  95

Pro Lys Tyr Gly Ile Arg Gly Ile Pro Thr Leu Leu Leu Phe Lys Asn
            100                 105                 110

Gly Glu Val Ala Ser Ala Thr Lys Val Gly Ala Leu Ser Lys Gly Gln
            115                 120                 125

Leu Lys Glu Phe Leu Asp Ala Asn Leu Ala
            130                 135

<210> SEQ ID NO 55
<211> LENGTH: 411
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(408)

<400> SEQUENCE: 55 atg agc gat aaa att att cac ctg act gac gac agt ttt gac acg gat      48
Met Ser Asp Lys Ile Ile His Leu Thr Asp Asp Ser Phe Asp Thr Asp
1               5                   10                  15 gta ctc aaa gcg gac ggg gcg atc ctc gtc gat ttc tgg gca gag tgg      96
Val Leu Lys Ala Asp Gly Ala Ile Leu Val Asp Phe Trp Ala Glu Trp
            20                  25                  30 tgc att tgt ggt tat aat ttg gct acg ttg gtt atg ctg ggt ccg agt     144
Cys Ile Cys Gly Tyr Asn Leu Ala Thr Leu Val Met Leu Gly Pro Ser
        35                  40                  45 gag cgg gtg ttt tgt ccg ctt tgt gag cct tgt ggt ccg tgc aaa atg     192
Glu Arg Val Phe Cys Pro Leu Cys Glu Pro Cys Gly Pro Cys Lys Met
    50                  55                  60 atc gcc ccg att ctg gat gaa atc gct gac gaa tat cag ggc aaa ctg     240
Ile Ala Pro Ile Leu Asp Glu Ile Ala Asp Glu Tyr Gln Gly Lys Leu
65                  70                  75                  80
```

| | |
|---|---|
| acc gtt gca aaa ctg aac atc gat caa aac cct ggc act gcg ccg aaa<br>Thr Val Ala Lys Leu Asn Ile Asp Gln Asn Pro Gly Thr Ala Pro Lys<br>              85                  90                  95 | 288 |
| tat ggc atc cgt ggt atc ccg act ctg ctg ctg ttc aaa aac ggt gaa<br>Tyr Gly Ile Arg Gly Ile Pro Thr Leu Leu Leu Phe Lys Asn Gly Glu<br>            100                  105                  110 | 336 |
| gtg gcg tcg gca acc aaa gtg ggt gca ctg tct aaa ggt cag ttg aaa<br>Val Ala Ser Ala Thr Lys Val Gly Ala Leu Ser Lys Gly Gln Leu Lys<br>            115                  120                  125 | 384 |
| gag ttc ctc gac gct aac ctg gcg taa<br>Glu Phe Leu Asp Ala Asn Leu Ala<br>            130                  135 | 411 |

<210> SEQ ID NO 56
<211> LENGTH: 136
<212> TYPE: PRT
<213> ORGANISM: artificial sequence
<220> FEATURE:
<223> OTHER INFORMATION: Synthetic Construct

<400> SEQUENCE: 56

Met Ser Asp Lys Ile Ile His Leu Thr Asp Asp Ser Phe Asp Thr Asp
1                 5                    10                   15

Val Leu Lys Ala Asp Gly Ala Ile Leu Val Asp Phe Trp Ala Glu Trp
              20                   25                  30

Cys Ile Cys Gly Tyr Asn Leu Ala Thr Leu Val Met Leu Gly Pro Ser
        35                   40                  45

Glu Arg Val Phe Cys Pro Leu Cys Glu Pro Cys Gly Pro Cys Lys Met
  50                   55                  60

Ile Ala Pro Ile Leu Asp Glu Ile Ala Asp Glu Tyr Gln Gly Lys Leu
65                70                   75                  80

Thr Val Ala Lys Leu Asn Ile Asp Gln Asn Pro Gly Thr Ala Pro Lys
              85                  90                  95

Tyr Gly Ile Arg Gly Ile Pro Thr Leu Leu Leu Phe Lys Asn Gly Glu
        100                  105                  110

Val Ala Ser Ala Thr Lys Val Gly Ala Leu Ser Lys Gly Gln Leu Lys
            115                  120                  125

Glu Phe Leu Asp Ala Asn Leu Ala
        130                  135

<210> SEQ ID NO 57
<211> LENGTH: 408
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(405)

<400> SEQUENCE: 57

| | |
|---|---|
| atg agc gat aaa att att cac ctg act gac gac agt ttt gac acg gat<br>Met Ser Asp Lys Ile Ile His Leu Thr Asp Asp Ser Phe Asp Thr Asp<br>1                 5                    10                   15 | 48 |
| gta ctc aaa gcg gac ggg gcg atc ctc gtc gat ttc tgg gca gag tgg<br>Val Leu Lys Ala Asp Gly Ala Ile Leu Val Asp Phe Trp Ala Glu Trp<br>              20                   25                  30 | 96 |
| tgc att tgt ggt tat aat ttg gct acg ttg gtt atg ctg ggt ccg agt<br>Cys Ile Cys Gly Tyr Asn Leu Ala Thr Leu Val Met Leu Gly Pro Ser<br>        35                   40                  45 | 144 |
| gag cgg gtg ttt tgt ccg ctt tgt gag cct ggt ccg tgc aaa atg atc | 192 |

-continued

```
Glu Arg Val Phe Cys Pro Leu Cys Glu Pro Gly Pro Cys Lys Met Ile
 50                  55                  60 gcc ccg att ctg gat gaa atc gct gac gaa tat cag ggc aaa ctg acc    240
Ala Pro Ile Leu Asp Glu Ile Ala Asp Glu Tyr Gln Gly Lys Leu Thr
 65                  70                  75                  80 gtt gca aaa ctg aac atc gat caa aac cct ggc act gcg ccg aaa tat    288
Val Ala Lys Leu Asn Ile Asp Gln Asn Pro Gly Thr Ala Pro Lys Tyr
                 85                  90                  95 ggc atc cgt ggt atc ccg act ctg ctg ctg ttc aaa aac ggt gaa gtg    336
Gly Ile Arg Gly Ile Pro Thr Leu Leu Leu Phe Lys Asn Gly Glu Val
            100                 105                 110 gcg tcg gca acc aaa gtg ggt gca ctg tct aaa ggt cag ttg aaa gag    384
Ala Ser Ala Thr Lys Val Gly Ala Leu Ser Lys Gly Gln Leu Lys Glu
        115                 120                 125 ttc ctc gac gct aac ctg gcg taa                                    408
Phe Leu Asp Ala Asn Leu Ala
    130                 135

<210> SEQ ID NO 58
<211> LENGTH: 135
<212> TYPE: PRT
<213> ORGANISM: artificial sequence
<220> FEATURE:
<223> OTHER INFORMATION: Synthetic Construct

<400> SEQUENCE: 58

Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                20                  25                  30

Cys Ile Cys Gly Tyr Asn Leu Ala Thr Leu Val Met Leu Gly Pro Ser
            35                  40                  45

Glu Arg Val Phe Cys Pro Leu Cys Glu Pro Gly Pro Cys Lys Met Ile
 50                  55                  60

Ala Pro Ile Leu Asp Glu Ile Ala Asp Glu Tyr Gln Gly Lys Leu Thr
 65                  70                  75                  80

Val Ala Lys Leu Asn Ile Asp Gln Asn Pro Gly Thr Ala Pro Lys Tyr
                 85                  90                  95

Gly Ile Arg Gly Ile Pro Thr Leu Leu Leu Phe Lys Asn Gly Glu Val
            100                 105                 110

Ala Ser Ala Thr Lys Val Gly Ala Leu Ser Lys Gly Gln Leu Lys Glu
        115                 120                 125

Phe Leu Asp Ala Asn Leu Ala
    130                 135

<210> SEQ ID NO 59
<211> LENGTH: 432
<212> TYPE: DNA
<213> ORGANISM: artificial sequence
<220> FEATURE:
<223> OTHER INFORMATION: variant of TRIAP-alpha
<220> FEATURE:
<221> NAME/KEY: CDS
<222> LOCATION: (1)..(429)

<400> SEQUENCE: 59 atg agc gat aaa att att cac ctg act gac gac agt ttt gac acg gat     48
Met Ser Asp Lys Ile Ile His Leu Thr Asp Asp Ser Phe Asp Thr Asp
 1               5                  10                  15 gta ctc aaa gcg gac ggg gcg atc ctc gtc gat ttc tgg gca gag tgg     96
Val Leu Lys Ala Asp Gly Ala Ile Leu Val Asp Phe Trp Ala Glu Trp
                20                  25                  30
```

```
tgc gcg agg gag ggg gct gat ggt gcg att tgt ggt tat aat ttg gct    144
Cys Ala Arg Glu Gly Ala Asp Gly Ala Ile Cys Gly Tyr Asn Leu Ala
         35                  40                  45 acg ttg gtt atg ctg ggt ccg agt gag cgg gtg ttt tgt ccg ctt tgt    192
Thr Leu Val Met Leu Gly Pro Ser Glu Arg Val Phe Cys Pro Leu Cys
 50                  55                  60 gag cct ggt ccg tgc aaa atg atc gcc ccg att ctg gat gaa atc gct    240
Glu Pro Gly Pro Cys Lys Met Ile Ala Pro Ile Leu Asp Glu Ile Ala
 65                  70                  75                  80 gac gaa tat cag ggc aaa ctg acc gtt gca aaa ctg aac atc gat caa    288
Asp Glu Tyr Gln Gly Lys Leu Thr Val Ala Lys Leu Asn Ile Asp Gln
                 85                  90                  95 aac cct ggc act gcg ccg aaa tat ggc atc cgt ggt atc ccg act ctg    336
Asn Pro Gly Thr Ala Pro Lys Tyr Gly Ile Arg Gly Ile Pro Thr Leu
            100                 105                 110 ctg ctg ttc aaa aac ggt gaa gtg gcg tcg gca acc aaa gtg ggt gca    384
Leu Leu Phe Lys Asn Gly Glu Val Ala Ser Ala Thr Lys Val Gly Ala
        115                 120                 125 ctg tct aaa ggt cag ttg aaa gag ttc ctc gac gct aac ctg gcg taa    432
Leu Ser Lys Gly Gln Leu Lys Glu Phe Leu Asp Ala Asn Leu Ala
    130                 135                 140
```

<210> SEQ ID NO 60
<211> LENGTH: 143
<212> TYPE: PRT
<213> ORGANISM: artificial sequence
<220> FEATURE:
<223> OTHER INFORMATION: Synthetic Construct

<400> SEQUENCE: 60

```
Met Ser Asp Lys Ile Ile His Leu Thr Asp Asp Ser Phe Asp Thr Asp
 1               5                  10                  15

Val Leu Lys Ala Asp Gly Ala Ile Leu Val Asp Phe Trp Ala Glu Trp
                 20                  25                  30

Cys Ala Arg Glu Gly Ala Asp Gly Ala Ile Cys Gly Tyr Asn Leu Ala
             35                  40                  45

Thr Leu Val Met Leu Gly Pro Ser Glu Arg Val Phe Cys Pro Leu Cys
     50                  55                  60

Glu Pro Gly Pro Cys Lys Met Ile Ala Pro Ile Leu Asp Glu Ile Ala
 65                  70                  75                  80

Asp Glu Tyr Gln Gly Lys Leu Thr Val Ala Lys Leu Asn Ile Asp Gln
                 85                  90                  95

Asn Pro Gly Thr Ala Pro Lys Tyr Gly Ile Arg Gly Ile Pro Thr Leu
            100                 105                 110

Leu Leu Phe Lys Asn Gly Glu Val Ala Ser Ala Thr Lys Val Gly Ala
        115                 120                 125

Leu Ser Lys Gly Gln Leu Lys Glu Phe Leu Asp Ala Asn Leu Ala
    130                 135                 140
```

<210> SEQ ID NO 61
<211> LENGTH: 22
<212> TYPE: PRT
<213> ORGANISM: Artificial sequence
<220> FEATURE:
<223> OTHER INFORMATION: fragment 1-22 of TRIP

<400> SEQUENCE: 61

```
Ala Arg Glu Gly Ala Asp Gly Ala Ile Cys Gly Tyr Asn Leu Ala Thr
 1               5                  10                  15

Leu Val Met Leu Gly Pro
```

```
<210> SEQ ID NO 62
<211> LENGTH: 21
<212> TYPE: PRT
<213> ORGANISM: Artificial Sequence
<220> FEATURE:
<223> OTHER INFORMATION: fragment 22-42 of TRIP

<400> SEQUENCE: 62

Pro Ser Glu Arg Val Phe Cys Pro Leu Cys Glu Pro Cys Ser Ser Asp
1               5                   10                  15

Ile Tyr Glu Leu Met
            20

<210> SEQ ID NO 63
<211> LENGTH: 32
<212> TYPE: PRT
<213> ORGANISM: Artificial Sequence
<220> FEATURE:
<223> OTHER INFORMATION: fragment 11-42 of TRIP

<400> SEQUENCE: 63

Gly Tyr Asn Leu Ala Thr Leu Val Met Leu Gly Pro Ser Glu Arg Val
1               5                   10                  15

Phe Cys Pro Leu Cys Glu Pro Cys Ser Ser Asp Ile Tyr Glu Leu Met
            20                  25                  30
```

INHIBITORS OF PROTEINS FROM THE RHO-GEF FAMILY

Figure 1:
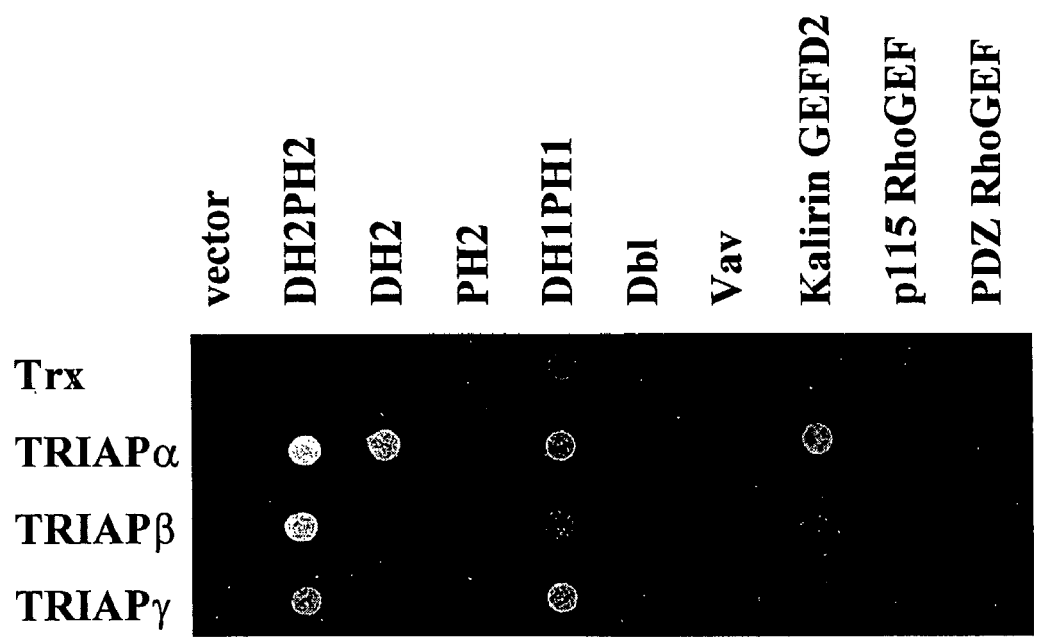

The present invention relates to inhibitors of proteins from the Rho-GEF family.

The present invention also relates to inhibitors of the protein Trio, and to the corresponding nucleotide sequences. The present invention also relates to the use of these inhibitors for the preparation of drugs.

Rho-GTPases are molecular switches that control actin cytoskeleton modifications during proliferation, transformation, cell migration and morphogenesis (Hall, A., 1998). They cycle between an inactive GDP-bound and an active GTP-bound form. Guanine nucleotide exchange factors (Rho-GEFs) accelerate their GDP/GTP exchange, rendering the GTPase active (Boguski et al., 1993). The large family of Rho-GEFs, like their GTPase targets, has been involved in a variety of cellular processes: several members of the Rho-GEF family were identified on the basis of their oncogenic properties, and numerous reports suggest that they are also involved in neuronal morphology (Stan et al., 1999).

Rho-GEs usually share a conserved catalytic region termed the DR domain (for Dbl-Homology) in reference to the oncogene Dbl, which was one of the first Rho-GEF characterized (Hart et al., 1994).

A complex protein, named Trio, isolated by its capacity to bind to the transmembrane tyrosine phosphatase LAR, is a protein containing two Rho-GEF domains and one serine kinase domain, spectin repeats, SH3 and an Immunoglobulin-like domains (Debant et al., 1996). The first Rho-GEF domain (TrioGEFD1) activates RhoG (Blangy et al., 2000), which in turn activates Rac and Cdc42, and promotes anchorage-independent cell growth (Seipel et al., 1999). In contrast, the second Rho-GEF domain (TrioGEFD2) acts specifically on RhoA (Debant et al., 1996), indicating that Trio is a multi-functional protein able to link several Rho-GTPase pathways in vivo (Bellanger et al., 1998). In addition, TrioGEFD1 binds to the actin binding proteins filamin and Tara, providing a direct link between Trio and the actin cytoskeleton (Bellanger et al., 2000; Seipel et al., 2001).

The understanding of Trio function made significant progress with recent data obtained from different studies of Trio family members. The *C. Elegans* and *Drosophila* Trio proteins are involved in axon guidance and cell migration (Steven et al., 1998; Bateman et al., 2000; Liebl et al., 2000; Newsome et al., 2000; Awasaki et al., 2000). TrioGEFD1 seems to play a major role in this process, whereas the function of TrioGEFD2 in the context of the full-length protein is unknown. Consistently, the rat Trio-like protein Kalirin is also involved in neuronal function (Penzes et al., 2001). Finally, the knock out of the trio gene in mouse was reported to be lethal, and trio –/– embryos display defects in neuronal organization and in muscle development (O'Brien et al., 2000).

The large Dbl family is involved in numerous physiological processes, and no specific inhibitors exist so far, Rho-GEFs, such as Trio, display multiple catalytic domains, whose relative contribution to the protein function is not always understood. Specific inhibitors of a given catalytic domain would thus represent powerful tools for precise structure-function studies and may be used as dominant negative inhibitors.

The aim of the present invention is to provide specific in vivo inhibitors of a Rho-GEF family member.

Another aim of the invention is to provide new peptides that inhibit a protein of the Rho-GEF family, particularly the protein Trio.

Another aim of the invention is to provide specific in viva inhibitors of a Rho-GEF family member, blocking specifically the RhoA pathway.

Another aim of the invention is to provide specific inhibitors of the GEFD2 domain of Trio.

Another aim of the present invention is to provide inhibitors of TrioGEF2, in order to develop drugs to protect axons from retraction.

The present invention concerns the use of an aptamer library for determining inhibitors of any one of the proteins from the Rho-GEF family, by an appropriate screening process, said aptamer library being such as defined in Geyer et al. (2000).

The large family of Rho-GEF proteins is involved in numerous physiological processes, but no specific inhibitors exist so far. Crystallographic studies of Rho-GEFs in complex with their GTPase targets indicate that numerous interaction sites between GEF and GTPase exist, rendering the prediction of an efficient inhibitor impossible. This makes the use of the aptamer library containing a large number of peptides, the sequences of which have not been determined, unobvious.

The aptamer library used in the present invention is the one described in Colas et al. (1996) or in Geyer et al. (2000).

It is constituted of random peptides inserted in thioredoxin.

The strategy of the aptamer library developed by P. Colas et al. (1996) is based on the fact that peptide loops that are anchored at both their amino and carboxy termini are capable of specific and high-affinity molecular recognition. The constructed library directs the synthesis in yeast of 20-residue peptides of random sequence inserted in the active site (residue 35) of the *E. coli* thioredoxin A and fused to a modified set of protein moieties from the original yeast two-hybrid system (Colas et al., 1996; patent no WO 96/02561 by Brent et al.). The library contains $2,9.10^9$ members of these constrained random peptides and it can be obtained such as described in the international application WO 96/02561.

The proteins from the Rho-GEF family can be chosen among the Dbl family members, that invariably contain a DH domain (for Dbl-Homology domain, in reference to the first Rho-GEF identified) that harbours the catalytic activity, and a PH domain, thought to be involved mainly in subcellular targeting. More than 40 Rho-GEFs have been identified in mammals.

An appropriate screening process comprises the following steps:

i) the appropriate bait is established, in this case the TH-PH module of the Rho-GEF or possibly the DH domain alone;

ii) the library is then screened with the selected bait to isolate aptamers that specifically bind to the bait;

iii) the selected aptamers are then tested for their capacity to inhibit the catalytic activity of the appropriate RhoGEF to determine inhibitory aptamers; for that purpose, the selected aptamers are expressed as GST-fusion proteins, and their capacity of inhibition is tested using the in vitro GEF assay (see Examples);

iv) the inhibitory aptamers are then tested for their capacity to inhibit in intact cells the activity of the Rho-GEF on the appropriate GTPase, using the GTPase activity assay (Benard et al., 2002);

v) the inhibitory aptamers selected at stage iv) are finally tested for their capacity to inhibit the physiological effect of the RhoGEF in intact cells; for that purpose, the aptamer is expressed as a GEP-fusion protein and transfected into cells, or possibly transduced into cells with fusion peptides or adenovirus infection (see Examples).

The present invention also relates to the use of said aptamer library, for determining inhibitors of the protein Trio.

Rho-GTPases are molecular switches that control actin cytoskeleton modifications during proliferation, transformation, cell migration and morphogenesis. In fibroblasts, Rac, a particular Rho-GTPase, is involved in ruffle and lamellipodia formation, which is associated with cell motility, while RhoA, another Rho-GTPase, antagonizes this pathway by stimulating the formation of stress fibers, that are important for adhesion to the extracellular matrix. In neuronal cells, the Rac pathway is essential for axonal elongation and axon guidance, while RhoA activation mediates axon retraction and growth cone collapse induced by different repulsive cues. Targeting the RhoA-mediated retraction pathway could have potential applications in axon regeneration, since axons in the mammalian central nervous system do not spontaneously regenerate following injury, because of the presence of growth inhibitory factors in the central nervous system.

The Rho-GTPases are activated by Rho-GEFs that accelerate their GDP/GTP exchange. Rho-GEFs, like their GTPase targets, control a variety of physiological processes: several Rho-GEFs have been isolated by their capacity to transform NTH3T3 cells, while other Rho-GEFs have been involved in various functions such as lymphocyte activation, metastasis, neuronal morphology or development. The large family of GEFs invariably contains a DH domain containing the catalytic activity associated with a PH domain thought to be involved mainly in subcellular targeting.

Trio is a unique protein that possesses two GEF domains of distinct specificity and is involved in neuronal morphology and axon guidance. The first RhoGEF domain (TrioGEFD1) activates the Rac pathway, while the second RhoGEF domain (TrioGEFD2) activates RhoA, indicating that Trio controls neuronal morphology by its capacity to modulate the activity of Rho-GTPases that stimulate antagonistic pathways.

Given the fact that TrioGEFD2 activates the RhoA pathway, it is of crucial importance to identify inhibitors of this domain, that may have potential applications in axon regeneration.

According to an advantageous embodiment, the present invention also relates to the use of said aptamer library, for determining specific inhibitors of the GEFD2 domain of the protein Trio (TrioGEFD2).

The present invention also relates to the use of said aptamer library, for determining inhibitors of the protein Trio which specifically bind to the GEFD1 domain of the protein Trio (TrioGEFD1).

The present invention also relates to the use of said aptamer library, for determining inhibitors of the protein Trio which do not inhibit TrioGEFD1.

Inhibitors of the protein Trio which do not inhibit TrioGEFD1 can bind or not to the GEFD1 domain of the protein Trio.

The present invention also relates to a process for determining inhibitors of any one of the proteins from the Rho-GEF family, comprising:
- a step of contacting said protein for which an inhibitor is sought with the peptides from an aptamer library,
- a step of recovering a first group of peptides which specifically bind to said protein, particularly to the catalytic domain of the GEF region of said protein,
- a step of recovering, among the first group of peptides as mentioned above, the peptide which specifically inhibits the in vitro exchange activity of said protein towards any one of the proteins from the Rho-GTPase family, as determined for example in the GEF assay, and
- a step of testing the peptide as mentioned above for its capacity to inhibit in intact cells the activity of the Rho-GEF on the appropriate GTPase, using for example the GTPase activity assay.

The GTPase activity assay is for example the one described in Benard et al. (2002).

The present invention also relates to a process for determining inhibitors of any one of the proteins from the Rho-GEF family, comprising:
- a step of contacting said protein for which an inhibitor is sought with the peptides from an aptamer library,
- a step of recovering a first group of peptides which specifically bind to said protein, particularly to the catalytic domain of the GEF region of said protein,
- a step of recovering, among the first group of peptides as mentioned above, the peptide which specifically inhibits the in vitro exchange activity of said protein towards RhoA, as determined for example in the GEF assay, and
- a step of testing the peptide as mentioned above for its capacity to inhibit in intact cells the activity of the Rho-GEF on RhoA, using for example the GTPase activity assay.

The GTPase activity assay is for example the one described in Ren et al. (1999).

The present invention also relates to a polypeptide, characterized in that it comprises or consists of any one of the following amino acid sequences:
- the sequence SEQ ID NO: 2,
- or any sequence derived from the sequence SEQ ID NO: 2 as defined above, especially by substitution, deletion or addition of one or more amino acids, with the proviso that said derived sequence inhibits TrioGEFD2,
- or any homologous sequence of the sequence SEQ ID NO: 2 as defined above, preferably having a homology of at least about 30%, in particular of at least about 50%, with the sequence SEQ ID NO: 2, with the proviso that said homologous sequence inhibits TrioGEFD2,
- or any fragment of any one of the sequences as defined above, said fragment being preferably consisted of at least about 40 to about 140, preferably of about 137 amino acids of the sequence SEQ ID NO: 2, with the proviso that said fragment inhibits TrioGEFD2.

SEQ ID NO: 2 corresponds to the sequence of a new aptamer TRIAPα, which contains 154 amino acids.

The new aptamer TRIAPα (Trio inhibitory aptamer) specifically inhibits the in vitro TrioGEFD2 guanine nucleotide exchange activity towards RhoA.

TRIAPα contains a variable region of 42 amino acids inserted into the thioredoxin protein. This variable region has no homology with any sequences in the databases.

To test whether the Trio-binding aptamers could inhibit the catalytic activity of GEFD2 towards the GTPase RhoA, the in vitro guanine nucleotide exchange assay (GEF assay) can be used.

For that purpose, aptamers, TrioGEFD2 and RhoA are expressed as GST-fusion proteins. RhoA is loaded with $^3$H-GDP, and the release of GDP is followed after addition of GEFD2 in presence or in absence of the selected aptamers (as described in Debant et al., 1996).

To test whether the Trio-binding aptamers could inhibit the catalytic activity of GEFD2 in intact cells, the inhibitory aptamers are expressed as GEP-fusion proteins, and tested in intact cells for their capacity to inhibit the activation of RhoA, using the GTPase activity assay (Ren et al., 1999).

An advantageous polypeptide according to the invention is a polypeptide such as defined above, characterized in that it comprises or consists of any one of the following amino acid sequences:

the sequence SEQ ID NO: 4, or any sequence derived from the sequence SEQ ID NO: 4 as defined above, especially by substitution, deletion or addition of one or more amino acids, with the proviso that said derived sequence inhibits TrioGEFD2, or any homologous sequence of the sequence SEQ ID NO: 4 as defined above, preferably having a homology of at least about 30%, in particular of at least about 50%, with the sequence SEQ ID NO: 4, with the proviso that said homologous sequence inhibits TrioGEFD2, or any fragment of any one of the sequences as defined above, said fragment being preferably consisted of at least about 25 to about 40, preferably of about 30 amino acids of the sequence SEQ ID NO: 4, with the proviso that said fragment inhibits TrioGEFD2.

SEQ ID NO: 4 corresponds to the sequence of a new peptide TRIPα, which contains 42 amino acids.

The new peptide TRIPα (Trio inhibitory peptide) corresponds to the variable region of the aptamer TRIAPα. Thus, TRIPα is a fragment of TRIAPα, and it corresponds to the sequence delimited from the amino acid in position (36) to the amino acid in position (77) of TRIAPα.

TRIPα is as potent as TRIAPα to block in vitro and in vivo TrioGEFD2 exchange activity, suggesting that TRIPα inhibition is not dependent on the thioredoxin scaffold.

The present invention also relates to a fragment of TRIPα such as defined above, characterized in that it is chosen among the following sequences: SEQ ID NO: 6, SEQ ID NO: 8, SEQ ID NO: 10, SEQ ID NO: 12, SEQ ID NO: 14, SEQ ID NO: 16 and SEQ ID NO: 18.

SEQ ID NO: 6 is a fragment of the peptide TRIPα: it is also referred to as TRIPα 9-42. It corresponds to the fragment of TRIPα, delimited from the amino acid in position (9) to the amino acid in position (42) of the above-mentioned sequence SEQ ID NO: 4.

SEQ ID NO: 8 is a fragment of the peptide TRIPα: it is also referred to as TRIPα 9-40. It corresponds to the fragment of TRIPα, delimited from the amino acid in position (9) to the amino acid in position (40) of the above-mentioned sequence SEQ ID NO: 4.

SEQ ID NO: 10 is a fragment of the peptide TRIPα: it is also referred to as TRIPα 9-38. It corresponds to the fragment of TRIPα, delimited from the amino acid in position (9) to the amino acid in position (38) of the above-mentioned sequence SEQ ID NO: 4.

SEQ ID NO: 12 is a fragment of the peptide TRIPα: it is also referred to as TRIPα 9-36. It corresponds to the fragment of TRIPα, delimited from the amino acid in position (9) to the amino acid in position (36) of the above-mentioned sequence SEQ ID NO: 4.

SEQ ID NO: 14 is a fragment of the peptide TRIPα: it is also referred to as TRIPα 9-34. It corresponds to the fragment of TRIPα, delimited from the amino acid in position (9) to the amino acid in position (34) of the above-mentioned sequence SEQ ID No: 4.

SEQ ID NO: 16 is a fragment of the peptide TRIPα: it is also referred to as TRIPα 9-33. It corresponds to the fragment of TRIPα, delimited from the amino acid in position (9) to the amino acid in position (33) of the above-mentioned sequence SEQ ID NO: 4.

SEQ ID NO: 18 is a fragment of the peptide TRIPα: it is also referred to as TRIPα 1-33. It corresponds to the fragment of TRIPα, delimited from the amino acid in position (1) to the ammo acid in position (33) of the above-mentioned sequence SEQ ID NO: 4.

The present invention relates to a variant of TRIAPα such as defined above, characterized in that it is chosen among the following sequences: SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40 SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58 and SEQ ID NO: 60.

SEQ ID NO: 20 is a variant of the aptamer TRIAPα: it is also referred to as TRIAPα 9-42. It contains the fragment of TRIPα, TRIPα 9-42, represented by the sequence SEQ ID NO: 6, inserted into the thioredoxin.

SEQ ID NO: 22 is a variant of the aptamer TRIAPα: it is also referred to as TRIAPα 9-40. It contains the fragment of TRIPα, TRIPα 9-40, represented by the sequence SEQ ID NO: 8, inserted into the thioredoxin.

SEQ ID NO: 24 is a variant of the aptamer TRIAPα: it is also referred to as TRIAPα 9-38. It contains the fragment of TRIPα, TRIPα 9-38, represented by the sequence SEQ ID NO: 10, inserted into the thioredoxin.

SEQ ID NO: 26 is a variant of the aptamer TRIAPα: it is also referred to as TRIAPα 9-36. It contains the fragment of TRIPα, TRIPα 9-36, represented by the sequence SEQ ED NO: 12, inserted into the thioredoxin.

SEQ ID NO: 28 is a variant of the aptamer TRIAPα: it is also referred to as TRIAPα 9-34. It contains the fragment of TRIPα, TRIPα9-34, represented by the sequence SEQ ID NO: 14, inserted into the thioredoxin.

SEQ ID NO: 30 is a variant of the aptamer TRIAPα: it is also referred to as TRIAPα 9-33. It contains the fragment of TRIPα, TRIPα 9-33, represented by the sequence SEQ ID NO: 16, inserted into the thioredoxin.

SEQ ID NO: 32 is a variant of the aptamer TRIAPα: it is also referred to as TRIAPα 1-33. It contains the fragment of TRIPα, TRIPα 1-33, represented by the sequence SEQ ID NO: 18, inserted into the thioredoxin.

SEQ ID NO: 34 is a variant of the aptamer TRIAPα, which contains the fragment of TRIPα, TRIPα 9-42, represented by the sequence SEQ ID NO: 6, inserted into the thioredoxin.

SEQ ID NO: 36 is a variant of the aptamer TRIAPα, which contains the fragment of TRIPα, TRIPα 9-40, represented by the sequence SEQ ID NO: 8, inserted into the thioredoxin.

SEQ ID NO: 38 is a variant of the aptamer TRIAPα, which contains the fragment of TRIPα, TRIPα 9-38, represented by the sequence SEQ ID NO: 10, inserted into the thioredoxin.

SEQ ID NO: 40 is a variant of the aptamer TRIAPα, which contains the fragment of TRIPα, TRIPα 9-36, represented by the sequence SEQ ID NO: 12, inserted into the thioredoxin.

SEQ ID NO: 42 is a variant of the aptamer TRIAPα, which contains the fragment of TRIPα, TRIPα 9-34, represented by the sequence SEQ ID NO: 14, inserted into the thioredoxin.

SEQ ID NO: 44 is a variant of the aptamer TRIAPα, which contains the fragment of TRIPα, TRIPα 9-33, represented by the sequence SEQ ID NO: 16, inserted into the thioredoxin.

SEQ ID NO: 46 is a variant of the aptamer TRIAPα, which contains the fragment of TRIPα, TRIPα 1-33, represented by the sequence SEQ ID NO: 18, inserted into the thioredoxin.

SEQ ID NO: 48 is a variant of the aptamer TRIAPα, which contains the fragment of TRIPα, TRIPα 9-42, represented by the sequence SEQ ID NO: 6, inserted into the thioredoxin.

SEQ ID NO: 50 is a variant of the aptamer TRIAPα, which contains the fragment of TRIPα, TRIPα 9-40, represented by the sequence SEQ ID NO: 8, inserted into the thioredoxin.

SEQ ID NO: 52 is a variant of the aptamer TRIAPα, which contains the fragment of TRIPα, TRIPα 9-38, represented by the sequence SEQ ID NO: 10, inserted into the thioredoxin.

SEQ ID NO: 54 is a variant of the aptamer TRIAPα, which contains the fragment of TRIPα, TRIPα 9-36, represented by the sequence SEQ ID NO: 12, inserted into the thioredoxin.

SEQ ID NO: 56 is a variant of the aptamer TRIAPα, which contains the fragment of TRIPα, TRIPα 9-34, represented by the sequence SEQ ID NO: 14, inserted into the thioredoxin.

SEQ ID NO: 58 is a variant of the aptamer TRIAPα, which contains the fragment of TRIPα, TRIPα 9-33, represented by the sequence SEQ ID NO: 16, inserted into the thioredoxin.

SEQ ID NO: 60 is a variant of the aptamer TRIAPα, which contains the fragment of TRIPα, TRIPα 1-33, represented by the sequence SEQ ID NO: 18, inserted into the thioredoxin.

Thus, the above-mentioned variants of TRIAPα, SEQ ID NO: 20, SEQ ID NO: 22, SEQ ID NO: 24, SEQ ID NO: 26, SEQ ID NO: 28, SEQ ID NO: 30 and SEQ ID NO: 32, are constituted by:
- a first fragment of the thioredoxin, which corresponds to the sequence delimited from the amino acid in position (1) to the amino acid in position (35),
- a fragment of TRIPα, chosen among the following sequences: SEQ ID NO: 6, SEQ ID NO: 8, SEQ ID NO: 10, SEQ ID NO: 12, SEQ ID NO: 14, SEQ ID NO: 16 and SEQ ID NO: 18, and
- a second fragment of the thioredoxin, which corresponds to the sequence delimited from the amino acid in position (34) to the amino acid in position (110).

Thus, the above-mentioned variants of TRIAPα, SEQ ID NO: 34, SEQ ID NO: 36, SEQ ID NO: 38, SEQ ID NO: 40, SEQ ID NO: 42, SEQ ID NO: 44 and SEQ ID NO: 46, are constituted by:
- a first fragment of the thioredoxin, which corresponds to the sequence delimited from the amino acid in position (1) to the amino acid in position (35),
- a fragment of TRIPα, chosen among the following sequences: SEQ ID NO: 6, SEQ ID NO: 8, SEQ ID NO: 10, SEQ ID NO: 12, SEQ ID NO: 14, SEQ ID NO: 16 and SEQ ID NO: 18, and
- a second fragment of the thioredoxin, which corresponds to the sequence delimited from the amino acid in position (36) to the amino acid in position (110).

Thus, the above-mentioned variants of TRIAPα, SEQ ID NO: 48, SEQ ID NO: 50, SEQ ID NO: 52, SEQ ID NO: 54, SEQ ID NO: 56, SEQ ID NO: 58 and SEQ ID NO: 60, are constituted by:
- a first fragment of the thioredoxin, which corresponds to the sequence delimited from the amino acid in position (1) to the amino acid in position (33),
- a fragment of TRIPα, chosen among the following sequences: SEQ ID NO: 6, SEQ ID NO: 8, SEQ ID NO: 10, SEQ ID NO: 12, SEQ ID NO: 14, SEQ ID NO: 16 and SEQ ID NO: 18, and
- a second fragment of the thioredoxin, which corresponds to the sequence delimited from the amino acid in position (34) to the amino acid in position (110).

The present invention relates to a polypeptide such as defined above, comprising any one of the above-mentioned amino acid sequences, and containing flanking parts consisting of fragments of the thioredoxin.

E. coli thioredoxin is a small protein very stable which can be produced at high levels. Thioredoxin contains a Cys-Cys active loop where peptides can be inserted and subjected to conformational constraint, since both cysteines can form a disulphide bond under appropriate conditions.

The expression "flanking parts consisting of fragments of the thioredoxin" can mean either that the N-terminal and C-terminal flanking parts when considered together correspond to the complete sequence of thioredoxin (in such a case the above-mentioned amino sequences are inserted in thioredoxin), or that the N-terminal and C-terminal flanking parts are themselves fragments from thioredoxin, the size of said fragment advantageously being from about 20 to about 60 amino acids.

The present invention also concerns a nucleotide sequence coding for a polypeptide such as defined above.

The present invention also relates to a nucleotide sequence such as defined above, characterized in that it comprises or consists of:
- the nucleotide sequence represented by SEQ ID NO: 1 coding for the polypeptide represented by SEQ ID NO: 2,
- or any nucleotide sequence derived from the sequence SEQ ID NO: 1 by degeneration of the genetic code, and coding for a polypeptide represented by SEQ ID NO: 2,
- or any nucleotide sequence derived from the sequence SEQ ID NO: 1, especially by substitution, deletion or addition of one or more nucleotides, and coding for a derived polypeptide such as defined above,
- or any nucleotide sequence homologous of SEQ ID NO: 1, having preferably a homology of at least about 15%, in particular of at least about 20%, and preferably of at least 30%, with the sequence SEQ ID NO: 1 coding for a polypeptide homologous of SEQ ID NO: 2, such as defined above,
- or any fragment of the nucleotide sequence SEQ ID NO: 1 or of any one of the above-defined nucleotide sequences, said fragment being preferably consisted of at least about 120 to about 420, preferably of about 411 nucleotides of the sequence SEQ ID NO: 1,
- or any complementary nucleotide sequence of the above-mentioned sequences or fragments,
- or any nucleotide sequence capable of hybridizing in stringent conditions with the complementary sequence of one of the above-mentioned sequences or fragments.

SEQ ID NO: 1 is a new nucleotide sequence, coding for the new peptide TRIAPα, represented by SEQ ID NO: 2.

The expression "hybridizing in stringent conditions" corresponds to a hybridization at 42° C. in 50% formamide, 4×SSC (sodium chloride sodium citrate buffer), followed by a washing at 65° C. in 0.1×SSC, 0.1% SDS.

The present invention also relates to a nucleotide sequence such as defined above, characterized in that it comprises or consists of:
- the nucleotide sequence represented by SEQ ID NO: 3 coding for the polypeptide represented by SEQ ID NO: 4,
- or any nucleotide sequence derived from the sequence SEQ ID NO: 3 by degeneration of the genetic code, and coding for a polypeptide represented by SEQ ID NO: 4,
- or any nucleotide sequence derived from the sequence SEQ ID NO: 3, especially by substitution, deletion or addition of one or more nucleotides, and coding for a derived polypeptide such as defined above,
- or any nucleotide sequence homologous of SEQ ID NO: 3, having preferably a homology of at least about 15%, in particular of at least about 20%, and preferably of at least 30%, with the sequence SEQ ID NO: 3 coding for a polypeptide homologous of SEQ ID NO: 4, such as defined in above,
- or any fragment of the nucleotide sequence SEQ ID NO: 1 or of any one of the above-defined nucleotide sequences, said fragment being preferably consisted of at least about 75 to about 120, preferably of about 90 nucleotides of the sequence SEQ ID NO: 3, or any complementary nucleotide sequence of the above-mentioned sequences or fragments, or any nucleotide sequence capable of hybridizing in stringent conditions with the complementary sequence of one of the above-mentioned sequences or fragments.

SEQ ID NO: 3 is a new nucleotide sequence, coding for the new peptide TRIPα, represented by SEQ ID NO: 4.

The expression "hybridizing in stringent conditions" corresponds to a hybridization at 4200 in 50% formamide, 4×SSC (sodium chloride sodium citrate buffer), followed by a washing at 65° C. in 0.1×SSC, 0.1% SDS.

A fragment of a nucleotide sequence such as defined above, characterized in that it is chosen among the following sequences: SEQ ID NO: 5, SEQ ID NO: 7, SEQ ID NO: 9, SEQ ID NO: 11, SEQ ID NO: 13, SEQ ID NO: 15 and SEQ ID NO: 17.

SEQ ID NO: 5 corresponds to the nucleotide sequence coding for SEQ ID NO: 6, a fragment of the peptide TRIPα, also referred to as TRIPα 9-42. It corresponds to the fragment of SEQ ID NO: 3, delimited from the nucleotide in position (25) to the nucleotide in position (126) of said sequence SEQ ID NO: 3.

SEQ ID NO: 7 corresponds to the nucleotide sequence coding for SEQ ID NO: 8, a fragment of the peptide TRIPα, also referred to as TRIPα 9-40. It corresponds to the fragment of SEQ ID NO: 3, delimited from the nucleotide in position (25) to the nucleotide in position (120) of said sequence SEQ ID NO: 3.

SEQ ID NO: 9 corresponds to the nucleotide sequence coding for SEQ ID NO: 10, a fragment of the peptide TRIPα, also referred to as TRIPα 9-38. It corresponds to the fragment of SEQ ID NO: 3, delimited from the nucleotide in position (25) to the nucleotide in position (114) of said sequence SEQ ID NO: 3.

SEQ ID NO: 11 corresponds to the nucleotide sequence coding for SEQ ID NO: 12, a fragment of the peptide TRIPα, also referred to as TRIPα 9-36. It corresponds to the fragment of SEQ ID NO: 3, delimited from the nucleotide in position (25) to the nucleotide in position (108) of said sequence SEQ ID NO: 3.

SEQ ID NO: 13 corresponds to the nucleotide sequence coding for SEQ ID NO: 14, a fragment of the peptide TRIPα, also referred to as TRIPα 9-34. It corresponds to the fragment of SEQ ID NO: 3, delimited from the nucleotide in position (25) to the nucleotide in position (102) of said sequence SEQ ID NO: 3.

SEQ ID NO: 15 corresponds to the nucleotide sequence coding for SEQ ID NO: 16, a fragment of the peptide TRIPα, also referred to as TRIPα 9-33. It corresponds to the fragment of SEQ ID NO: 3, delimited from the nucleotide in position (25) to the nucleotide in position (99) of said sequence SEQ ID NO: 3.

SEQ ID NO: 17 corresponds to the nucleotide sequence coding for SEQ ID NO: 18, a fragment of the peptide TRIPα, also referred to as TRIPα 1-33. It corresponds to the fragment of SEQ ID NO: 3, delimited from the nucleotide in position (1) to the nucleotide in position (99) of said sequence SEQ ID NO: 3.

The present invention relates to a variant of a nucleotide sequence such as defined above, characterized in that it is chosen among the following sequences: SEQ ID NO: 19, SEQ ID NO: 21, SEQ ID NO: 22, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39 SEQ ID NO: 41, SEQ ID NO: 43, SEQ ID NO: 45, SEQ ID NO:47, SEQ ID NO: 49, SEQ ID NO: 51, SEQ ID NO: 53, SEQ ID NO: 55, SEQ ID NO: 57 and SEQ ID NO: 59.

SEQ ID NO: 19 corresponds to the nucleotide sequence coding for SEQ ID NO: 20, a variant of TRIAPα, represented by the nucleotide sequence SEQ ID NO: 1.

SEQ ID NO: 21 corresponds to the nucleotide sequence coding for SEQ ID NO: 22, a variant of TRIAPα, represented by the nucleotide sequence SEQ ID NO: 1.

SEQ ID NO: 23 corresponds to the nucleotide sequence coding for SEQ ID NO: 24, a variant of TRIAPα, represented by the nucleotide sequence SEQ ID NO: 1.

SEQ ID NO: 25 corresponds to the nucleotide sequence coding for SEQ ID NO: 26, a variant of TRIAPα, represented by the nucleotide sequence SEQ ID NO: 1.

SEQ ID NO: 27 corresponds to the nucleotide sequence coding for SEQ ID NO: 28, a variant of TRIAPα, represented by the nucleotide sequence SEQ ID NO. 1.

SEQ ID NO: 29 corresponds to the nucleotide sequence coding for SEQ ID NO: 30, a variant of TRIAPα, represented by the nucleotide sequence SEQ ID NO: 1.

SEQ ID NO: 31 corresponds to the nucleotide sequence coding for SEQ ID NO: 32, a variant of TRIAPα, represented by the nucleotide sequence SEQ ID NO: 1.

SEQ ID NO: 33 corresponds to the nucleotide sequence coding for SEQ ID NO: 34, a variant of TRIAPα, represented by the nucleotide sequence SEQ ID NO: 1.

SEQ ID NO: 35 corresponds to the nucleotide sequence coding for SEQ ID NO: 36, a variant of TRIAPα, represented by the nucleotide sequence SEQ ID NO: 1.

SEQ ID NO: 37 corresponds to the nucleotide sequence coding for SEQ ID NO: 38, a variant of TRIAPα, represented by the nucleotide sequence SEQ ID NO: 1.

SEQ ID NO: 39 corresponds to the nucleotide sequence coding for SEQ ID NO: 40, a variant of TRIAPα, represented by the nucleotide sequence SEQ ID NO: 1.

SEQ ID NO: 41 corresponds to the nucleotide sequence coding for SEQ ID NO: 42, a variant of TRIAPα, represented by the nucleotide sequence SEQ ID NO: 1.

SEQ ID NO: 43 corresponds to the nucleotide sequence coding for SEQ ID NO: 44, a variant of TRIAPα, represented by the nucleotide sequence SEQ ID NO: 1.

SEQ ID NO: 45 corresponds to the nucleotide sequence coding for SEQ ID NO: 46, a variant of TRIAPα, represented by the nucleotide sequence SEQ ID NO: 1.

SEQ ID NO 47 corresponds to the nucleotide sequence coding for SEQ ID NO: 48, a variant of TRIAPα, represented by the nucleotide sequence SEQ ID NO: 1.

SEQ ID NO: 49 corresponds to the nucleotide sequence coding for SEQ ID NO: 50, a variant of TRIAPα, represented by the nucleotide sequence SEQ ID NO: 1.

SEQ ID NO: 51 corresponds to the nucleotide sequence coding for SEQ ID NO: 52, a variant of TRIAPα, represented by the nucleotide sequence SEQ ID NO: 1.

SEQ ID NO: 53 corresponds to the nucleotide sequence coding for SEQ ID NO: 54, a variant of TRIAPα, represented by the nucleotide sequence SEQ ID NO: 1.

SEQ ID NO: 55 corresponds to the nucleotide sequence coding for SEQ ID NO: 56, a variant of TRIAPα, represented by the nucleotide sequence SEQ ID NO: 1.

SEQ ID NO: 57 corresponds to the nucleotide sequence coding for SEQ ID NO: 58, a variant of TRIAPα, represented by the nucleotide sequence SEQ ID NO: 1.

SEQ ID NO: 59 corresponds to the nucleotide sequence coding for SEQ ID NO: 60, a variant of TRIAPα, represented by the nucleotide sequence SEQ ID NO: 1.

The present invention relates to a recombinant vector, especially a plasmid, a cosmid, a phage or a DNA virus, containing a nucleotide sequence such as defined above.

The present invention also relates to a recombinant vector such as defined above, containing the elements necessary for the expression in a host cell of the polypeptides coded by the above-mentioned nucleic acids, inserted in said vector.

The present invention relates to a host cell, in particular chosen from bacteria, viruses, yeasts, fungi, plants or mammalian cells, the said host cell being transformed, especially by means of a vector such as defined above, in such a way that its genome contains a nucleotide sequence such as defined above.

The present invention also relates to a pharmaceutical composition characterized in that it comprises a polypeptide such as defined above, in association with a pharmaceutically acceptable vehicle.

An advantageous pharmaceutical composition according to the invention is characterized in that it contains from about 700 μg to about 80 mg, preferably from about 7 to about 40 mg, as a unit dose, of the above-mentioned polypeptide.

The present invention also concerns the use of a polypeptide such as defined above, for the preparation of a drug for the treatment of pathologies that are related to the peripheral nervous system or to the central nervous system, in particular for the treatment of accidental paralysis related to the spinal marrow.

The present invention also relates to the use of TRIPα or TRIAPα, for the preparation of a drug in order to prevent axons from retraction.

TRIPα and its derivatives can be used in nervous system damages, where an increase in neurite extension or regeneration is desired. Patients suffering from traumatic disorders like spinal cord injuries, spinal cord or other CNS pathway lesions, from surgical nerve lesions, damages following infarction, infection, exposure to toxic agents, malignancy, or patients with various types of degenerative disorders of the CNS can be treated with such an inhibitor. Examples of degenerative diseases include but are not limited to Alzheimer's Disease, Parkinson's Disease, Huntington's Disease, amyotrophic lateral sclerosis, and other dementias.

TRIPα seems to be particularly useful to promote regeneration of nerve fibers following spinal cord damage.

LEGENDS TO THE FIGURES

FIG. 1: Binding Specificity of the Selected Aptamers in Yeast

The selected aptamers TRIAPα, TRIAPβ, TRIAPγ, binding to TrioGEFD2 were tested for specific interaction with different baits as follows: TrioGEFD2 (DH2PH2, amino acids 1848-2298), TrioDR2 (amino acids 1848-2096), TrioPH2 (amino acids 2107-2223), or TrioGEFD1 (DH1PH1, amino acids 1232-1620), Dbl (amino acids 498-826) (Hart et al. 1994), Vav (amino acids 127-598)(Zhang et al., 1994), GEFD2 domain of Kalirin (a.a. 1640-1980) (Penzes et al., 2001), PDZRhoGEF (amino acids 964-1362) (Fukuhara et al., 1999) and p115RhoGEF (amino acids 391-870)(Wells et al, 2002), and monitored for growth on selective medium. Trx represents the thioredoxin protein with no inserted peptide.

TRIAPβ and TRIAPγ bind only to the DH2PH2 module, whereas TRIAPα also binds to the DH2 catalytic domain. It is noteworthy that TRIAPα also weakly interacts with TrioDHPH1 and with the second RhoGEF domain of the Trio family member kalirin.

Figure 2A:
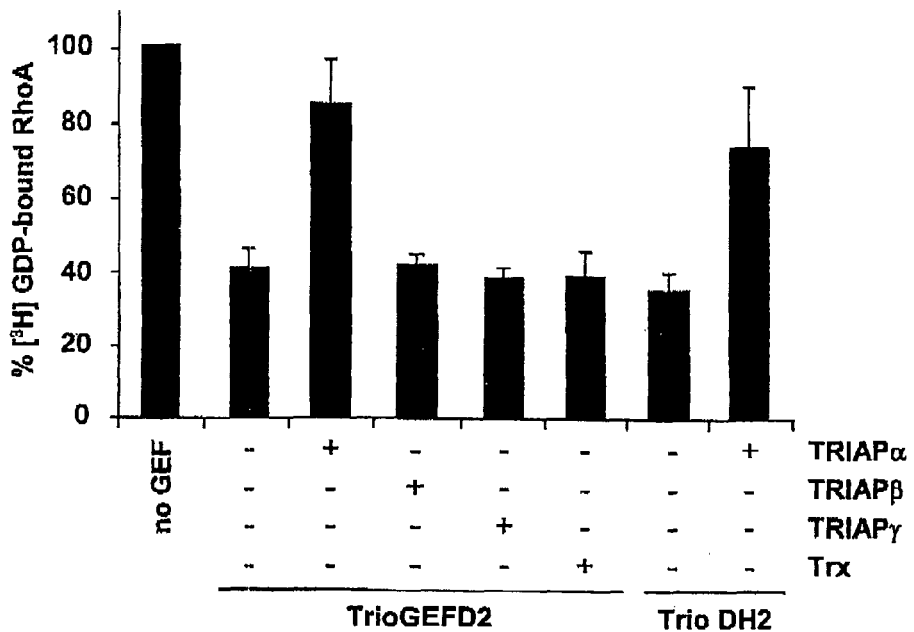
Figure 2B:
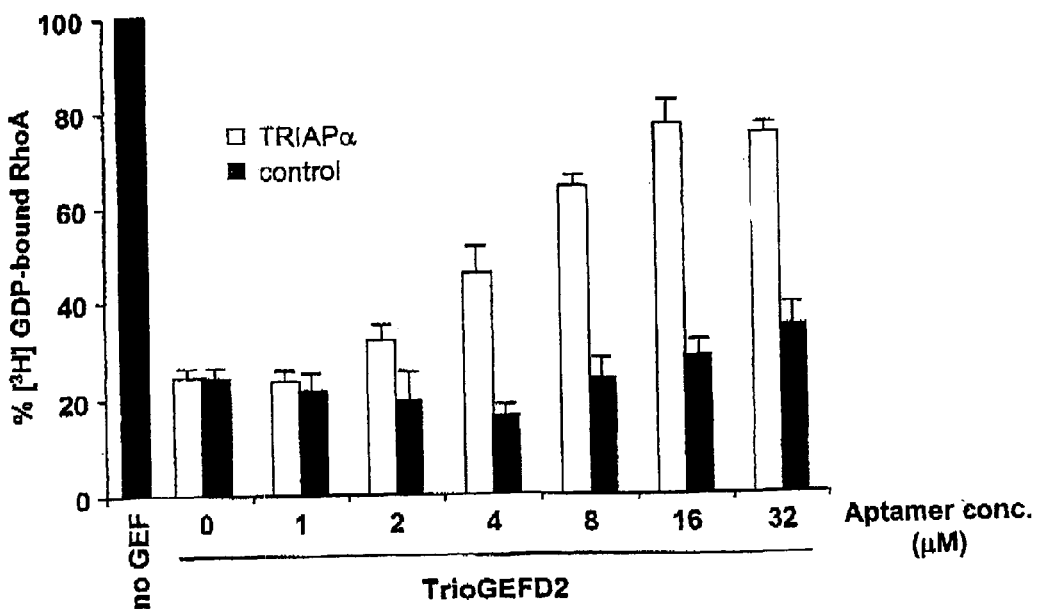

FIGS. 1A and 2B: TRIAPα Inhibits TrioGEFD2 Exchange Activity on RhoA in vitro.

FIG. 2A shows that TRIAPα is a potent inhibitor of TrioGEFD2 activity.

The y-axis represents the percentage of [$^3$H]GDP-bound RhoA.

A 20-fold molar excess (8 μM) of GST-aptamers TRIAPα, TRIAPβ (another TrioGEFD2 binding aptamer), TRIAPγ (another TrioGEFD2 binding aptamer) or the empty thioredoxine (Trx) were pre-incubated with 0.4 μM GST-GEFD2 (left side of FIG. 2A) or 0.4 μM GST-DH2 (right side of FIG. 2A), as indicated, before adding 0.3 μM of [$^3$H]GDP loaded GST-RhoA. The exchange activity was monitored by the decrease of [$^3$H]GDP bound-RhoA after 15 min (see Materials and Methods). The amount of [$^3$H]GDP bound-RhoA incubated without GEF (first bar on the left) was defined as 100% The values and errors bars were calculated from at least three independent experiments.

"+" means that the corresponding aptamer (written on the right part of the figure) is present in the reaction; and "−" means that the corresponding aptamer is absent from the reaction.

TRIAPα inhibits both TrioGEFD2 and TrioDH2 exchange activities on RhoA in vitro, while TRIAPβ and TRIAPγ have no effect.

FIG. 2B shows that TRIAPα inhibition of GEFD2 is dose-dependent.

The x-axis represents the aptamer concentration added in the reaction and the y-axis represents the percentage of [$^3$H] GDP-bound RhoA.

The first bar on the left corresponds to the amount of [$^3$H]GDP bound-RhoA incubated without GEF, defined as 100%.

0.4 μM GST-GEFD2 were incubated with increasing amounts of GST-TRIAPα (grey bars) or GST (black bars), and the exchange assay was then performed on 0.3 μM RhoA, as described in A.

Inhibition of TrioGEFD2 by TRIAPα is concentration-dependent, with an apparent half-inhibitory concentration of 4 μM.

Figure 3:
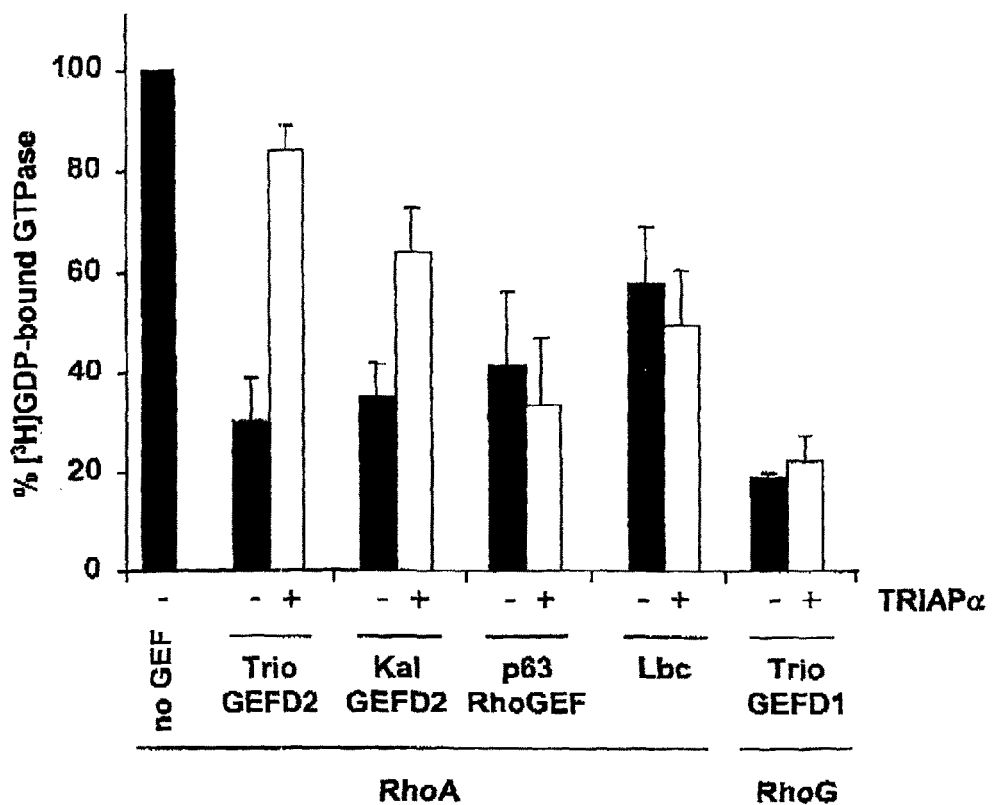

FIG. 3: TRIAPα Inhibition is Specific for TrioGEFD2

The y-axis represents the percentage of [$^3$H]GDP-bound RhoA.

To test the specificity of TRIAPα inhibition in vitro, exchange experiments were performed either on RhoA with different RhoA-specific GEFs: Trio GEFD2 (0.4 μM), Kalirin GEFD2 (KalGEFD2, 1.7 μM), p63RhoGEF (Souchet et al., 2002) (0.4 μM) and Lbc (amino acids 172-598; Zheng et al., 1995) (0.4 μM), or on RhoG, with the RhoG-specific GEF domain of Trio (TrioGEFD1, 0.1 μM). Exchange assays were performed with the recombinant GEFs as described in FIG. 2A. Different concentrations of RhoGEFs were used to yield a similar nucleotide exchange efficiency. For each exchange factor, three independent experiments were done in absence (black bar) or in the presence (grey bar) of a 20-fold molar excess of TRIAPα.

TRIAPα has no effect on the exchange activities of Lbc, p63RhoGEF and TrioGEFD 1, while it weakly inhibits Kalirin GEFD2 activity on RhoA.

Figure 4:
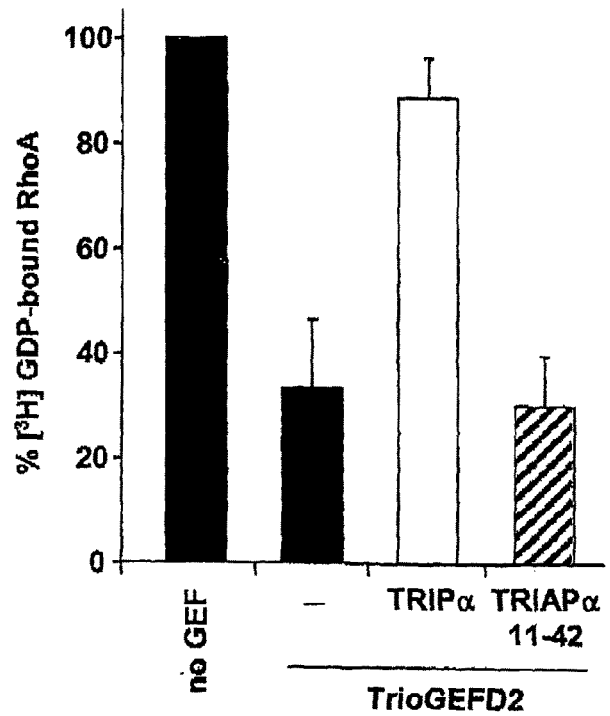

FIG. 4: TRIPα Shows the same Inhibitory Properties as TRIAPα

The y-axis represents the percentage of [$^3$H]GDP-bound RhoA.

A 42-amino acid peptide corresponding to the variable moiety of TRIAPα, TRIPα, and a deletion of TRIAPα 11-42, were tested in exchange assays for their ability to block TrioGEFD2 activity on RhoA. GEF assays were performed as described in FIG. 2A in the absence or in presence of 8 μM of the different inhibitors tested, as indicated.

The first black bar corresponds to the amount of [$^3$H]GDP bound-RhoA incubated without GEF. The second black bar corresponds to [$^3$H]GDP bound-RhoA incubated with TrioGEFD2 alone; the white bar corresponds to [$^3$H]GDP bound-RhoA incubated with TrioGEFD2 and TRIPα, and the hatched bar corresponds to [$^3$H]GDP bound-RhoA incubated with TrioGEFD2 and TRIAPα 11-42.

TRIPα inhibits TrioGEFD2 activity to a similar level than TRIAPα, whereas a deletion construct of TRIAPα, TRIAPα 11-42, is unable to block TrioGEFD2 exchange activity.

FIGS. 5A, 5B, 5C and 5D: Inhibition of TrioGEFD2 by TRIPα in Intact Cells.

Figure 5A:
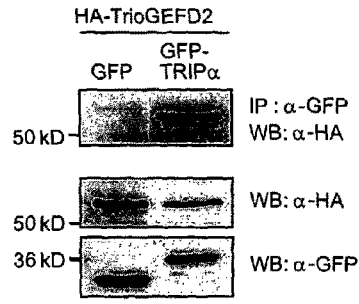

FIG. 5A represents the interaction of HA (Haemagglutinin-Tagged)-TrioGEFD2 with GFP-TRIPα in COS cells.

HA-TrioGEFD2 was co-expressed with either GFP-TRIPα (right column) or GFP alone (left column). The upper panel represents the immunoprecipitation (IP) with the anti-GFP antibody (α-GEP), followed by a western-blot (WB) using the anti-HA antibody (α-HA) and the two lower panels represent the expression of the proteins in the cell lysates.

Figure 5B:
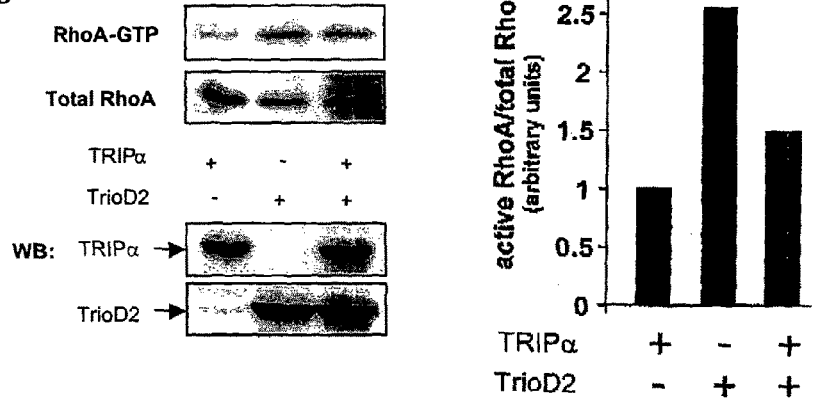

FIG. 5B represents the inhibitory effect of TRIPα on TrioGEFD2-mediated RhoA activation in intact cells using the RhoA activity assay, COS cells were transfected with GFP-TRIPα (left line), TrioGEFD2 (middle line) or both (right line). Cell lysates were subjected to GST-pulldown using the recombinant RBD (RhoA binding domain) fragment of the RhoA-specific effector Rhotekin. The presence of the GTP-bound form of RhoA and of the total RhoA protein was detected using a monoclonal anti-RhoA antibody and is represented in the upper two panels. GFP-TRIPα and TrioGEFD2 expression in the cell lysates is shown in the lower two panels.

Quantification of the RhoA activity assay is shown in the right part of the figure. The y-axis represents the ratio between active RhoA and total RhoA, in arbitrary units.

The left black column corresponds to COS cells transfected with GFP-TRIPα; the middle black column corresponds to COS cells transfected with TrioGEFD2 and the right black column corresponds to COS cells transfected with GFP-TRIPα and TrioGEFD2.

In COS cells, TRIPα is able to inhibit TrioGEFD2-mediated RhoA activation.

Figure 5C:
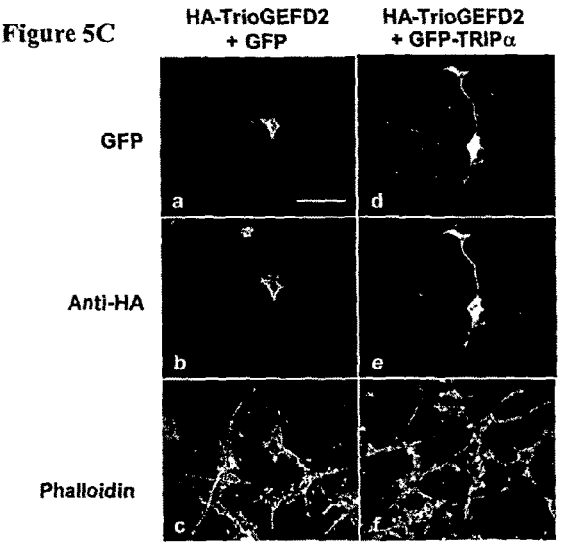

FIG. 5C represents the inhibition by TRIPα of the TrioGEFD2 effect in neuronal morphology. Immunofluorescence images of PC12 cells co-transfected with HA-TrioGEFD2 and either GFP-TRIPα (panels d, e, f) or GFP alone panels a, b, c) are shown. After 48 hours of expression, cells were treated for 16 hours with NGF (nerve growth factor) (50 ng/ml) and fixed. Expression of GFP and GFP-TRIPα was directly visualised (a, d) whereas overexpressed TrioGEFD2 was detected using the 12CA5 anti-HA antibody followed by AMCA-conjugated anti-mouse IgG (b, e). Filamentous actin was stained with Rhodamine-conjugated Phalloidin (c, f). Scale bar: 20 μm.

Figure 5D:
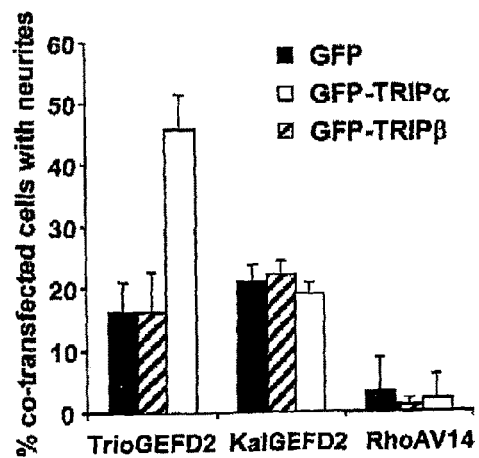

FIG. 5D represents the quantification of the TIPα inhibition of Trio-GEFD2-induced neuronal morphology. The y-axis of this figure represents the percentage of co-transfected cells with neurites.

Cells were transfected with HA-tagged TrioGEFD2 (left side of the figure), myc-tagged KalGEFD2 (middle of the figure) or RhoAV14 (a constitutively active mutant of RhoA) (right side of the figure), and with either GFP-TRIPα (white bars), GFP-TRIPβ (hatched bars) or GFP alone (black bars). Cells were processed as described in FIG. 5C and the number of co-transfected cells with neurites was counted. In conclusion, only the TrioGEFD2 effect is reversed by TRIPα.

Figure 6A:
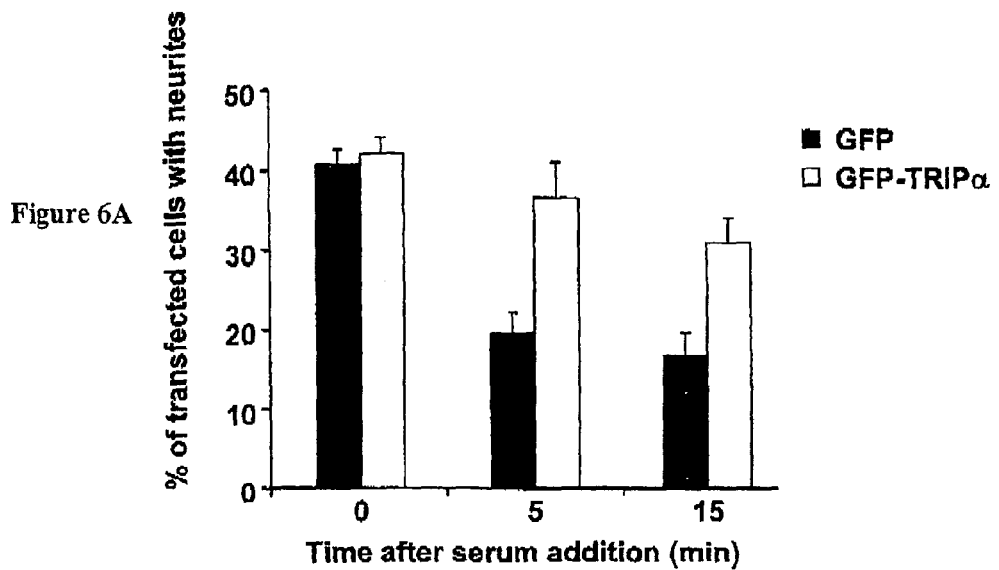
Figure 6B:
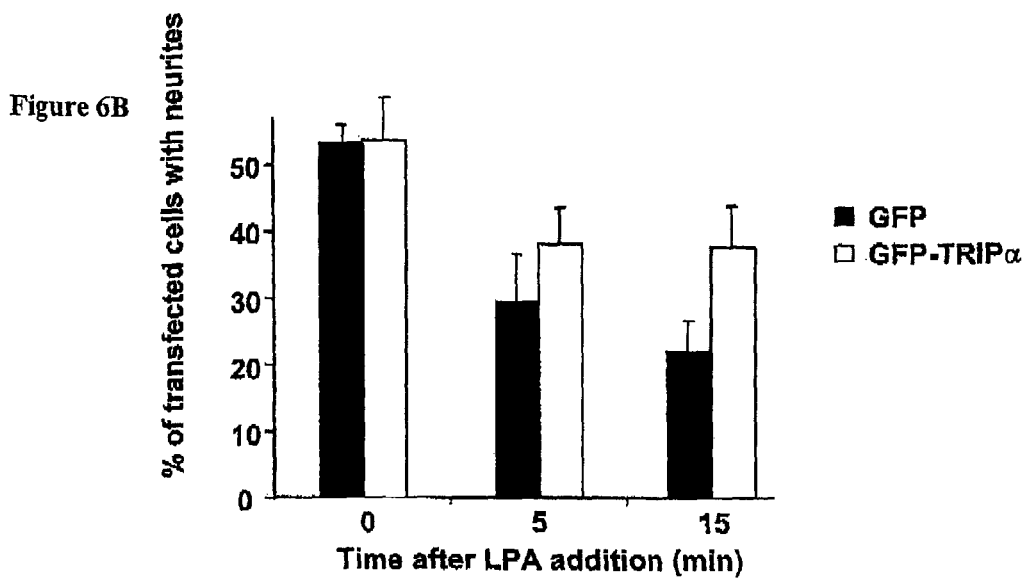
Figure 6C:
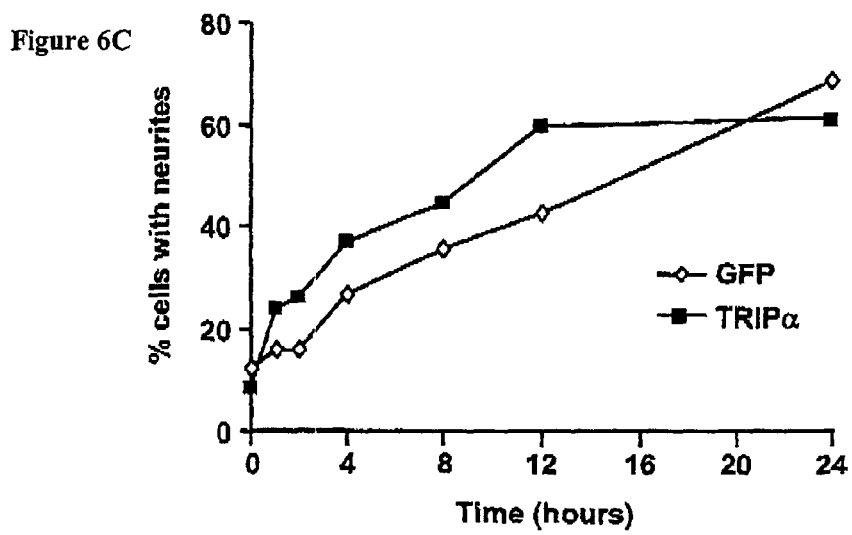

FIGS. 6A, 6B and 6C: Effect of TRIPα on Neuronal Morphology

FIG. 6A represents histograms quantifying the effects of GFP-TRIPα or GFP on serum induced neurite retraction in NGF-differentiated PC12 cells. The X-axis represents the time after serum addition in minutes and the Y-axis represents the percentage of transfected cells with neurites.

Cells were transfected with GFP-TRIPα (white bars) or GFP (black bars) and differentiated with NGF (50 ng/ml). Serum was added and neurite retraction was followed for 15 minutes. The number of transfected cells with neurites was counted from at least 200 cells in 3 independent experiments.

FIG. 6B represents histograms quantifying the effects of GFP-TRIPα or GFP on LPA (lysophosphatidic acid) induced neurite retraction in NGF-differentiated PC12 cells. The X-axis represents the time after LPA addition in minutes and the Y-axis represents the percentage of transfected cells with neurites.

Cells were transfected with GFP-TRIPα (white bars) or GFP (black bars) and differentiated with NGF (50 ng/ml). 10 μM LPA was added and neurite retraction was followed for 15 minutes. The number of transfected cells with neurites was counted from at least 200 cells in 3 independent experiments.

Altogether, these results suggest that TRIPα prevents serum- and LPA-induced neurite retraction, and that this effect is due to the modulation of Trio activity.

FIG. 6C shows that TRIPα enhances NGF-induced neurite outgrowth. The X-axis represents the time in hours and the Y-axis represents the percentage of cells with neurites.

PC12 were transfected with GFP-TRIPα (lack squares) or GFP (white diamonds) and subjected to a time-course exposure to NGF (50 ng/ml). At each time-point cells were fixed and the number of transfected cells with neurites was counted from at least 200 cells.

Figure 7A:
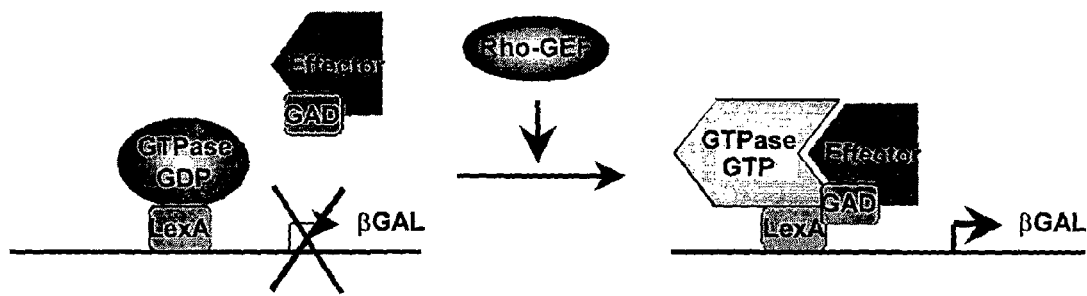
Figure 7B:
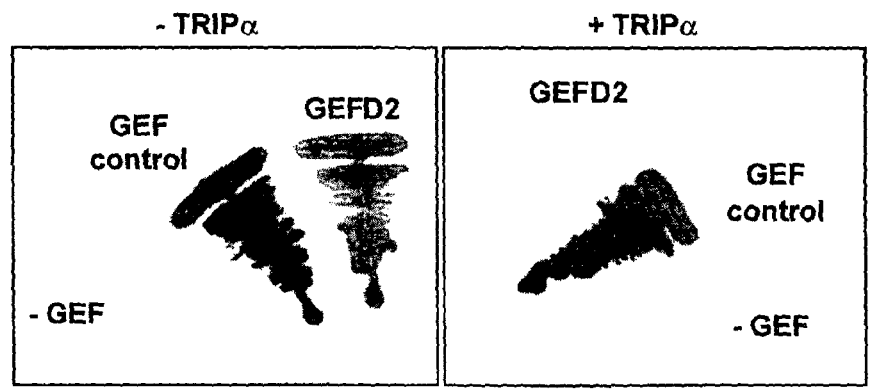

FIGS. 7A and 7B: Inhibition of TrioGEFD2 Activity by TRIPα in the Yeast Exchange Assay (YEA)

FIG. 7A shows the principle of the Yeast Exchange Assay, based on the two-hybrid system. The wild type GTPase is fused to the LexA DNA binding domain (Matchmaker GAL4 two-hybrid, Clontech Laboratories, Inc., USA) and the effector to the GAL4-activation domain (Matchmaker GAL4 two-hybrid, Clontech, Inc., USA). Under these conditions, no binding occurs in the TAT7 strain (De Toledo et al., 2000). Upon addition of a third plasmid expressing the GEF, the GTPase gets activated and binds to its effector, thus leading to the transactivation of the reporter gene LacZ.

FIG. 7B shows that TRIPα inhibits TrioGEFD2-mediated RhoA activation in the YEA system. TrioGEFD2, a control GEF (GEF720) or an empty vector (–GEF: corresponds to a vector without GEF) were introduced into the YEA system and analysed for their ability to transactivate the reporter gene in absence (left panel) or in the presence (right panel) of TRIPα. This Figure shows that only GEFD2 is affected by TRIPα and is unable to activate RhoA, while the control GEF is unaffected.

Figure 8:
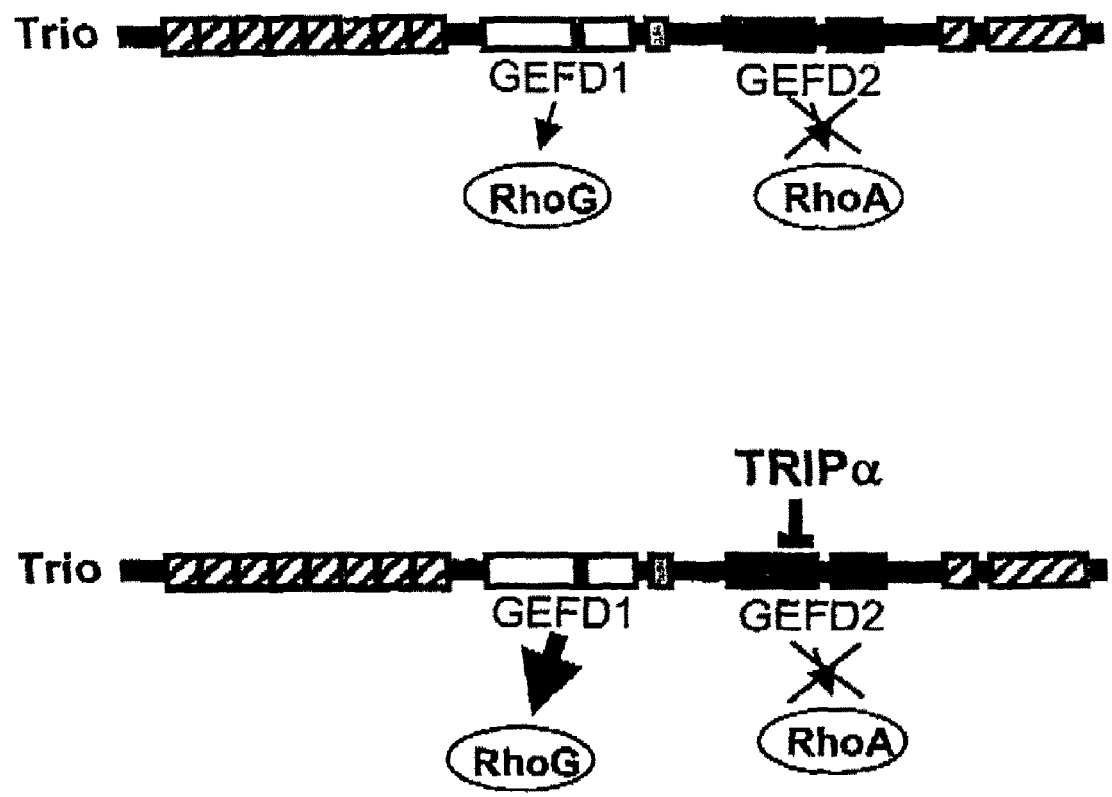

FIG. 8: Effect of TRIPα on Full Length Trio in the YEA System

Full length Trio was introduced into the YEA and tested for its ability to activate RhoA and RhoG respectively, in the presence or absence of TRIPα. The table below summarizes the effect of TRIPα on Trio as schematized in this Figure.

|         | −TRIPα | +TRIPα |
|---------|--------|--------|
| RhoA    | −      | −      |
| RhoG    | + +    | + + + +|

"+ +" represents a slight activation of the reporter gene, "+ + + +" represents a strong activation of the reporter gene and "−" represents no activation of the reporter gene.

FIGS. 9a-9f: Expression of CAV-GFP-TRIP Fusion Peptides in Rat Cortical Neurons.

Rat E18 (embryonic day 18) cortical neurons were infected with adenovirus vectors coding for GFP (9a, 9b), GFPTRIPα (9c, 9d), or GFPTRIPβ (9e, 9f) and fixed 48 hours later. Cells were visualised by Differential Interference Contrast (Nomarski) (9b, 9d, 9f and expression of GFP-fusion peptides was visualised by direct fluorescence (9a, 9c, 9e).

A majority of the cells were infected by the adenovirus vectors and expressed the GFP-fusion peptides.

EXAMPLES

Isolation of Aptamers Binding to TrioGEFD2 using a Genetic Screen in Yeast

In order to identify specific inhibitors of TrioGEFD2, a recently developed strategy was used, this strategy being derived from the yeast two hybrid system, where the cDNA library of preys has been replaced by a combinatorial library of short peptides (20 amino acids) in fusion with the bacterial protein thioredoxin A (Colas et al., 1996). This strategy has been successfully used to isolate specific inhibitors of the cyclin-dependent kinases (Cdks), the cell cycle transcription factor E2F, or the viral HPV16 E6 oncoprotein and HBEV core protein (Colas et al., 1996; Butz et al., 2001; Fabrizzio et al., 1999; Geyer et al., 2000). The TrioGEFD2 bait was constructed as follows: plasmid pMTHATrio1848-2298 (Bellanger et al., 1998) was digested with EcoRI/XhoI and the insert cloned in pEG202EcoRI/XhoI to generate the bait pEG202TroGEFD2. Yeast strain EGY048 (Colas et al., 1996) was transformed with pEG202TroGEFD2 and subsequently with the library of Thioredoxin constrained aptamers according to standard procedures (Ito et al., 1983). After transformation, cells were allowed to recover for 4 hours in galactose containing medium before plating on selective galactose medium. Of the 2×10⁶ screened colonies, those growing in the selective medium were recovered and retested for interaction. Among the aptamers binding to TrioGEFD2 in yeast, three were selected for further analysis: TRIAPα, TRIAPβ, TRIAPγ (FIG. 1A). Binding specificity was investigated by screening for interaction with the following baits: TrioDH2 (a.a. 1848-2096), TrioPH2 (a.a. 2107-2223), TrioGEFD1 (a.a. 1232-1629), Dbl (a.a. 498-826), Vav (ala. 172-598) (Zhang et al, 1994), GEFD2 domain of Kalirin (a.a. 1640-1980)(Penzes et al., 2001), p115RhoGEF (a.a. 391-870) (Wells et al, 2002) and PDZRhoGEF (a.a. 964-1362) (Fukuhara et al., 1999). None of these aptamers interacted with other RhoGEF members such as Dbl, Vav, and the RhoA-specific GEFs p115RhoGEF and PDZRhoGEF. TRIAPα interacted weakly with TrioGEFD1 and with the second GEF domain of the Trio family member Kalirin. In addition, TRIAPα and not TRIAPβ and TRIAPγ interacted with the DH2 catalytic domain alone.

The variable moiety of the aptamers is inserted into the thioredoxin A protein at the amino acid 35 position as described elsewhere (Geyer et al., 2000). Its nucleic acid sequence was determined using an ABIPRISM automated sequencer (Perkin Elmer) and the predicted amino acid sequence deduced. The variable sequence of TRIAPα (42 amino acids) showed no homology to any sequence in the databases.

TRIAPα Inhibits the In Vitro Exchange Activity of TrioGEFD2 Towards Rhoa.

As described earlier, TrioGEFD2 displays specific exchange activity on RhoA (Debant et al., 1996), and not on Rac or Cdc42. An in vitro guanine nucleotide exchange (GEF) assay was used to test whether the TrioGEFD2-binding aptamers could inhibit the catalytic activity of TrioGEFD2 towards RhoA. For this purpose, the aptamers TRIAPα, TRIAPβ and TRIAPγ (including the Trx gene) were excised from pEG202 as EcoRI/NotI fragments and cloned into pGEX4T1 EcoRI/NotI. The aptamers were then expressed and purified from bacteria as GST fusion proteins, using standard procedures (Smith and Johnson, 1988). GTPase-GST fusion proteins were prepared, loaded with [³H]GDP and the guanine nucleotide release assays were performed as described (Debant et al., 1996), using recombinant GST-TrioGEFD2 (a.a. 1848-2298), TrioDH2 (a.a. 1848-2096). For each point, 0.3 μM GTPase was mixed with or without 0.4 μM GEF in presence of non-labeled GTP, and the reaction mix was filtered after 0 min and 15 mm reaction at 25° C. The catalytic activity of TrioGEFD2 was thus measured by the decrease of the GTPase-associated radioactivity. The results are expressed as the ratio "exchange after 15 min over exchange after 0 min" (% bound [³H]GDP-RhoA). To measure the effect of the aptamers on the exchange activity, a 20-fold molar excess of GST-TRIAPs was pre-incubated with GEFD2 (or GEFD1) for 30 min on ice before the exchange assay was carried out. For each experiment, data were obtained in triplicate.

As shown in FIG. 2A, preincubation of a 20-fold molar excess of GST-TRIAPα (8 μM) with TrioGEFD2 (0.4 μM) significantly inhibited its in vitro catalytic activity towards RhoA, whereas the same amount of GST-TRIAPα, GST-TRIAPγ or GST-thioredoxin (GST-Trx) had no effect. GST-TRIAPα inhibited both TrioGEFD2 and TrioDH2 exchange activities, which is consistent with the fact that TRIAPα also recognised the DH2 catalytic domain in yeast. Moreover, inhibition of GEFD2 by OST-TRIAPα was concentration-dependent, with an apparent half-inhibitory concentration of around 4 μM (FIG. 2B).

TRIAPα Inhibition is Specific for TrioGEFD2

The effect of GST-TRIAPα on other Rho-GEFs that display in vitro exchange activity on RhoA was next tested to investigate whether TRIAPα inhibition was specific of TrioGEFD2. The exchange activities of the RhoGEF Lbc (a.a. 1-424, FIG. 3)(Zheng et al., 1995) and Dbl (a.a. 495-826, data not shown) were not affected by GST-TRIAPα. The effect of GST-TRIAPα on the catalytic activity of RhoGEFs that display a high sequence similarity with TrioGEFD2 was then tested: the recently identified RhoA-specific p63RhoGEF (Souchet et al., 2002) (a.a. 149-374, 71.5% identity with TrioGEFD2, 0.4 μM) and the second Rho-GEF domain of the Trio family member Kalirin (KalGEFD2, a.a. 1850-2190, 65% identity with TrioGEFD2, 1.7 μM). Different concentrations of RhoGEFs were used to yield similar nucleotide exchange specificity. For each exchange factor, three independent experiments were done in absence or in the presence of a 20-fold molar excess of GST-TRIAPα. GST-TRIAPα had no effect on the catalytic activity of p63RhoGEF and only weakly inhibited KalGEFD2 exchange activity on RhoA. GST-TRIAPα did not block TrioGEFD1 (a.a. 1232-1629, 0.1 μM) activity on RhoG (0.3 μM) (FIG. 3), even though TRIAPα bound TrioGEFD1 in yeast (FIG. 1). Thus, the in vitro inhibitory activity of TRIAPα was selective for TrioGEFD2 (see table I for summary of the tested RhoGEFs).

TABLE I

Binding and inhibition activity of TRIAPα on various RhoGEFs

| RhoGEFs | Binding in yeast | in vitro GEF assay |
|---|---|---|
| TrioDH2PH2 | +++[1] | +++[2] |
| TrioDH2PH2$_{L2051E}$ | +++[1] | nd[2] |
| TrioDH1PH1 | +[1] | −−[2] |
| KalirinDH2PH2 | +[1] | +[2] |
| Dbl | −−[1] | −−[2] |
| Vav | −−[1] | nd |
| p115RhoGEF | −−[1] | nd |
| PDZRhoGEF | −−[1] | nd |
| p63RhoGEF | nd | −−[2] |
| Lbc | nd | −−[2] |

+++[1] and +[1] represent respectively a full and a partial (see FIG. 1) binding capacity;
+++[2] and +[2] represent respectively a full and a partial (see FIG. 3) inhibitory effect;
−−[1] represents a lack of binding;
−−[2] represents a lack of inhibitory effect;
nd means not determined.

TRIPα has the Same Inhibitory Effect as TRIAPα

TRIAPα blocked TrioGEFD2 exchange activity when its conformation was constrained by the presence of thioredoxin. The role of the thioredoxin constraint in inhibition was evaluated by testing whether TrioGEFD2 activity could be blocked by a synthetic peptide of 42 amino acids, TRIPα (Trio Inhibitory Peptide), corresponding to the variable region of TRIAPα. Peptide synthesis was performed on Fmoc-L-Met_PEG-PS resin (Applied Biosystems, San Jose-Calif.) as previously described (Morris et al., 1999). The Fmoc deprotection time was increased all the synthesis long (7 to 9 min) and a 5 min capping by acetylation with 0.3 M acetyl imidazole in DMF was done after coupling, to prevent deleterious peptide synthesis. The peptide was deprotected, purified and analysed as described (Morris et al., 1999), except that dimethylsulfide (3%) was added to the deprotection mixture, to reduce methionine oxidation. MALDI (Matrix assisted laser desorption ionisation) mass spectra (MH+ =4423) and amino acid analyses after HCl hydrolysis were in line with the expected structure.

At the same dosage (20 fold molar excess), TRIPα was as potent as TRIAPα to block in vitro TrioGEFD2 exchange activity, suggesting that the thioredoxin scaffold is not required for the TRIAPα inhibitory effect on TrioDH2 catalytic activity (compare FIG. 4 and 2A).

Structure Function Analysis of TRIAPα

In order to map the sequence of TRIPα responsible for the inhibition of TrioGEFD2 activity, different truncations of the TRIPα variable region were tested for their effect on the in vitro TrioGEFD2 exchange activity. Deletion mutants were created in the variable region of GST-TRIAPα (still inserted in the thioredoxin scaffold) and tested for their ability to block TrioGEFD2 activity on RhoA. GEF assays were performed as described in FIG. 2A, in the presence or in the absence of 8 μM of the different inhibitors, as indicated (see Table IIA below). Deletion of the first 8 amino acids of TRIAPα (TRIAPα 9-42) did not alter its inhibitory effect while deletion of two additional amino acids (TRIAPα 11-42) completely abrogated its effect (FIG. 4 and Table IIA). C-terminal deletions in TRIAPα were also performed: TRIAPα 1-33, 9-40 (SEQ ID NO: 22), 9-38 (SEQ ID NO: 24), 9-36 (SEQ ID NO: 26), 9-34 (SEQ ID NO: 28), displayed fill inhibitory activity, while TRIAPα 9-33 (SEQ ID NO: 30) had a reduced activity. These data suggested that the minimal sequence required for TrioGEFD2 inhibition is amino acids 9-34.

In order to go further in the structure function analysis of TRIPα, the amino acids in the TRIPα sequence were systematically replaced by alanine residues, except for cysteine residues which were mutated to serine. For that purpose, point mutants were performed using the "Quick change Site-directed Mutagenesis kit" from Stratagene according to the manufacturer's instructions. All the mutants were tested for their ability to block in vitro TrioGEFD2 activity on RhoA. GEF assays were performed as described in FIG. 2A in the presence or in the absence of 8 μM of the different mutants. The data obtained are summarized in Table IIB.

So far, only 6 essential residues were found for the inhibition of TrioGEFD2 activity, and three of them are cysteine residues. We are currently investigating whether the presence of these amino acids is required for the correct tridimensional structure of the peptide or whether these residues directly participate in the inhibition of GEFD2 activity.

TABLE II structure function analysis of TRIAPα

| | Amino acids | Sequence | Inhibition of TrioGEFD2 activity | SEQ ID NO: |
|---|---|---|---|---|
| A | 1-42 | AREGADGAICGYNLATLVMLGPSERVFCPLCEPCSSDIYELM | ++ | SEQ ID NO: 4 |
| | 1-22 | AREGADGAICGYNLATLVMLGP | −− | SEQ ID NO: 61 |
| | 22-42 | PSERVFCPLCEPCSSDIYELM | −− | SEQ ID NO: 62 |
| | 9-42 | ICGYNLATLVMLGPSERVFCPLCEPCSSDIYELM | ++ | SEQ ID NO: 6 |
| | 11-42 | GYNLATLVMLGPSERVFCPLCEPCSSDIYELM | −− | SEQ ID NO: 63 |
| | 9-40 | ICGYNLATLVMLGPSERVFCPLCEPCSSDIYE | ++ | SEQ ID NO: 8 |
| | 9-38 | ICGYNLATLVMLGPSERVFCPLCEPCSSDI | ++ | SEQ ID NO: 10 |
| | 9-36 | ICGYNLATLVMLGPSERVFCPLCEPCSS | ++ | SEQ ID NO: 12 |
| | 9-34 | ICGYNLATLVMLGPSERVFCPLCEPC | ++ | SEQ ID NO: 14 |
| | 9-33 | ICGYNLATLVMLGPSERVFCPLCEP | + | SEQ ID NO: 16 |
| | 1-33 | AREGADGAICGYNLATLVMLGPSERVFCPLCEP | ++ | SEQ ID NO: 18 |
| B | | AREGADGAICGYNLATLVMLGPSERVFCPLCEPC**SSDIYELM SEQ ID NO: 4 | | |

A represents essential residues for inhibition of TrioGEFD2 activity
A represents non essential residues for inhibition of TrioGEFD2 activity
A represents non tested residues for inhibition of TrioGEFD2 activity Inhibition by TRIPα of TrioGEFD2-Mediated RhoA Activation in Intact Cells The Inventors next wanted to determine the effect of TRIPα on GEFD2-mediated RhoA activation in intact cells. First, it was checked whether TRIPα could bind to TrioGEFD2 in mammalian cells. For that purpose, vectors expressing the variable region of TRIAPα (TRIPα) fused to GFP in the pEGFP-C3 plasmid (Clontech) were designed. GFP or GFP-TRIPα were co-expressed with pMTHA-TroGEFD2 by transfection of COS cells using Lipofectamine Plus (Life Technologies) according to the manufacturer's protocol. Immunoprecipitation of GFP-tagged constructs from COS cell lysates were done with the polyclonal rabbit anti-GFP antibody (Torrey Pines Biolabs, Inc.). The presence of TrioGEFD2 in GFP-immunoprecipitates was revealed by western-blotting using the monoclonal anti-HA antibody 12CA5 (Boehringer/Roche). As shown in FIG. 5A, TrioGEFD2 was present in the GFP-TRIPα-, and not in the GFP-immunoprecipitates, indicating that TRIPα interacts with TrioGEFD2 in mammalian cells.

The Inventors then wanted to assess the inhibition by TRIPα of TrioGEFD2-mediated activation of endogenous RhoA in intact cells. To do so, the RhoA activity assay was used to detect the active GTP-bound form of RhoA (Ren et al., 1999). Briefly, COS cells were transfected as described in FIG. 5A with TrioGEFD2 in absence or in the presence of GFP-TRIAPα. 48 hours after transfection, cell lysates were subjected to GST-pull down using 20 µg of the recombinant RBD (RhoA binding domain) fragment of the RhoA-specific effector Rhotekin, that binds only to the activated GTP-bound form of RhoA. The presence of the activated RhoA in the samples was revealed using a monoclonal anti RhoA antibody (Santa-Cruz Biotechnology). As shown in FIG. 5B, the activation of RhoA by TrioGEFD2 was significantly inhibited by the co-expression of GFP-TRIPα showing that TRIPα is able to inhibit TrioGEFD2 activity in intact cells.

GFP-TRIPα Specifically Reverted the Inhibitory Effect of Ectopically Expressed TrioGEFD2 on NGF-Induced Neurite Outgrowth in PC12 Cells.

Numerous reports have established Rho-GTPases as key regulators of neuronal morphology (Luo, 2000). In neuronal cell lines, activation of RhoG, Rac and Cdc42 induces neurite outgrowth, while RhoA stimulation antagonises this effect by promoting neurite retraction (Katoh et al., 2000; Kozma et al., 1997; Yamaguchi et al., 2001). The PC12 cell line is a useful cellular model for studying Nerve Growth Factor (NGF)-induced neuronal differentiation. PC12-E2 cells were plated on collagen-coated 12 mm coverslips as described previously (Estrach et al., 2002) and transfected with the Lipofectamine Plus reagent (Life Technologies) according to the manufacturer's instructions. After transfection and differentiation with NGF (Promega, 50 ng/ml in DMEM medium supplemented with 0.5% horse serum (HS)) for 16 hours, PC12 cells were fixed and permeabilised as described (Estrach et al., 2002). Expression of proteins was visualised directly for GFP-constructs, with a monoclonal anti-HA antibody (12CA5) for HA-TrioGEFD2 or with a monoclonal anti-myc antibody (9E10) for Myc-Kalirin GEFD2 (aa 1850-2190) followed by MCA-conjugated anti-mouse IgG. Filamentous actin was stained with Rhodarnine-conjugated phalloidin. Cells were observed under a DIR Leica microscope using a 40× planapochromat lens. Images were recorded using a Hamamatsu CCD camera. All transfections were repeated at least three times, and an average of 200 cells was counted each time. Cells with neurites are defined as cells with neurites of at least twice the length of the cell body.

As already described in other studies (Kozma et al., 1997), it was observed that expression of an activated form of RhoA (RhoAV14) in PC12 cells prevented NGF-induced neurite outgrowth (FIG. 5D, black column). Similarly, it was noticed that expression of TrioGEFD2 and KalGEFD2 also prevented NGF-induced neurite outgrowth, which is consistent with their specificity for RhoA. For example, only 16% of PC12 cells expressing HA-TrioGEFD2 extended neurites in response to NGF (FIG. 5D, black column), whereas more than 50% of cells usually respond to NGF treatment (see FIG. 6). It was then tested whether GFP-TRIPα could revert the inhibitory effect of TrioGEFD2 on NGF-induced neurite outgrowth. Interestingly, co-expression of GFP-TRIPα with TrioGEFD2 reverted the Trio-dependent inhibition, since 45% of co-transfected cells extended neurites upon NGF treatment, while this reversion was not observed in presence of GFP alone or GFP-TRIPβ (FIGS. 5C and D). Since TRIPα slightly inhibited KalGEFD2 exchange activity in vitro, it was then tested whether TRIPα was able to affect KalGEFD2 activity in vivo. In contrast to TrioGEFD2, neurite extension was similarly inhibited by KalGEFD2 either with or without GEP-TRIPα co-expression (FIG. 5D). Taken together, these data show that TRIPα specifically inhibits the effect of ectopically expressed TrioGEFD2 on PC12 morphology.

Inhibition of Trio by TRIPα Protects PC12 Cells from Serum- and LPA-Induced Neurite Retraction Serum addition to neuronally-differentiated cells leads to rapid neurite retraction and growth cone collapse, which has been shown to be mediated by the GTPase RhoA (Jalink et al., 1994). Since Trio is an activator of RhoA and is expressed in PC12 cells (Estrach et al., 2002), it was analysed whether TRIPα could interfere with serum-induced neurite retraction in NGF-differentiated PC12 cells. To this end, PC12 cells expressing GFP-TRIPα, GFP (or GFP-TRIPα 11-42, data not shown) were exposed 16 hours to NGF (50 ng/ml) and transfected cells expressing either GFP-construct presented a similar neurite outgrowth after 16 hours of NGF treatment, indicating that TRIPα had no visible effect on the NGF pathway in these experimental conditions. After NGF treatment, cells were subjected to serum addition (DMEM medium supplemented with 10% HS and 5% fetal calf serum (FCS)) from 0 to 15 min (FIG. 6A). Cells were then fixed and permeabilised (Estrach et al., 2002) and observed as described in FIG. 5. Cells with neurites are defined as cells with neurites of at least twice the length of the cell body.

As illustrated in FIG. 6A, upon serum addition, GFP- (or GFP-TRIPα 11-42-, data not shown) expressing cells retracted their neurites by 15 min, while expression of TRIPα significantly inhibited this retraction (around 18% of GFP-expressing cells presented neurites versus 32% for the GFP-TRIPα expressing cells).

Among the serum components known to trigger neurite retraction and cell rounding in neuronal cells is lysophosphatidic acid (LPA) (Moolenaar et al., 1997). Thus, a similar neurite retraction assay was performed, except that, instead of the serum-containing medium, LPA (10 µM, Sigma) was added to TRIPα transfected and differentiated PC12 cells (FIG. 6B). Strikingly, TRIPα also inhibited LPA-mediated neurite collapse, since after 15 min more than 37% of TRIPα expressing cells still presented neurites, while only 22% of GFP transfected cells retained neurites.

Altogether, given the specificity of TRIPα for Trio, these results suggest that TRIPα prevents serum- and LPA-induced neurite retraction, and that this effect is due to the inhibition of the endogenous TrioGEFD2 activity.

TRIPα Enhances the Rac GTPase-Mediated Neurite Outgrowth Induced by NGF

As already mentioned, the Rac and RhoA pathways have antagonistic activities in the control of the neuronal morphology. Rac controls neurite outgrowth, while RhoA acts on neurite retraction (Luo, 2000). Given the properties of TRIPα on the protection against neurite retraction via the inhibition of the RhoA pathway, the Inventors wanted to determine whether TRIPα could indirectly facilitate Rac-mediated neurite outgrowth induced by NGF.

As shown in FIG. 6A, TRIPα does not seem to have an effect on the NSF-induced neurite outgrowth. However, since the NGF treatment was performed for 16 hours, it was still possible that the effect of TRIPα on the NGF-differentiation signal was masked by the long NGF exposure. To test this hypothesis, PC12 cells expressing GFP-TRIPα or CFP were subjected to a time-course exposure to NGF (50 ng/ml) for 1 to 24 hours. As shown in FIG. 6C, cells expressing GFP-TRIPα responded to NGF treatment more quickly than the control cells, suggesting that indeed GFP-TRIPα enhanced NGF-induced neurite outgrowth.

Control of Trio RhoGEF Activity by TRIAPα using Theyeast Exchange Assay.

In order to better characterise the effect of TRIAPα on the Trio full length RhoGEF activity, the yeast exchange assay (YEA) was used, which is a quick and quantitative test derived from the classical two-hybrid system allowing to measure Rho-GEF activity and specificity (De Toledo et al., 2000). This functional assay is based on the fact that the GTPase binds to its effector only if it is activated by a RhoGEF. Briefly, yeasts are transformed with the GTPase fused to the LexA binding domain (LexA), and its effector to the GAL-4 Activating Domain (GAD), and with the adequate Rho-GEF partner in the yeast strain TAT7 (FIG. 7). Only if the RhoGEF is present, the Rho-GTPase will be activated and will bind to its effector, resulting in a transcriptional active complex driving the expression of the reporter gene (βgal or HIS).

First of all, it was checked whether the activation of RhoA by TrioGEFD2 alone was blocked by the expression of TRIAPα in this system. The variable region of TRIAPα was cloned in the pRS422 vector, and subsequently transformed in the yeast strain TAT7 with the appropriate vectors according to standard procedures (Ito et al., 1983). As expected, the expression of TRIAPα blocked specifically TrioGEFD2-mediated activation of RhoA (FIG. 7B).

The Inventors then wanted to determine the effect of TRIAPα on Trio full length-mediated RhoA activation. Surprisingly, full-length Trio does not activate the RhoA pathway, suggesting that, under these conditions, TrioGEFD2 is not active in the context of the full-length protein (FIG. 8). In order to explain the effect of TRIAPα on neuronal morphology, it was checked whether TRIAPα could indirectly modulate TrioGEFD1-mediated RhoG activation that leads to Rac activation and neurite outgrowth. In the YEA system, Trio is able to activate RhoG in the context of the full-length protein, and surprisingly, the presence of TRIAPα greatly enhanced TrioGEFD1 activation of RhoG. This observation suggests that TRIAPα, by binding to TrioGEFD2, indirectly activates TrioGEFD1. This is consistent with the previous experiments showing that TRIAPα facilitates the effect of NGF on neurite outgrowth.

All together, these data suggest that TRIAPα protects cells from neurite retraction probably by enhancing the activity of TrioGEFD1 on the Rac pathway.

PCR-Mediated Random Mutagenesis of TRIAPα

PCR-mediated random mutagenesis was performed on TRIAPα to isolate TRIPα-related peptides that could have the following properties:

1) a TRIPα-related peptide with higher affinity for TrioGEFD2 to enhance TRIPα biological activity on the protection against neurite retraction;
2) as described earlier, TRIAPα binds to TrioGEFD1 but does not affect its exchange activity; in this context, the mutagenesis allows us to find potent TrioGEFD1 inhibitors;
3) given the high sequence similarity between the different members of the Rho-GEF family, it should be also possible to isolate aptamers against other RhoGEF family members by screening a large number of mutagenised aptamers.

Briefly, the PCR-mediated random mutagenesis is done on TRIAPα according to the protocol described in (Geyer et al., 2000; Cadwell and Joyce, 1992) to introduce random point mutations distributed throughout the amplified sequence. The amplified PCR-products are then tested for their affinity towards their target and their capacity to inhibit the RhoGEF target activity.

This is done by testing the putative candidates in a yeast two hybrid system where the reporter-dependent growth observed is directly correlated with the strength of interaction (Sardet et al., 1995; Durfee et al., 1993). The putative candidates that bind strongly to TrioGEFD2 (or GEFD1 or any other RhoGEF) are then tested in the YEA assay for their capacity to inhibit the activation of their Rho-GTPase target.

The selected TRIAPα-related aptamers are then tested in in vitro GEF assay as described in FIG. 2A, and in intact cells for their expected biological effect (as described in FIGS. 5 and 6). Further, peptides corresponding to the variable region of these new aptamers are then synthesized (as described earlier) and tested for their effect in vitro and in vivo.

Efficient Targeting of TRIPα in Primary Cell Cultures and In Vivo

Until now, TRIPα has been delivered in the cytoplasm by transfection. In order to optimise the delivery of the inhibitor in cells difficult to transfect such as primary neuron cultures, or in a whole organism, different techniques were used to increase the peptide targeting.

Fusion peptides: numerous fusion peptides have been described: the antennapedia-derived peptides (Derossi et al., 1998), the HIV protein TAT (Nagahara et al., 1998), the Pep-1 (Morris et al., 2001) and SynB1 fusion peptides (Temsamani et al., 2000). All these fusion peptides are mixed with TRIPα (in a concentration range from 1 pM to 100 μM) and are tested first on the delivery of TRIPα in PC12 cells. The optimised delivery system is then used on primary neurons as described below.

Canine adenovirus vectors: Alternatively, in order to express TRIPα in primary neurons, a novel viral vector derived from canine aderiovirus was used: CAV-2 (Soudais et al., 2001). CAV-2 vectors transduce preferentially neuronal cells, and not glia or oligodendrocytes.

Figure 9:
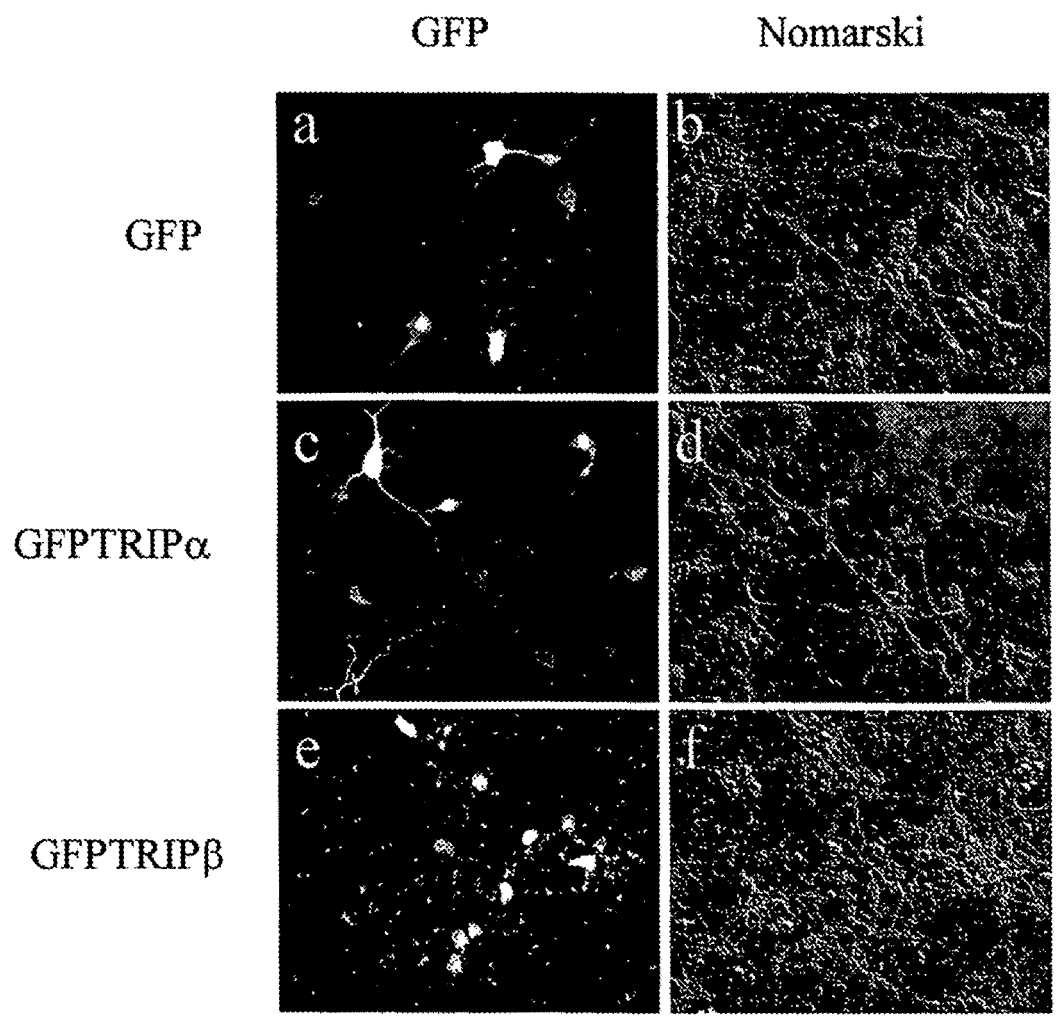

The construction and purification of CAV-GFP have been described (Kremer et al., 2000). The construction of CAV-GFP-TRIPα and CAV-GFP-TRIPβ were done by recombination in *E. coli* BJ5183 by using SwaI linearised pTGS412 and a fragment containing the inverted terminal repeat, the GFP-TRIPα or -TRIPβ cassette and the CAV-2B regions. The preparation of CAV-GFP, CAV-GFP-TRIPα, and CAV-GFP-TRWβ adenovirus vectors were done as described (Kremer et al., 2000) and stocks containing approx. $1-5 \times 10^{12}$ particles/ml were generated. Primary rat cortex cultures (embryonic day eighteen) were infected for 48 hours with our CAV-GFP fusion adenovirus (500 particles/cell). Cells were then fixed and expression of GFP fusion peptides was visualized directly. As shown in FIG. 9, cortical neurons infected by the CAV-GFP adenoviras show a nice GeP, GFP-TRIPα or GFP-TRIPβ expression.

Effect of TRIPα on the Morphology of Primary Neuron Cultures

Next, the effect of TRIAPα was tested on the morphology of primary neuron cultures. For that purpose, different neurons are isolated as follows:

Primary rat spinal cord neuron cultures: Primary motoneuron cultures are generated from embryonic day 14.5 (E14.5) rat spinal cords as described previously (Bechade et al., 1996). Cells are plated at $4 \times 10^5$ cells/ml on glass coverslips in four-well plates. Under these culture conditions, morphological differentiation appears by day 14.

Primary rat hippocampal neurons: Cultures of rat hippocampal neurons are prepared from hippocampi of 18-day-old fetal rats as described previously (Goslin and Banker, 1998). Hippocampi are dissociated by treatment with 0.25% trypsin and trituration with a Pasteur pipette. Dissociated cells are plated on coverslips with the appropriate substrate, in MEN (Modified Eagle's Medium) with 10% horse serum, at 1-5× $10^5$ cells/ml. After cell attachment, coverslips are transferred onto a glial cell layer, which provides factors necessary for survival and differentiation. Cells are maintained in MEM with 1% N2 (Invitrogen Inc.), 2 mM glutamine and 1 mg/mil BSA. Under these conditions, hippocampal neurons extend rapidly small processes of which one will become the axon (Armano et al., 2002).

Rat hippocampal slices: Rat hippocampal slices are prepared from P8 rats (post-natal day 8) with a tissue chopper as described previously (Stoppini et al., 1991). Briefly, the hippocampus is dissected in ice-cold dissection medium HEM and penicillin/Streptomycin), sliced transversely and separated from one another in culture medium (0.5×MEM, 0.25× HBSS, 0.25× decomplemented horse serum, penicillin/streptomycin and 1 mM glutamine). Slices are immediately plated onto membrane inserts in Petri dishes containing 1 ml of medium, or infected with CAV-GFP or CAV-GFP-TRIPα adenovirus vectors, 2 days post plating. Slices are then fixed and processed for immunofluorescence as described previously (Nakayama et al., 2000).

Rat retinal neurons: To culture retinal neurons, retinas are removed from postnatal day 1 to 5 (P1-P5) rat pups and the cells are dissociated with 12.5 U/ml papain in HBSS, 0.2 mg/ml DL-cysteine and 20 μg/ml USA, as described (Lehmann et al., 1999). Cells are plated on the appropriate substrate in DMEM with 10% FBS, vitamins and penicillin/streptornycin. Neurons are visualized by fluorescence microscopy anti-βIII tubulin antibody, which detects growing retinal ganglion cells (RGC)(Fournier and McKerracher, 1997).

Depending on the cell type, cells at different days post-plating are transduced with: i) virus stocks expressing CAV-GFP and CAV-GFP-TRIPα at approx. 100 particles/cell for 24 to 48 hours. Under these conditions, both GEP-constructs transduce the majority of neurons in the culture (see FIG. 9); ii) with fusion peptides as described before; iii) alternatively, neurons are transfected with GFP-TRIPα or control plasmid by biolistic transfection (Nakayama et al., 2000).

Neurons expressing the different GFP-constructs are examined for the morphology of their axons and dendrites, on different extracellular matrix substrates and in response to repulsive cues (Fournier and Strittmatter, 2001).

Effect of TRIPα In Vivo

The effect of TRIPα tin vivo is determined by using different assays as follows:

Effect of TRIPα on Crushed Optic Nerves in Adult Rats

To test the effect of TRIPα on damaged neurons, regeneration of retinal ganglion cell (RGC) axons in the optic nerve was examined 2 weeks after optic nerve crush. The procedure is the one as described in Lehmann et al. (1999). Briefly, RGCs are axotomised by constriction made on the optic nerve of anaesthetised rats. To apply TRIPα to crushed nerves, GST-TRIPα (2 to 100 μg) and GST control, or the synthetic TRIPα peptide, or alternatively CAV-GFP-TRIPα expression virus stocks, are applied around the optic nerve using Elvax tubes, The crushed and regenerating axons are then visualized by anterograde labelling with cholera toxin injected into the eye 12 days after optic nerve crush, and 2 days later, sections of the optic nerve are observed using fluorescent microscopy (for details see Lehman et al., 1999).

Effect of TRIPα on Spinal Cord Lesions in Adult Rats

To induce lesions in the spinal cord of adult rats the procedure is the one as described in Huang et al. (1999). The corticospinal tracts of the dorsal half of the spinal cord are severed with a pair of microcissors. Simultaneously, TRIPα is either injected (1 pM to 100 μM) or introduced by adenovirus vectors into the spinal cord. At different times post lesion (1 week to 3 weeks), mice are injected with a specific marker (WGA-HRP) into the sensory-motor cortex as described previously (Li et al., 1996). Two days after injection, mice are sacrificed and longitudinal sections of the spinal cord are made and revealed by HRP histochemistry.

REFERENCES

Armano, S. et al. (2002) *J Biol Chem* 277, 10467-73,

Awasaki, T. et al. (2000) The Drosophila trio plays an essential role in patterning of axons by regulating their directional extension. *Neuron* 26, 119-131, Bateman, J., Shu, H. & Van Vactor, D. (2000) The guanine nucleotide exchange factor trio mediates axonal development in the Drosophila embryo. *Neuron* 26, 93-106, Bechade, C., Colin, I., Kirsch, J., Betz, H. and Tiller, A. (1996) *Eur J Neurosci* 8, 429-35, Bellanger, J. M., Lazaro, J. B., Diriong, S., Fernandez, A., Lamb, N. and Debant, A. (1998) *Oncogene* 16, 147-152, Bellanger, J. M. et al. (2000) The Rac1- and RhoG-specific GEF domain of Trio targets filamin to remodel cytoskeletal actin. *Nat Cell Diol* 2, 888-892, Benard et al. (2002) *Methods in enzymology*, vol. 345, p. 349-359, Blangy, A. et al. (2000) TrioGEF1 controls Rac- and Cdc42-dependent cell structures through the direct activation of rhoG. *J Cell Sci* 113, 729-739, Boguski, M. S. & McCormick, F. (1993) Proteins regulating Ras and its relatives. *Nature* 366, 643-654, Butz, K., Denk, C., Fitscher, B., Crnkovic-Mertens, I., Ullmann, A., Schroder, C. H. and Hoppe-Seyler, F. (2001) *Oncogene* 20, 6579-86, Cadwell, R. C. and Joyce, G. F. (1992) *PCR Methods Appl* 2, 28-33, Colas, P., Cohen, B., Jessen, T., Grishina, I., McCoy, J. and Brent, R. (1996) *Nature* 380, 548-50, De Toledo, M., Colombo, K., Nagase, T., Ohara, O., Fort, P. and Blangy, A. (2000) *FEBS Lett* 480, 287-92, Debant, A., Serra-Pages, C., Seipel, K., O'Brien, S., Tang, M., Park, S. H. and Streuli, M. (1996) *Proc Natl Acad Sci USA* 93, 5466-5471, Derossi, D., Chassaing, G. and Prochiantz, A. (1998) *Trends Cell Biol* 8, 84-7, Durfee, T., Becherer, K., Chen, P. L., Yeh, S. H., Yang, Y., Kilburn, A. E., Lee, W. H. and Elledge, S. J. (1993) *Genes Dev* 7, 555-69, Estrach, S., Schmidt, S., Diriong, S., Penna A., Blangy, A., Fort, P. and Debant, A. (2002) *Current Biology* 12, 307-312, Fabbrizio, E., Le Cam, L., Polanowska, I., Kaczorek, M., Lamb, N., Brent, R. and Sardet, C. (1999) *Oncogene* 18, 4357-4363, Fournier, A. E. and McKerracher, L. (1997) *J Neurosci* 17, 4623-4632, Fournier, A. E. and Strittmatter, S. M. (2001) *Curr Opin Neurobiol* 11, 89-94, Fukuhara S, Murga C, Zohar M, Igishi T, Gutkind J S. (1999) *J Biol Chem.* 274, 5868-79, Geyer, C. R. and Brent, R. (2000) *Methods Enzymol* 328, 171-208, Goslin, K. and Banker, G. (1998) in: Culturing Nerve Cells, pp. 339-370 (Goslin, G. B. a. K., Ed.) MIT Press, Cambridge, Mass., Hall, A. (1998) Rho GTPases and the actin cytoskeleton. *Science* 279, 509-514, Hart, M. J. et al. (1994) Cellular transformation and guanine nucleotide exchange activity are catalyzed by a common domain on the dbl oncogene product. *J Biol Chem* 269, 62-65, Huang, D. W., McKerracher, L., Braun, P. E. and David, S. (1999) *Neuron* 24, 639-647, Ito, H., Fukuda, Y., Murata, K. and Kimura, A. (1983) *J Bacteriol* 153, 163-168, Jalink, K., van Corven, E. J., Hengeveld, T., Morii, N., Narumiya, S. and Moolenaar, W. H. (1994) *J Cell Biol* 126, 801-810, Katoh, H., Yasui, H., Yamaguchi, Y., Aoki, J., Fujita, H., Mori, K. and Negishi, M. (2000) *Mol Cell Biol* 20, 7378-7387, Kozma, R., Samer, S., Ahmed, S. and Lim, L. (1997) *Mol Cell Biol* 17, 1201-1211, Kremer, E. J., Boutin, S., Chillon, M. and Danos, O. (2000) *J Virol* 74, 505-512, Lehmann, M., Fournier, A., Selles-Navarro, I., Dergham, P., Sebok, A., Leclerc, N., Tigyi, G. and McKerracher, L. (1999) *J Neurosci* 19, 7537-7547, Li, M., Shibata, A., Li, C., Braun, P. E., McKerracher, L., Roder, L., Kater, S. B. and Davis, S. (1996) *J Neurosci Res.* 46, 404-414, Liebl, E. C. et al. (2000) Dosage-sensitive, reciprocal genetic interactions between the Abl tyrosine kinase and the putative GOF trio reveal trio's role in axon pathfinding. *Neuron* 26, 107-118, Luo, L. (2000) *Nat Rev Neurosci* 1, 173-180, Moolenaar, W. H., Kranenburg, O., Postma, F. R. and Zondag, G. C. (1997) *Curr Opin Cell Biol* 9, 168-173, Morris, M. C., Depollier, J., Mery, J., Heitz, F. and Divita, G. (2001) *Nat Biotechnol* 19, 1173-1176, Morris, M. C., Mery, J., Heitz, A., Heitz, F. and Divita, G. (1999) *J Pept Sci* 5, 263-271, Nagahara, H. et al. (1998) *Nat Med* 4, 1449-1452, Nakayama, A. Y., Harms, M. B. and Luo, L. (2000) *J Neurosci* 20, 5329-5338, Newsome, T. P. et al. (2000) Trio combines with dock to regulate Pak activity during photoreceptor axon pathfinding in Drosophila. *Cell* 101, 283-294, O'Brien, S. P. et al. (2000) Skeletal muscle deformity and neuronal disorder in Trio exchange factor-deficient mouse embryos. *Proc Natl Acad Sci USA* 97, 12074-12078, Penzes, P. et al. (2001) The neuronal Rho-GEF Kalirin-7 interacts with PDZ domain-containing proteins and regulates dendritic morphogenesis. Neuron 29, 229-242, Penzes P, Johnson R C, Kambampati V, Mains R E, Fipper B A (2001) *J Neurosci* 21, 8426-34, Ren, X. D., Kiosses, W. B. and Schwartz, M. A. (1999) *Embo J* 18, 578-85, Sardet, C., Vidal, M., Cobrinik, D., Geng, Y., Onufryk, C., Chen, A. and Weinberg, R. A. (1995) *Proc Natl Acad Sci USA* 92, 2403-7, Seipel, K. et al. (1999) Trio amino-terminal guanine nucleotide exchange factor domain expression promotes actin cytoskeleton reorganization, cell migration and anchorage-independent cell growth. *J Cell Sci* 112, 1825-1834, Seipel, K., O'Brien, S. P., Iannotti, E., Medley, Q. G. & Streuli, M. (2001) Tara, a novel F-actin binding protein, associates with the Trio guanine nucleotide exchange factor and regulates actin cytoskeletal organization. *J Cell Sci* 114, 389-399, Smith, D. B. and Johnson, K. S. (1988) *Gene* 67, 31-40, Souchet, M. et al. (2002) *J. Cell. Science* 115, 629-640, Soudais, C., Laplace-Buithe, C., Kissa, K. and Kremer, E. J. (2001) *Faseb J* 15, 2283-5, Stam, J. C. & Collard, J. G. (1999) The DH protein family, exchange factors for Rho-like GTPases. *Prog Mol Subcell Biol* 22, 51-83, Steven, R. et al. (1998) UNC-73 activates the Rac GTPase and is required for cell and growth cone migrations in C. elegans. *Cell* 92, 785-795, Stoppini, L., Buchs, P. A. and Muller, D. (1991) *J Neurosci Methods* 37, 173-82, Temsamani, J., Sche-mnarm, J. M., Rees, A. R. and Kackorek, M. (2000) *Current Trends in pharmaceutical science and technology today* 3, 155-162, Wells C, Jiang X, Gutowski S, Sternweis P C (2002) *Methods Enzymol* 345, 371-82, Yamaguchi, Y., Katoh, H., Yasui, H., Mori, K. and Negishi, M. (2001) *J Biol Chem* 15, 15, Zhang, R., Tsai, F. Y. and Orkin, S. H. (1994) *Proc Natl Acad Sci USA* 91, 12755-9, Zheng, Y., Olson, M. F., Hall, A., Cerione, R. A. and Toksoz, D. (1995) *J Biol Chem* 270, 9031-4.

The invention claimed is:

1. An isolated polypeptide specifically inhibiting TrioGEFD2 domain, selected from the group consisting of:
   (i) an isolated polypeptide consisting of the amino acid sequence SEQ ID NO: 4,
   wherein
   amino acid residues at positions 10, 11, 12, 28, 29 and 31 are essential residues for inhibition of TrioGEFD2 activity, and
   amino acid residues at positions 1-9, 13, 16, 23-24, and 32-42 are non essential residues for inhibition of TrioGEFD2 activity; and
   (ii) an isolated polypeptide consisting of a sequence selected from the group consisting of SEQ ID NO: 6, SEQ ID NO: 8, SEQ ID NO: 10, SEQ ID NO: 12, SEQ ID NO: 14, SEQ ID NO: 16 and SEQ ID NO: 18, wherein said polypeptide inhibits TrioGEFD2 domain, and wherein said polypeptide does not inhibit TrioGEFD1 domain.

2. A nucleotide sequence consisting of
SEQ ID NO: 3 coding for the isolated polypeptide represented by SEQ ID NO: 4.

3. A fragment of the nucleotide sequence defined in claim 2, wherein said fragment consists of a sequence selected from the group consisting of the nucleotide sequences: SEQ ID NO: 5 coding for the polypeptide consisting of SEQ ID NO: 6, SEQ ID NO: 7 coding for the polypeptide consisting of SEQ ID NO: 8, SEQ ID NO: 9 coding for the polypeptide consisting of SEQ ID NO: 10, SEQ ID NO: 11 coding for the polypeptide consisting of SEQ ID NO: 12, SEQ ID NO: 13 coding for the polypeptide consisting of SEQ ID NO: 14, SEQ ID NO: 15 coding for the polypeptide consisting of SEQ ID NO: 16, and SEQ ID NO: 17 coding for the polypeptide consisting of SEQ ID NO: 18.

4. A pharmaceutical composition characterized in that it comprises a pharmaceutically acceptable carrier and an isolated polypeptide specifically inhibiting TrioGEFD2 domain, selected from the group consisting of:
   (i) an isolated polypeptide consisting of the amino acid sequence SEQ ID NO: 4,
   wherein
   amino acid residues at positions 10, 11, 12, 28, 29 and 31 are essential residues for inhibition of TrioGEFD2 activity, and
   amino acid residues at positions 1-9, 13, 16, 23-24, 26 and 32-42 are non essential residues for inhibition of TrioGEFD2 activity; and
   (ii) an isolated polypeptide consisting of a sequence selected from the group consisting of SEQ ID NO: 6, SEQ ID NO: 8, SEQ ID NO: 10, SEQ ID NO: 12, SEQ ID NO: 14, SEQ ID NO: 16 and SEQ ID NO: 18, wherein said polypeptide inhibits TrioGEFD2 domain, and wherein said polypeptide does not inhibit TrioGEFD1 domain.

* * * * *